(12) United States Patent
Scholl et al.

(10) Patent No.: US 10,561,465 B2
(45) Date of Patent: *Feb. 18, 2020

(54) SURGICAL SPINAL CORRECTION

(71) Applicant: NuVasive, Inc., San Diego, CA (US)

(72) Inventors: Thomas Scholl, San Diego, CA (US); Mark Peterson, Central Point, OR (US); Robert Isaacs, Chapel Hill, NC (US)

(73) Assignee: NuVasive, Inc., San Diego, CA (US)

( * ) Notice: Subject to any disclaimer, the term of this patent is extended or adjusted under 35 U.S.C. 154(b) by 847 days.

This patent is subject to a terminal disclaimer.

(21) Appl. No.: 15/027,904

(22) PCT Filed: Oct. 9, 2014

(86) PCT No.: PCT/US2014/059974
§ 371 (c)(1),
(2) Date: Apr. 7, 2016

(87) PCT Pub. No.: WO2015/054543
PCT Pub. Date: Apr. 16, 2015

(65) Prior Publication Data
US 2016/0235480 A1    Aug. 18, 2016

Related U.S. Application Data

(60) Provisional application No. 61/888,990, filed on Oct. 9, 2013.

(51) Int. Cl.
*A61B 34/10* (2016.01)
*A61B 17/70* (2006.01)
(Continued)

(52) U.S. Cl.
CPC ............ *A61B 34/10* (2016.02); *A61B 5/0086* (2013.01); *A61B 5/4566* (2013.01);
(Continued)

(58) Field of Classification Search
CPC ............................... A61B 34/10; A61B 34/25
(Continued)

(56) References Cited

U.S. PATENT DOCUMENTS

| 5,658,286 A | 8/1997 | Sava |
| RE42,226 E * | 3/2011 | Foley ................. A61B 17/7083 600/426 |

(Continued)

FOREIGN PATENT DOCUMENTS

| DE | 102011006574 | 10/2012 |
| WO | WO-2009035358 | 3/2009 |

(Continued)

OTHER PUBLICATIONS

Schlenk, Richard P., et al., "Biomechanics of Spinal Deformity"; Neurosurg Focus, 14(1): Article 2, Jan. 2003; vol. 14 (Year: 2003).*
(Continued)

*Primary Examiner* — Si Ming Ku

(57) ABSTRACT

A method is provided for planning, performing, and assessing of surgical correction to the spine during a spinal surgical procedure. This method is implemented by a control unit through a GUI to digitize screw locations, digitize anatomical reference points, accept one or more correction inputs, and generate one or more rod solution outputs shaped to engage the screws at locations distinct from the originally digitized locations.

20 Claims, 61 Drawing Sheets

(51) Int. Cl.
*A61B 34/20* (2016.01)
*A61B 5/00* (2006.01)
*A61B 17/86* (2006.01)

(52) U.S. Cl.
CPC ...... *A61B 17/7002* (2013.01); *A61B 17/7086* (2013.01); *A61B 17/86* (2013.01); *A61B 34/20* (2016.02); *A61B 2034/104* (2016.02); *A61B 2034/105* (2016.02); *A61B 2034/107* (2016.02); *A61B 2034/108* (2016.02)

(58) Field of Classification Search
USPC .......................................................... 606/102
See application file for complete search history.

(56) References Cited

U.S. PATENT DOCUMENTS

| | | | |
|---|---|---|---|
| 7,957,831 B2* | 6/2011 | Isaacs | A61B 17/7011 700/165 |
| 8,235,998 B2 | 8/2012 | Miller | |
| 8,442,621 B2* | 5/2013 | Gorek | A61B 34/20 600/424 |
| 8,744,826 B2 | 6/2014 | Skalli | |
| 8,753,346 B2 | 6/2014 | Suarez | |
| 8,831,324 B2 | 9/2014 | Penenberg | |
| 8,983,813 B2 | 3/2015 | Miles | |
| 8,992,542 B2 | 3/2015 | Hagag | |
| 9,119,670 B2 | 9/2015 | Yang | |
| 9,129,054 B2 | 9/2015 | Nawana | |
| 9,204,937 B2 | 12/2015 | Edelhauser | |
| 9,211,145 B2 | 12/2015 | Pereiro de Lamo | |
| 9,233,001 B2 | 1/2016 | Miles | |
| 9,248,002 B2 | 2/2016 | McCarthy | |
| 9,320,604 B2 | 4/2016 | Miles | |
| 9,408,698 B2 | 8/2016 | Miles | |
| 9,452,050 B2 | 9/2016 | Miles | |
| 9,572,682 B2 | 2/2017 | Aghazadeh | |
| 9,597,157 B2 | 3/2017 | Hagag | |
| 9,662,228 B2 | 5/2017 | McCarthy | |
| 9,700,292 B2 | 7/2017 | Nawana | |
| 9,724,167 B2 | 8/2017 | Ziaei | |
| 2007/0073137 A1 | 3/2007 | Schoenefeld | |
| 2012/0035507 A1 | 2/2012 | George et al. | |
| 2013/0053854 A1 | 2/2013 | Schoenefeld et al. | |
| 2013/0345757 A1 | 12/2013 | Stad | |
| 2014/0076883 A1 | 3/2014 | Brailovski | |
| 2014/0081659 A1 | 3/2014 | Nawana | |
| 2014/0378828 A1 | 12/2014 | Penenberg | |
| 2015/0073265 A1 | 3/2015 | Popovic | |
| 2015/0157416 A1 | 6/2015 | Andersson | |
| 2015/0227679 A1 | 8/2015 | Kamer | |
| 2015/0238271 A1 | 8/2015 | Wollowick | |
| 2015/0282796 A1 | 10/2015 | Nawana | |

FOREIGN PATENT DOCUMENTS

| | | |
|---|---|---|
| WO | WO-2013085982 | 6/2013 |
| WO | WO-2014016824 | 1/2014 |
| WO | WO-2014088801 | 6/2014 |

OTHER PUBLICATIONS

Smith, et al., "Clinical and Radiographic Evaluation of the Adult Spinal Deformity Patient"; Neurosurg Clin N An 24 (2), 143-156; Feb. 21, 2013 (Year: 2013).*

Lehman, et al., "Do Intraoperative Radiographs in Scoliosis Surgery Reflect Radiographic Result?", Clin Orthop Relat Res (2010) 468: 679-686 (Year: 2010).*

Tanquay, el al., "Relation Between the Sagittal Pelvic and Lumbar Spine Geometries Following Surgical Correction of Adolescent Idiopathic Scoliosis"; European Spine Journal, Apr. 2007; 16(4): 531-536 (Year: 2007).*

Schlenk, Richard P., et al., "Biomechanics of Spinal Deformity"; Neurosurg Focus, 14(1): Article 2, Jan. 2003; vol. 14.

Smith, et al., "Clinical and Radiographic Evaluation of the Adult Spinal Deformity Patient"; Neurosurg Clin N An 24(2), 143-156; Feb. 21, 2013.

Tanquay, el al., "Relation Between the Sagittal Pelvic and Lumbar Spine Geometrics Following Surgical Correction of Adolescent Idiopathic Scoliosis"; European Spine Journal, Apr. 2007; 16(4): 531-536.

Lehman, et al., "Do Intraoperative Radiographs in Scoliosis Surgery Reflect Radiographic Result?"; Clin Orthop Relat Res (2010) 468: 679-686.

Extended European Search Report for European Patent Application No. 14852650.2-1501.

Written Opinion of the International Searching Authority for PCT/US2014/059974.

* cited by examiner

SURGICAL SPINAL CORRECTION

CROSS-REFERENCE TO RELATED APPLICATIONS

This application is an international patent application claiming the benefit of priority from commonly owned and U.S. Provisional Patent Application Ser. No. 61/888,990, entitled "Systems and Methods for Performing Spine Surgery," and filed on Oct. 9, 2013, the entire contents of which is hereby expressly incorporated by reference into this disclosure as if set forth in its entirety herein.

FIELD

The present application pertains to spine surgery. More particularly, the present application pertains to systems and methods related to the planning, performing, and assessing of surgical correction to the spine during a spinal surgical procedure.

BACKGROUND

The spinal column is a highly complex system of bones and connective tissues that provide support for the body and protect the delicate spinal cord and nerves. The spinal column includes a series of vertebral bodies stacked atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the endplates of the upper and lower vertebrae are inclined towards one another.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, degenerative disc disease, fractured vertebrae, and the like). Patients that suffer from such conditions often experience extreme and debilitating pain, as well as diminished nerve function. Posterior fixation for spinal fusions, decompression, deformity, and other reconstructions are performed to treat these patients. The aim of posterior fixation in lumbar, thoracic, and cervical procedures is to stabilize the spinal segments, correct multi-axis alignment, and aid in optimizing the long-term health of the spinal cord and nerves.

Spinal deformity is the result of structural change to the normal alignment of the spine and is usually due to at least one unstable motion segment. The definition and scope of spinal deformity, as well as treatment options, continues to evolve. Surgical objectives for spinal deformity correction include curvature correction, prevention of further deformity, improvement or preservation of neurological function, and the restoration of sagittal and coronal balance. Sagittal plane alignment and parameters in cases of adult spinal deformity (ASD) are becoming increasingly recognized as correlative to health related quality of life score (HRQOL). In the literature, there are significant correlations between HRQOL scores and radiographic parameters such as Sagittal Vertical Axis (SVA), Pelvic Tilt (PT) and mismatch between pelvic incidence and lumbar lordosis.

The SRS-Schwab classification of ASD was developed to assist surgeons with a way to categorize ASD, and provide methods of radiographic analysis. This classification system helps provide a protocol for pre-operative treatment planning and post-op assessment. The current environment to utilize this classification system requires surgeons to examine pre-operative patient films and measure pelvic incidence, lumbar lordosis, pelvic tilt, and sagittal vertical axis either manually or through the use of pre-operative software. After the procedure, the surgeon examines the post-operative films and measures the same parameters and how they changed as a result of the surgery. A need exists for systems and methods for assessing these and other spinal parameters intraoperatively and assessing changes to these intraoperative spinal parameters as a surgical procedure progresses towards a pre-operative plan.

During spinal surgeries, screws, hooks, and rods are devices used to stabilize the spine. Such procedures often require the instrumentation of many bony elements. The devices, for example rods, can be extremely challenging to design and implant into the patient. Spinal rods are usually formed of stainless steel, titanium, cobalt chrome, or other similarly hard metal, and as such are difficult to bend without some sort of leverage-based bender. Moreover, a spinal rod needs to be oriented in six degrees of freedom to compensate for the anatomical structure of a patient's spine as well as the attachment points (screws, hooks, etc.) for securing the rod to the vertebrae. Additionally, the physiological problem being treated as well as the physician's preferences will determine the exact configuration necessary. Accordingly, the size, length, and particular bends of the spinal rod depends on the size, number, and position of each vertebrae to be constrained, the spatial relationship amongst vertebrae, as well as the screws and hooks used to hold the rods attached to the vertebrae.

The bending of a spinal rod can be accomplished by a number of methods. The most widely used method is a three-point bender called a French Bender. The French bender is a pliers-like device that is manually operated to place one or more bends in a rod. The French bender requires both handles to operate and provides leverage based on the length of the handle. The use of the French bender requires a high degree of physician skill because the determination of the location, angle, and rotation of bends is often subjective and can be difficult to correlate to a patient's anatomy. Other methods of bending a rod to fit a screw and/or hook construct include the use of an in-situ rod bender and a keyhole bender. However, all of these methods can be subjective, iterative, and are often referred to as an "art." As such, rod bending and reduction activities can be a time consuming and potentially frustrating step in the finalization of a complex and/or long spinal construct. Increased time in the operating room to achieve optimum bending can be costly to the patient and increase the chance of the morbidity. When rod bending is performed poorly, the rod can preload the construct and increase the chance of failure of the fixation system. The bending and re-bending involved can also promote metal fatigue and the creation of stress risers in the rod.

Efforts directed to computer-aided design or shaping of spinal rods have been largely unsuccessful due to the lack of bending devices as well as lack of understanding of all of the issues involved in bending surgical devices. Recently, in U.S. Pat. No. 7,957,831 to Isaacs, there is described a rod bending system which includes a spatial measurement sub-system with a digitizer to obtain the three dimensional location of surgical implants (screws, hooks, etc.), software to convert the implant locations to a series of bend instructions, and a mechanical rod bender used to execute the bend instructions such that the rod will be bent precisely to custom fit within each of the screws. This is advantageous because it provides quantifiable rod bending steps that are customized to each patient's anatomy enabling surgeons to create custom-fit rods on the first pass, thereby increasing the speed and efficiency of rod bending, particularly in complex cases. This, in turn, reduces the morbidity and cost associated with such procedures. However, a need still exists for improved rod bending systems that allow for curvature and deformity correction in fixation procedures, provide the user with more rod bending options, and accommodate more of the user's clinical preferences.

SUMMARY

The present invention includes a system and methods for rod bending that enable a user (e.g., surgeon) to customize rod bend instructions to suit the desired correction of a patient's spinal condition.

According to a broad aspect, the present invention includes a spatial tracking system for obtaining the three-dimensional position information of surgical implants, a processing system with software to convert the implant locations to a series of bend instructions based on a desired correction, and a mechanical rod bender for bending a surgical linking device to achieve the desired spinal correction.

According to another aspect of the present invention, the spatial tracking system includes includes an infrared (IR) position sensor and at least one IR-reflective tracking array attached to at digitizer pointer used to digitize the surgical implant location. The spatial tracking system is communicatively linked to the processing system such that the processing system may utilize the spatial position information to generate bend instructions.

According to another aspect of the present invention, the processing system is programmed to generate bend instructions based on one or more surgeon-prescribed clinical objectives. For example, the processing system may be programmed to create a custom bend, adjust one or more points to which the rod will be bent to, suggest a pre-bent rod option, provide spinal correction in the sagittal plane, provide spinal correction in the coronal plane, and provide correction to achieve global spinal balance, and as well as perform a plurality of predetermined functions. The processing system may be further programmed to receive preoperative spinal parameters, input planned or target spinal parameters, and/or track intraoperative measurement of those parameters. The processing system is further configured to preview and display the results of these clinical objectives and/or predetermined functions to the user in a meaningful way.

According to another aspect of the invention, one or more surgical procedures may be performed using various embodiments of the system.

According to another aspect of the invention, there is provided a system for intraoperative planning and assessment of spinal deformity correction during a surgical spinal procedure, the system comprising: a spatial tracking system comprising an IR sensor and an IR tracking array, said IR tracking array being arranged along a proximal end of a surgical pointer tool capable of digitizing the location of an implanted surgical device and relaying to the spatial tracking system via the IR sensor; a control unit in communication with the spatial tracking system, said control unit being configured to: (a) receive the digitized location data of a plurality of implanted screws; (b) receive the digitized location data of at least one anatomical reference point; (c) generate at least one virtual anatomic reference line based on the digitized location data of said at least one anatomical reference point; (d) accept one or more spine correction inputs; and (e) generating at least one rod solution output shaped to engage the screws at locations distinct from the digitized location.

According to one or more embodiments, the spine correction input is a spine correction in the coronal plane. According to some implementations, the spine correction input comprises aligning all of the digitized screw locations relative to the CSVL in the coronal plane. According to some implementations, the system generates a rod solution output that includes T a vertically straight rod along at least a portion of the length.

According to some implementations, the virtual anatomic reference line is the central sacral vertical line (CSVL). According to some implementations, the at least one anatomical reference point comprises at least two points that correlate to the CSVL. According to other implementations, the at least one anatomical reference point comprises two points that lie along the CSVL. According to some implementations, the at least two points are the left iliac crest, the right iliac crest, and the midpoint of the sacrum. According to some implementations, the at least one anatomical reference point comprises a superior point and an inferior point on the sacrum.

According to one or more embodiments, the control unit is configured to generate at least one measurement value based on at least two anatomically-based reference lines. According to some implementations, this measurement value may be an offset distance between the two reference lines. According to some implementations, the two reference lines are the central sacral vertical line (CSVL) and the C7 plumb line (C7PL). According to yet other implementations, the control unit is further configured to assess intraoperative spinal balance based on a relationship between said CSVL and C7PL and communicate that assessment to a user. In some implementations, the r relationship may be based on the coronal offset distance between the CSVL and C7PL. In yet other implementations, the communication may be such that a color. For example, the communication may be such that a first color designates an offset distance indicating a balanced spine within the coronal plane and a second color designates an offset distance indicating an unbalanced spine within the coronal plane.

According to one or more embodiments, the control unit is configured to generate at least one measurement value based on at least one anatomically-based reference point. According to one or more implementations, the measurement value comprises an intraoperative lumbar lordosis angle and a planned pelvic incidence angle. According to some implementations, the control unit is further configured to assess intraoperative spinal balance based on a relationship between an intraoperative lumbar lordosis angle measurement and a planned pelvic incidence angle. In some instances, the lumbar lordosis angle and pelvic incidence angle may be measured at least once during the operation progress. According to some implementations, the relationship between lumbar lordosis and pelvic incidence may be based on the variance between the intraoperative lumbar lordosis angle and the planned pelvic incidence angle. According to some implementions, the communication may be a color. For example, a first color may designate variance indicating a balanced spine within the sagittal plane and a second color designates an variance distance indicating an unbalanced spine within the sagittal plane.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE PREFERRED EMBODIMENT

Illustrative embodiments of the invention are described below. In the interest of clarity, not all features of an actual implementation are described in this specification. It will of course be appreciated that in development of any such actual embodiment, numerous implantation-specific decisions must be made to achieve the developers' specific goals such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

Figure 1:
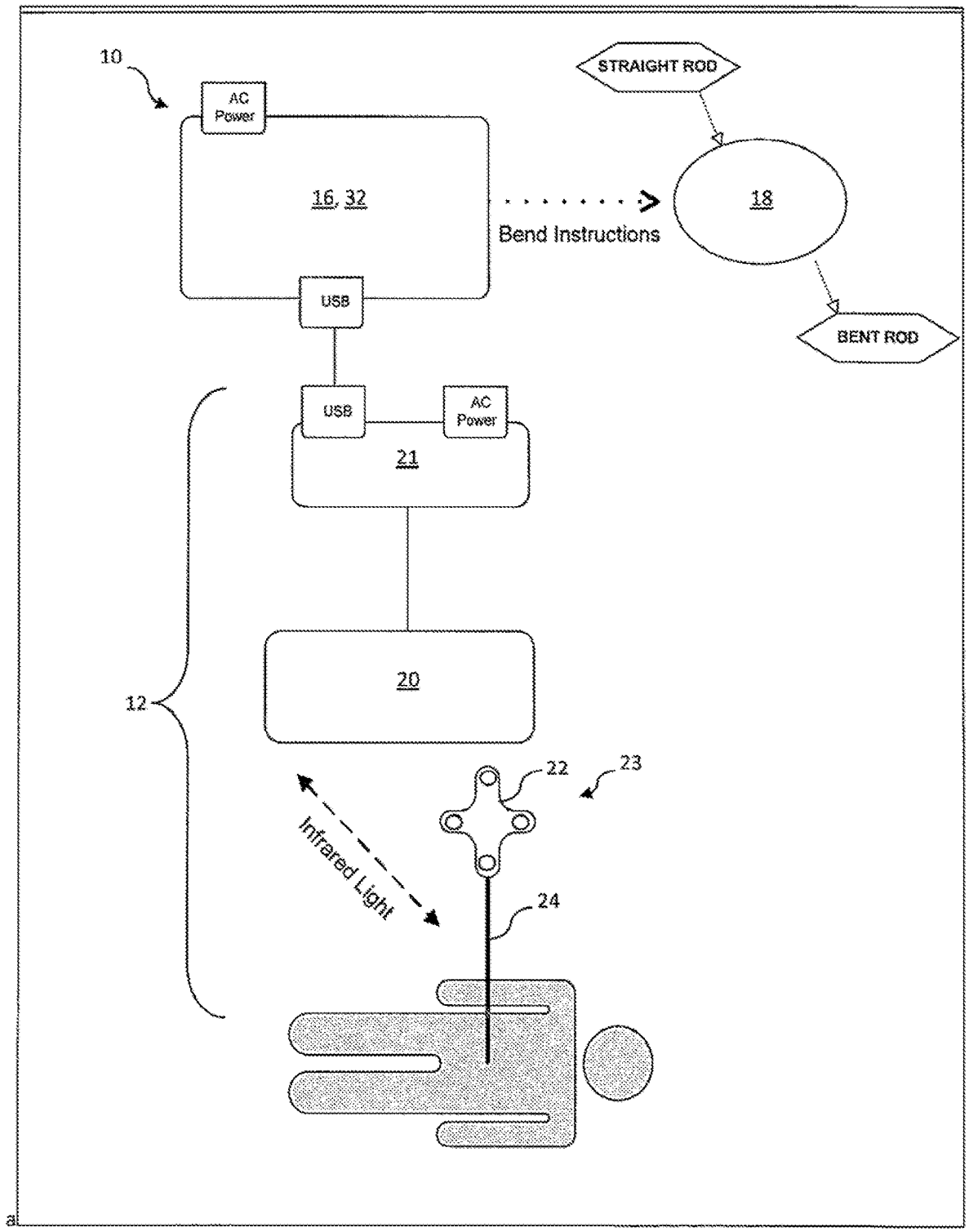
FIG. 1 is a surgical procedure setup depicting the components of a surgical planning, assessment, and correction system, according to one embodiment.

With reference now to FIG. 1, there is shown, by way of example, one embodiment of a surgical planning, assessment, and correction system 10 including a spatial tracking system 12 to obtain the location of one or more surgical implants 14, a control unit 16 containing software to convert the implant locations to a series of bend instructions, and a bending device 18 to execute the bend instructions.

Preferably, the spatial tracking system 12 includes an IR position sensor 20, a digitizer pointer 23, as well as other components including Host USB converter 21. The spatial tracking system 12 is in communication with control unit 16. The control unit 16 has spatial relation software and C-arm video import capabilities and is communicatively linked to the display 32 so that information relevant to the surgical procedure may be conveyed to the user in a meaningful manner. By way of example, the relevant information includes, but is not limited to, spatial positioning data (e.g., translational data in the x, y, and z axes and orientation/rotational data $R_x$, $R_y$, and $R_z$) acquired by the IR position sensor 20 and intraoperative fluoroscopic images generated by the C-arm fluoroscope.

According to one or more embodiments, the system 10 comprises a neuromonitoring system communicatively linked to the spatial tracking system 12 and/or the C-arm via the control unit 16. By way of example only, the neuromonitoring system may be the neuromonitoring system shown and described in U.S. Pat. No. 8,255,045, entitled "Neurophysiologic Monitoring System" and filed on Apr. 3, 2008, the entire contents of which are hereby incorporated by reference as if set forth fully herein.

Figure 2:
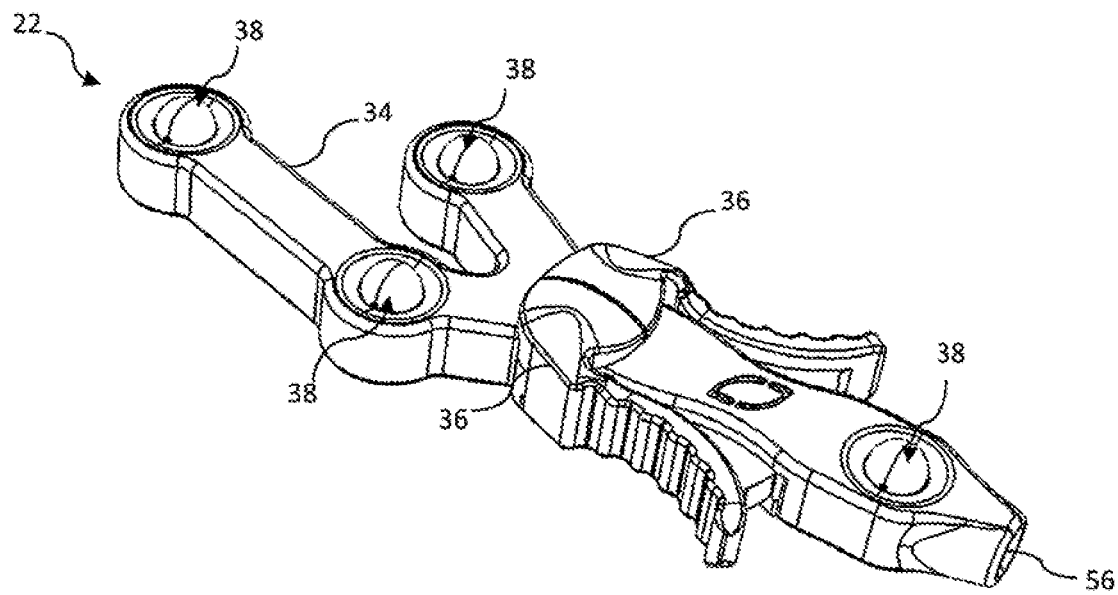
FIG. 2 is a perspective view of one embodiment of a digitizer array in the closed position comprising part of the system of FIG. 1.
Figure 3:
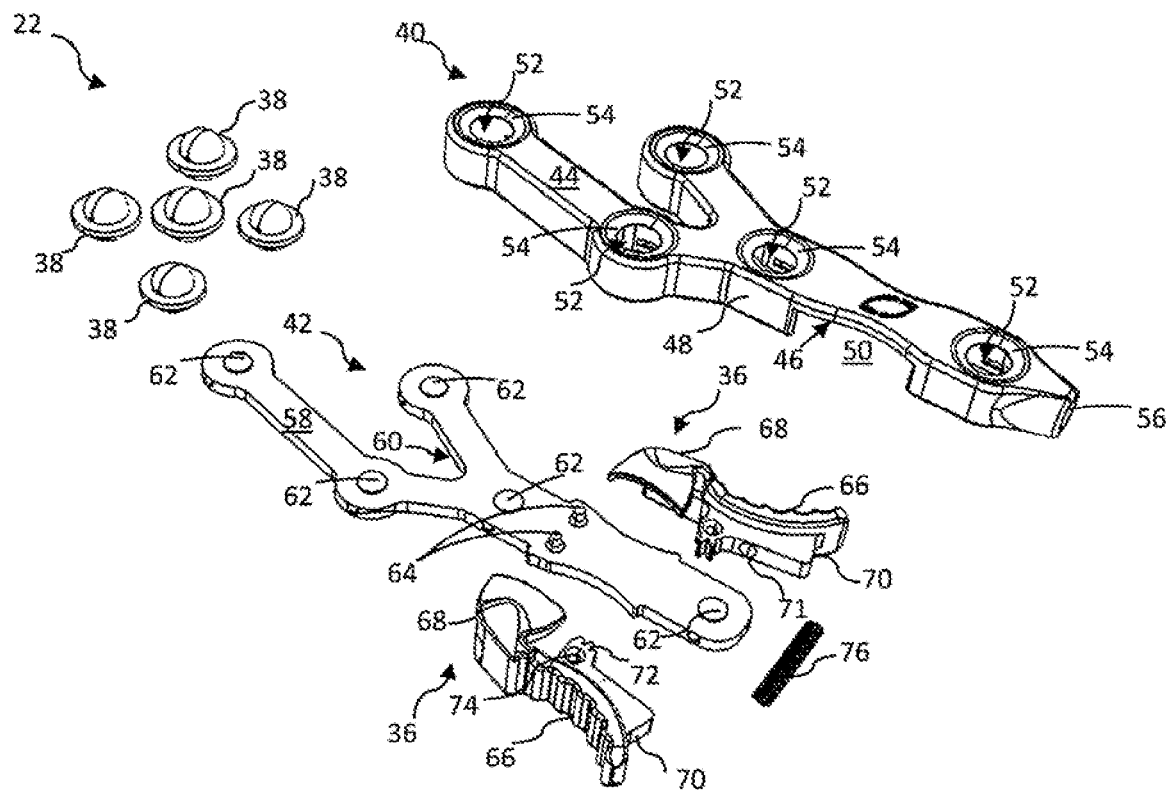
FIG. 3 is an exploded perspective view of the digitizer array of FIG. 2.
Figure 4:
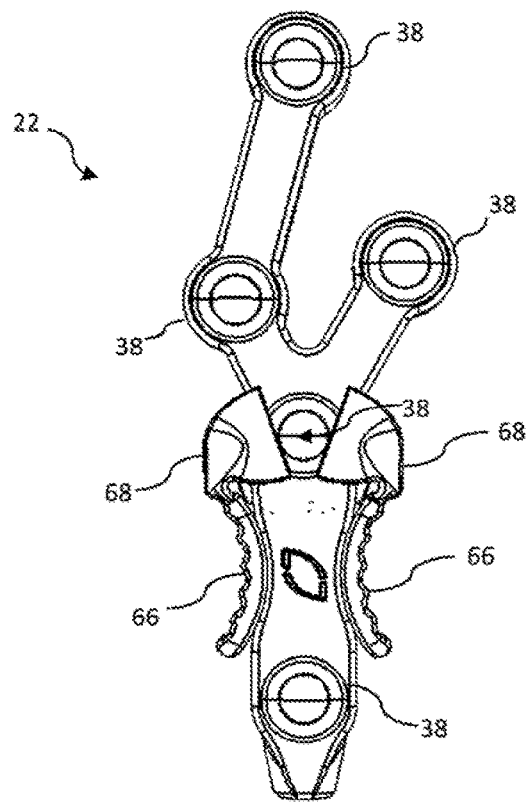
FIG. 4 is a perspective view of the digitizer array of FIG. 2 in the open position.

FIGS. 2-9 depict the various components of one or more digitizer pointers 23 for use with the present invention. FIGS. 2-4 detail an example IR-reflective tracking array 22 component of the digitizer pointer 23. Array 22 includes a housing 34, bilateral shutters 36, and a plurality of IR-reflective spheres 38 arranged in a calculated manner at various locations on the array 22 such that their position information is selectively detectable by the IR position sensor 20. Housing 34 comprises a top housing 40, bottom housing 42, and a distal threaded aperture 56 configured to threadably receive the threaded end 78 of a stylus (e.g., stylus 24, 26, 28, and/or 30). Top housing portion 40 is further comprised of upper portion 44, underside 46, and sides 48. A plurality of sphere apertures 52 extend between upper portion 44 and underside 46 and are sized and dimensioned to receive reflective spheres 38 within recessed pockets 54. Each side 48 includes cutout 50 sized and dimensioned to receive tongue 70. Bottom housing 42 is comprised of a first face 58 and a second face 60. The first face 58 includes nesting platforms 62 and bullet posts 64. Each shutter 36 includes handle portion 66, cover portion 68, tongue 70, interdigitating gear teeth 72, and channel 74 for receiving bullet posts 64. A spring 76 extends between the two shutters 36 and is held in place via spring posts 71.

In an assembled state, each IR-reflective sphere 38 is nested on a platform 62. Top housing 40 is placed over bottom housing 42 in a snap fit configuration such that each IR-reflective sphere 38 fits within a recessed pocket 54 within its respective sphere aperture 52. According to one implementation, bilateral shutters 36 are positioned over the housing 34 with tongues 70 sliding into cutouts 50 such that each shutter cover 68 obscures exactly one half of the IR-reflective sphere 38 (for example, the middle IR-reflective sphere 38) as depicted in FIG. 2.

Figure 5:
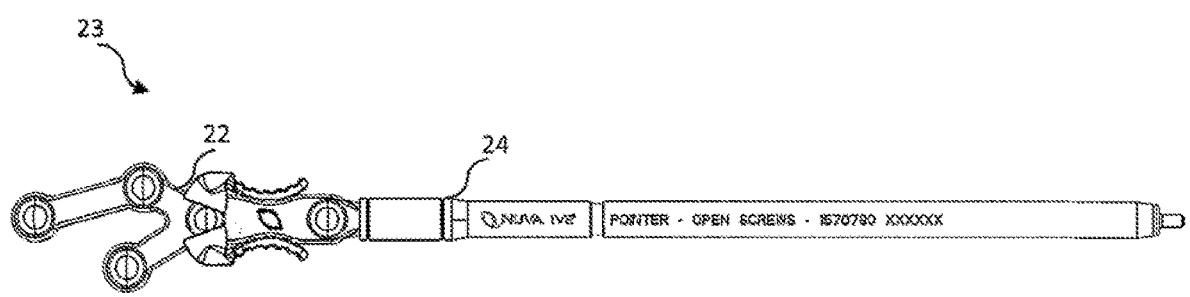
FIG. 5 is a front view of one embodiment of a digitizer pointer assembly comprising part of the system of FIG. 1.
Figure 6:
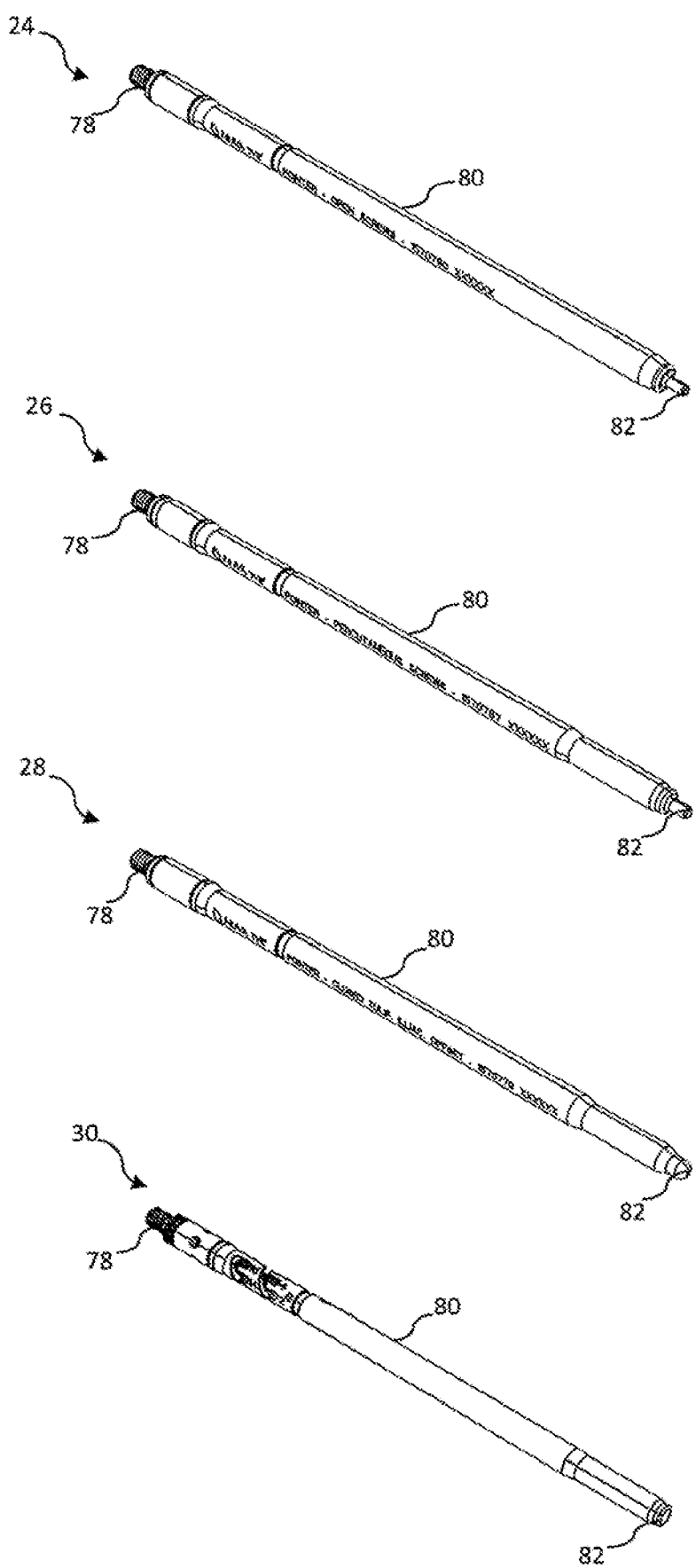
FIG. 6 is a perspective view of various surgical pointers compatible with the digitizer array of FIG. 2.

As depicted in FIG. 5, the IR-reflective tracking array 22 mates with one or more surgical objects (for example styluses 24, 26, 28, 30). Each stylus 24, 26, 28, 30 includes a threaded proximal end 78 for mating with the threaded distal aperture 56 of the IR-reflective tracking array 22, elongate shaft 80, and shaped distal tip 82. Shaped distal tip 82 may be any shape that is complimentary to, and fits securely within, the shape of a particular screw head. For example, FIG. 6 shows styluses 24, 26, 28, and 30 each with a different shaped distal tip designed to mate with different open screw systems, minimally-invasive screw systems, and closed tulip, iliac, and offset connector systems. The distal tip 82 is preferably inserted into each screw while orienting the digitizer pointer coaxial to that screw (or other fixation device).

According to some implementations (for example, the implementations shown with respect to styluses 24, 26, and 28), the length of the elongate shaft 80 is fixed relative to the array 22 such that all digitized points are a consistent length from the geometry of the IR-reflective markers 38 and position information may be obtained from this relationship. According to other implementations (for example, the implementation shown with respect to offset pointer 30), the length of the elongate shaft 80 is adjustable relative to the array 22 such as that shown with stylus 30, effectively elongating the distance from the digitized point and the IR-reflective markers. This longer distance translates to digitization of a point above the actual screw head based on the distance the user adjusted the elongate shaft 80. As will be appreciated in conjunction with the discussion below, the resulting bend instructions would shape a rod that traverses that point above the screw allowing the user to reduce the screw to the rod.

Figure 7:
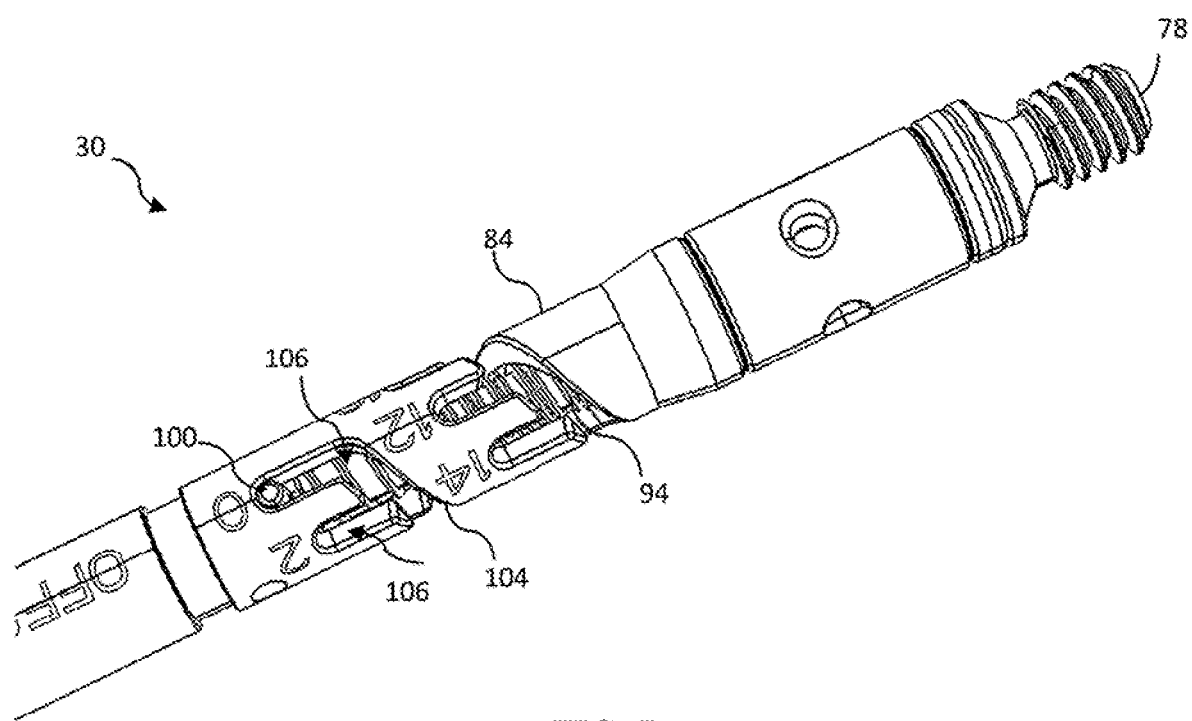
FIG. 7 is a partial perspective view of the offset pointer of FIG. 6 in a collapsed position.
Figure 8:
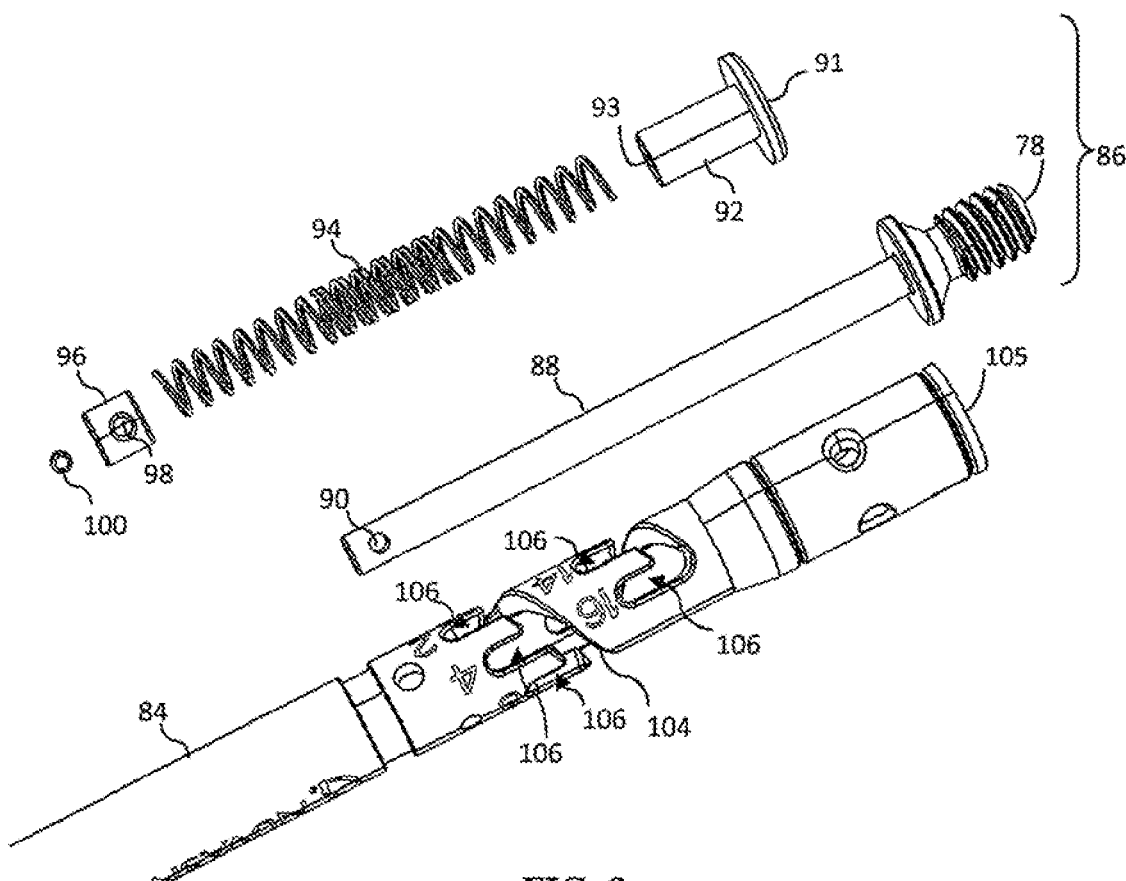
FIG. 8 is a partial exploded view of the offset pointer of FIG. 6.
Figure 9:
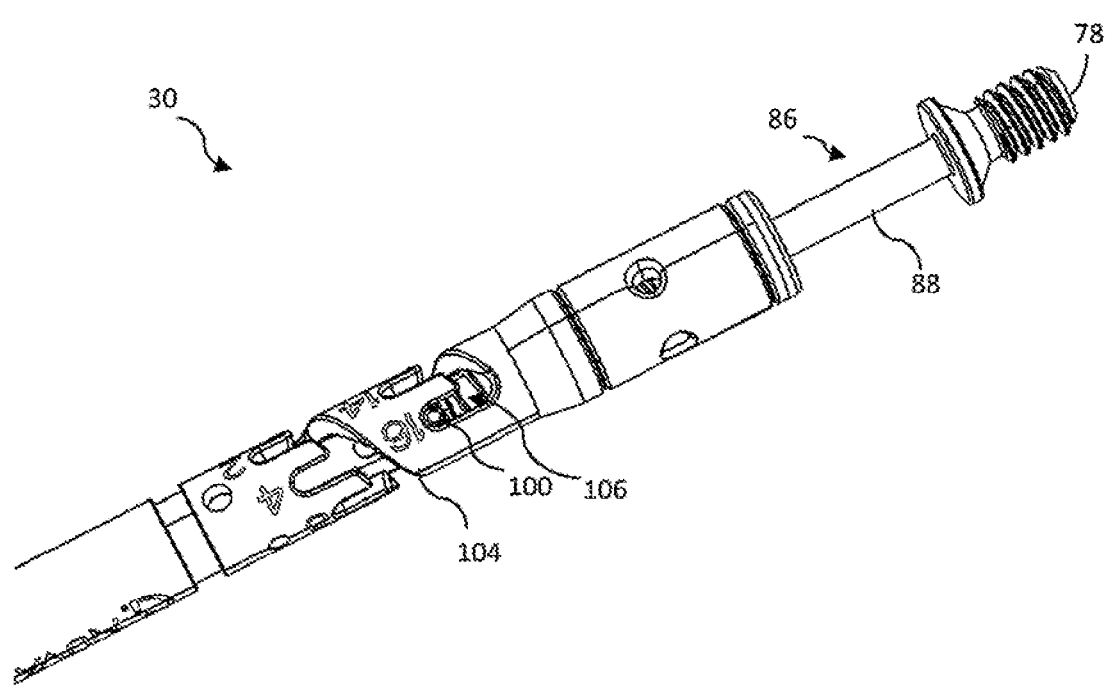
FIG. 9 is a partial perspective view of the offset pointer of FIG. 6 in an extended position.

As shown in FIGS. 6-8, offset pointer 30 includes an elongate tubular member 84 and an inner piston 86. Elongate tubular member 84 is comprised of a milled helical slot 104 and a plurality of offset depth slots 106 located around the helix that correspond to a plurality of offset distances as will be described below. Inner piston 86 includes shaft 88, T-shaped cap 92, springs 94, and bushing 96. The T-shaped cap 92 is positioned over the proximal end of the shaft 88 and is preferably welded to the proximal end 105 of the elongate tubular member 84. Springs 94 are slideably positioned along the length of the shaft 88 between the distal end 93 of the T-shaped cap 92 and bushing 96. Bushing 96 is positioned over the distal end of the shaft 88. Pin 100 is travels through, and protrudes laterally from, slots 90, 98 on the inner shaft 88 and bushing 96, thereby securing the bushing 96 to the inner shaft 88. The pin 100 is sized and dimensioned such that it travels through the helical slot 104 and be positioned within each of the offset depth slots 106.

The offset pointer 30 gives the user the ability to execute planned screw movement by a specific, pre-determined amount. The user inserts the offset pointer 30 into the screw head. Keeping the distal tip 82 engaged to the screw head, the user then selects an offset amount to be added to the screw and angles the offset pointer 30 in the direction he or she wishes to apply the offset to. To adjust between offset depth slots 106, the shaft 88 is pulled away from the array 22 and twisted until the pin 100 falls into the desired offset slot 106. As the shaft 88 is pulled, it telescopes in and out of the elongate tubular member 84 such that the distance between the shaped distal end 82 and the array 22 is increased. For purposes of illustration, FIG. 8 shows the offset pointer 30 with the pin 100 in the 16 mm offset slot 106 corresponding to a 16 mm offset between the pointer 30 length and the IR-reflective array 22. Offset options for sagittal correction may be provided, by way of example only from 0 mm to 16 mm offsets in 2 mm increments. The system 10 will then acquire position information at that point in space as opposed to where the screw sits, allowing for sagittal correction of one or more vertebral levels.

The digitizer pointer 23 may be used to acquire positional information about some or all screw locations. According to a preferred embodiment, the shaped distal tip 82 is coaxially aligned into the screw head and the array 22 is triggered to register the screw point. Screw locations may be digitized in a superior-inferior or inferior-superior direction. According to some implementations, the first screw location digitized correlates to the rod insertion direction component of the bend instructions (described below). Squeezing handles 66 activates the spring mechanism and permits the shutters 36 to open equally via the interdigitating gear teeth 72 (FIG. 4). Opening the shutter covers 68 exposes the middle IR-reflective sphere 38 and allows the IR tracking array 22 to be "seen" by the IR position sensor 20 and the position of the digitizer pointer 23 to be digitized. In this way, the IR position sensor 20 only recognizes the digitizer pointer 23 once the middle sphere 38 is exposed which allows for point-by-point tracking and obviates the sensing and digitization of one or more unnecessary data points which may occur with prior art systems that continually track surgical objects. Further, use of the gear mechanism allows the passive IR-reflective sphere 38 to be "seen" symmetrically by the IR position sensor 20, thereby enabling a more accurate calculation of position information by the system 10. According to some implementations, the control unit 16 emits an audible sound to notify the user that the middle sphere 38 is recognized by the IR position sensor 20 and the screw point is acquired. Once a point has been registered, the shutter handles 66 may be released, thereby closing the bilateral shutters 36. This process is then repeated for all screw locations to be digitized.

In accordance with the present invention, there are provided a plurality of algorithms for achieving rod bends. The surgical bending algorithms may be divided into two smaller sub-systems: (1) the spatial location algorithms that acquire, collect, and digitize points in space and (2) the bending algorithms that analyze the points and calculate the bend instructions and rod length needed to bend a rod with the mechanical bending device 18.

Figure 10:
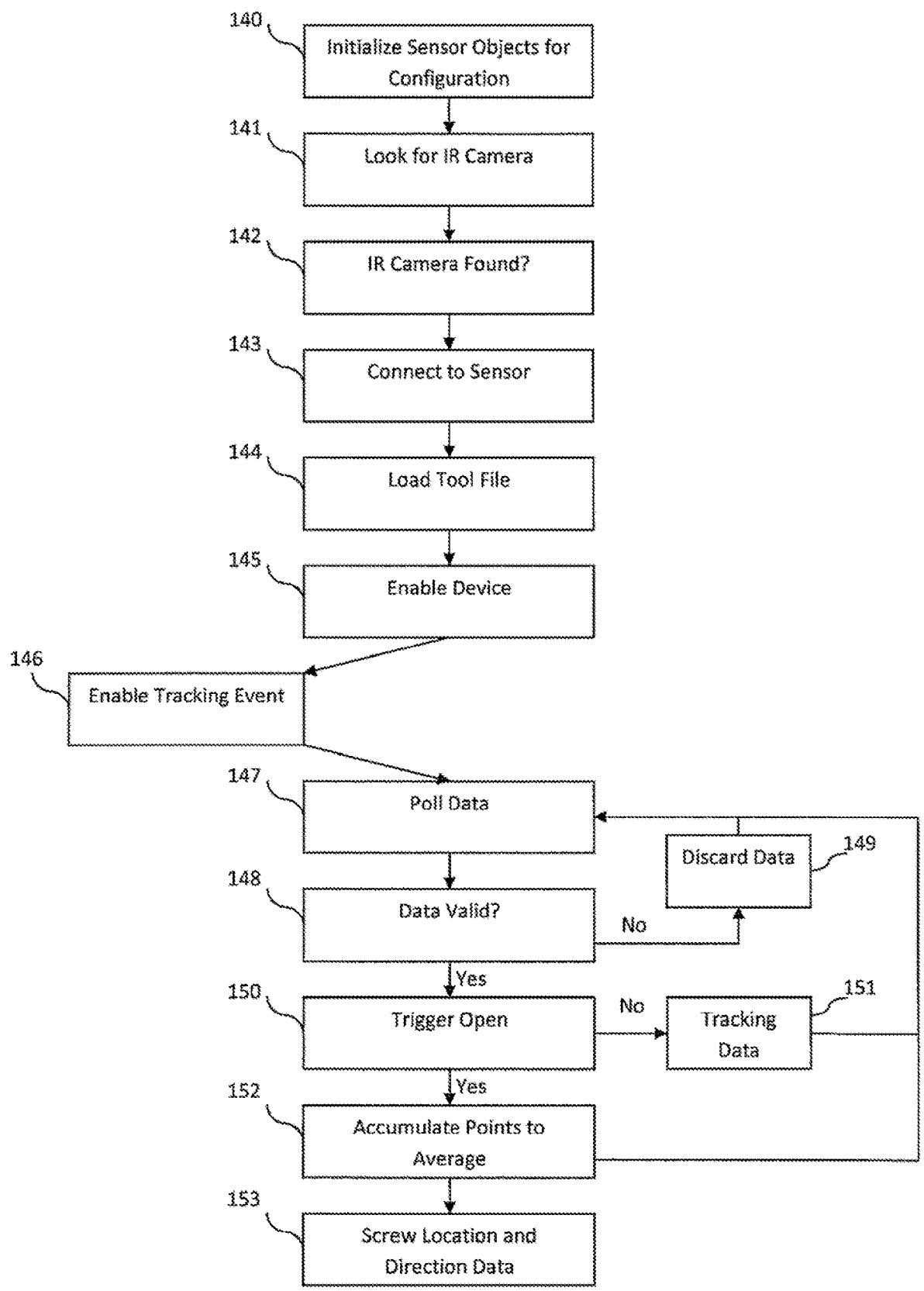
FIG. 10 is a flowchart depicting the steps of the spatial tracking algorithm according to one embodiment.

As set forth above, the spatial tracking system 12 measures the six degrees of freedom (6 DOF) information for the tracked IR-reflective spheres 38. These data provide the full pose (position and orientation) of each screw of interest which may then be made available to the algorithm library to calculate the bend instructions. FIG. 10 is a flow chart indicating the steps of the spatial location data acquisition process according to one embodiment. The system 10 initializes the sensor objects from configuration to connect to, control, and read data from the IR position sensor 20 (step 140). The system 10 then inspects all devices connected to it and finds the device with a device ID that corresponds to the IR position sensor 20 (step 141). At step 142, if an IR position sensor 20 is found at step 141, the system 10 continues to establish a connection with the IR position sensor 20 (step 143). However, if not the system 10 continues to search. After the system 10 connects to the IR sensor 20, it then loads a tool file that defines the array 22 (step 144). After initialization and tool file loading, the IR sensor 20 must prepare for taking data. At step 145, the IR sensor 20 is enabled and ready to generate positional data but is left idle until tracking is enabled. By way of example and as described with reference to FIG. 17, selecting the position of the IR sensor 20 with respect to the patient's body causes the control unit 16 to send the IR sensor 20 a command to begin tracking. With tracking enabled (step 146), the IR sensor 20 may be polled to for data (step 147). Preferably, new data is requested twenty times per second from the IR sensor 20. At step 148, the data generated from polling the IR sensor 20 is checked to ensure that it is reporting valid data. The data may be considered valid if all of the IR-reflective spheres 38 are visible to the IR sensor 20, the digitizer pointer 23 is fully inside the IR sensor's 20 working volume, there is no interference between the IR sensor 20 and the digitizer pointer 23, and both the location and rotation information reported are not null. At step 149, if the data is not deemed valid, then the digitized point is not used by the system 10 and polling is resumed. If the fifth IR-reflective sphere 38 (i.e. the middle sphere) is visible on the digitizer pointer 23 (step 150), the process of collecting positional data for the bend algorithm commences. If the middle sphere 38 is not visible, then the data is available to the system 10 only to show proximity of the IR sensor 20 and IR-reflective tracking array 22 (step 151). Points used by the bend algorithm are preferably an average of several raw elements (step 152). Normally, five points are collected at this step before the points are processed and made available to the bend algorithm. The position data is averaged using a mean calculation. The directions are averaged in the quaternion representation (raw form) then converted to a unit direction vector. The data is rotated from the spatial tracking system 12 coordinate from into the system 10 coordinate frame using a rotation matrix. At step 153, after all processing, the data is available for the bend algorithm to collect and process further as will be described in greater detail below.

Figure 11:
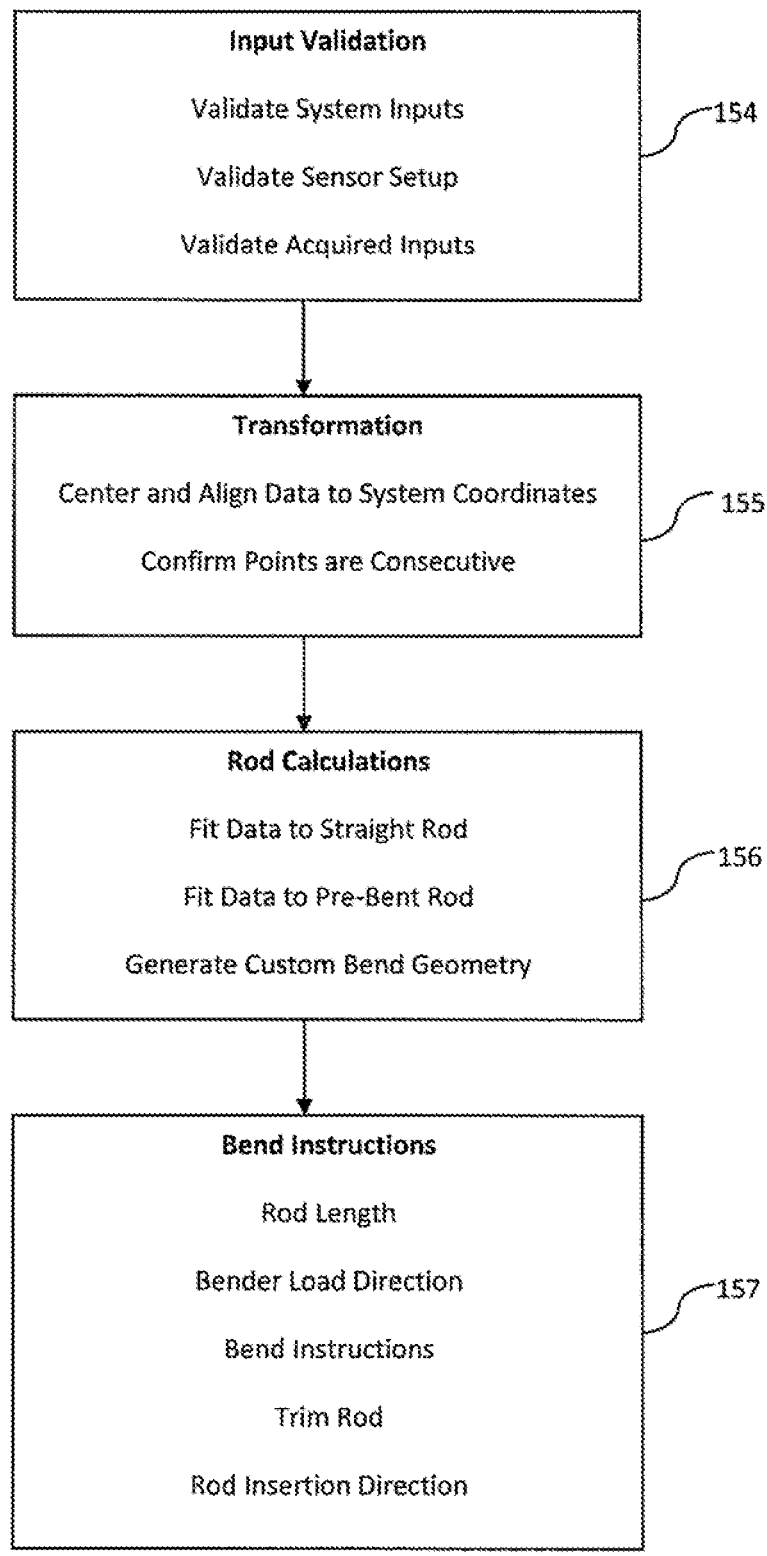
FIG. 11 is a flowchart depicting the rod bending workflow according to one embodiment.

The surgical bending software takes the location and direction data of the screw locations as described above and uses one or more geometry-based algorithms to convert these relative screw locations into a series of bend instructions. FIG. 11 is a flow chart indicating the steps of the surgical bending process according to a first embodiment. At the input validation step 154, the system 10 may validate the system inputs to ensure the rod overhang is greater than zero, validate the sensor setup to ensure that the IR sensor 20 location has been set, and validate each of the acquired points. By way of the example, the validation of each of the acquired points ensures, for example, that there are at least two screw points digitized, no two screw locations are too far apart, no two screw locations are too close together, and the span between the superior-most and inferior-most screw locations is not longer than the longest available rod.

At the transformation step 155, the data may be centered and aligned such that the first data point acquired is set at the system 10 coordinate's origin and all data is aligned to the x-axis of the system's coordinates thereby reducing any potential misalignment of the IR sensor 20 relative to the patient's spine.

At the rod calculations step 156, the system 10 may perform rod calculations for a straight rod solution, a pre-bent rod solution, and a custom-bend solution. For a straight rod solution, the system 10 first determines the length of a straight rod that will span all of the screw locations. This length may be calculated to accommodate each of the screw heads, hex and nose lengths of the rods chosen, and the user's selected rod overhang length. The system 10 then fits the data to a straight line, if the screw data is within tolerance of the straight line, then the bend instructions will return a straight rod, otherwise it will return no rod solution and proceed to look for a pre-bent rod solution. By way of example only, the tolerance may be 2 mm in each of the sagittal and coronal planes.

For a pre-bent rod solution, the system 10 first determines the length of the shortest pre-bent rod from the available rod from the available rods (as will be described in greater detail below) that will span all of the screw locations. This length may be calculated to accommodate each of the screw heads, hex and nose lengths of the rods chosen, and the user's selected rod overhang length. Next, the system 10 fits the digitized screw data to a circular arc in 3-dimensional space. If the screw data is within the tolerance of the arc, then the bend instructions will return a pre-bent rod solution, otherwise it will return no rod solution and proceed to look for a custom-bend rod solution. By way of example, this tolerance may be 2 mm in each of the sagittal and coronal planes.

Figure 12:
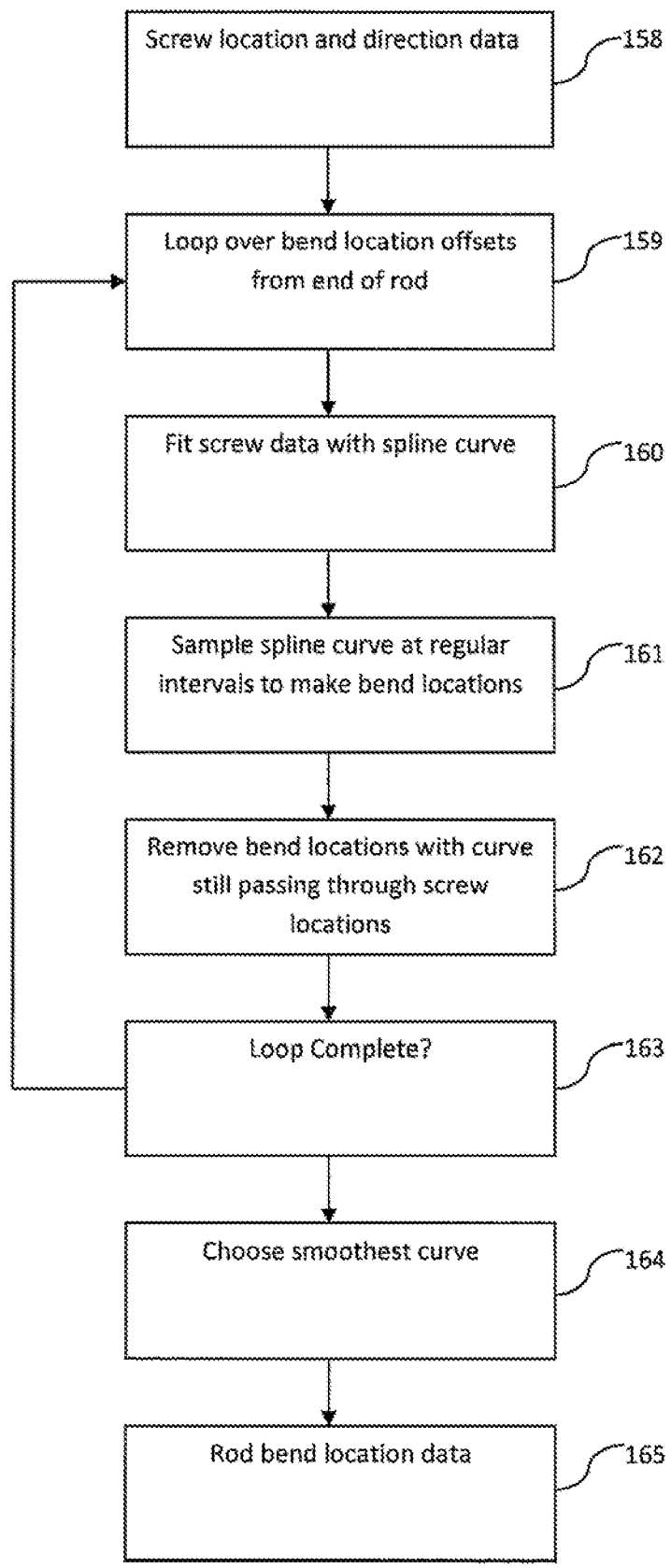
FIG. 12 is a flowchart depicting the steps in generating a rod solution according to a first embodiment.

FIG. 12 depicts a flow chart of a custom bend algorithm according to one embodiment. At step 158, screw location and direction data is generated by the spatial tracking system 12 as set forth above. The data is then projected into two planes: the x-y plane (coronal view) and the x-z plane (sagittal view). Each projection is then handled as a 2D data set. At step 159, a fixed size loop is generated over small incremental offsets for the first bend location for the end of the rod which optimizes the ability of the bend reduction step 162 to make smooth solutions. At step 160, the system 10 creates a spline node at each screw location and makes a piecewise continuous $4^{th}$ order polynomial curve (cubic spline) through the screw points. At step 161, the smooth, continuous spline is sampled at a regular interval (e.g., every 1 cm) along the curve to generate an initial set of proposed bend locations. At step 162, as many bends as possible are removed from the initial set of proposed bend locations from step 161 as possible to reduce the number of bends the user must execute on a rod in order to fit it into a screw at each digitized screw point. According to one embodiment, no bend is removed if eliminating it would: (1) cause the path of the bent rod to deviate more than a predefined tolerance limit; (2) cause any of the bend angles to exceed the maximum desired bend angle; and (3) cause the rod-to-screw intersection angle to exceed the maximum angulation of the screw head. Once the number of bends has been reduced, the 2D data sets are combined and handled as a 3D data set. The 3D line segments are then evaluated based on distance between each line segment interaction (Location), the angle between two line segments (Bend Angle), and the rotation (Rotation) needed to orient the bend into the next bend plane using the following calculations:

Location: $((X_2-X_1)^2+(Y_2-Y_1)^2+(Z_2-Z_1)^2)^{1/2}$

Bend Angle: arc-cosine($V_{12} \cdot V_{23}$)

where • is the dot product and V is a vector between 2 points

Rotation: arc-cosine($N_{123} \cdot N_{234}$)

where • is the dot product and N is the normal vector to a plane containing 3 points.

These calculated numbers are then tabulated to the physical design of the rod bender 18 and the selected rod material and diameter. Bend angles account for the mechanical rod bender's 18 tolerance and will account for the rod's material and diameter based on previous calibration testing performed with mechanical rod bender 18 and the specific kind of rod. Calibration testing quantifies the amount of spring-back that is expected when bending a certain rod material and diameter. By way of illustration, a 5.5 mm diameter titanium rod's spring-back can be characterized by a $1^{st}$ order linear equation:

$$BA_A = 0.94 * BA_T - 5.66$$

where $BA_T$ is the theoretical bend angle needed that was calculated from the 3D line segment and $BA_A$ is the actual bend angle needed to bend the rod to so it can spring back to the theoretical bend angle. Thus, using this equation, when 20 degrees of bend is calculated from the 3D line segment above, the "spring-back" equation for that rod will formulate that a 25 degree bend needs to be executed in order for it to spring-back to 20 degrees. The length of the final rod is the total of all the calculated distances plus the selected rod overhang.

Once all of the rod solutions have been generated, the loop is completed (step 163). At step 164, from all of the rod solutions generated in the loop above, the system 10 may output the rod solution having the smallest maximum bend angle (i.e., the smoothest bent rod). It is to be appreciated that the system 10 may choose the rod solution displayed based on any number of other criteria. At step 169, the system 10 then generates the three-dimensional locations of the bends in space.

Referring back to the flow chart of FIG. 11, from the geometric bend locations and/or pre-bent rod output of the rod calculations step 156 above, the system 10 generates instructions for the user to choose a straight rod, a pre-bent rod, or to custom bend a rod (step 157). All of the output instructions are human-readable strings or characters. In all cases, the length of the required rod is calculated as described above and is displayed to the user as either a cut rod or standard rod. For custom bend solutions, rods are loaded into the bender with the "inserter end" (e.g., one pre-determined end of the rod) into the bender collet 126. If, due to geometric constraints, the rod cannot be bent from the inserter end, then the instructions are flipped, and the cut (or nose) end of the rod is instructed to be put into the bender collet 126. The bend instructions are generated from the geometric bend locations and are given as "Location", "Rotation", and "Bend" values as will be described in greater detail below. These values correspond to marks on the mechanical bender 18.

Figure 13:
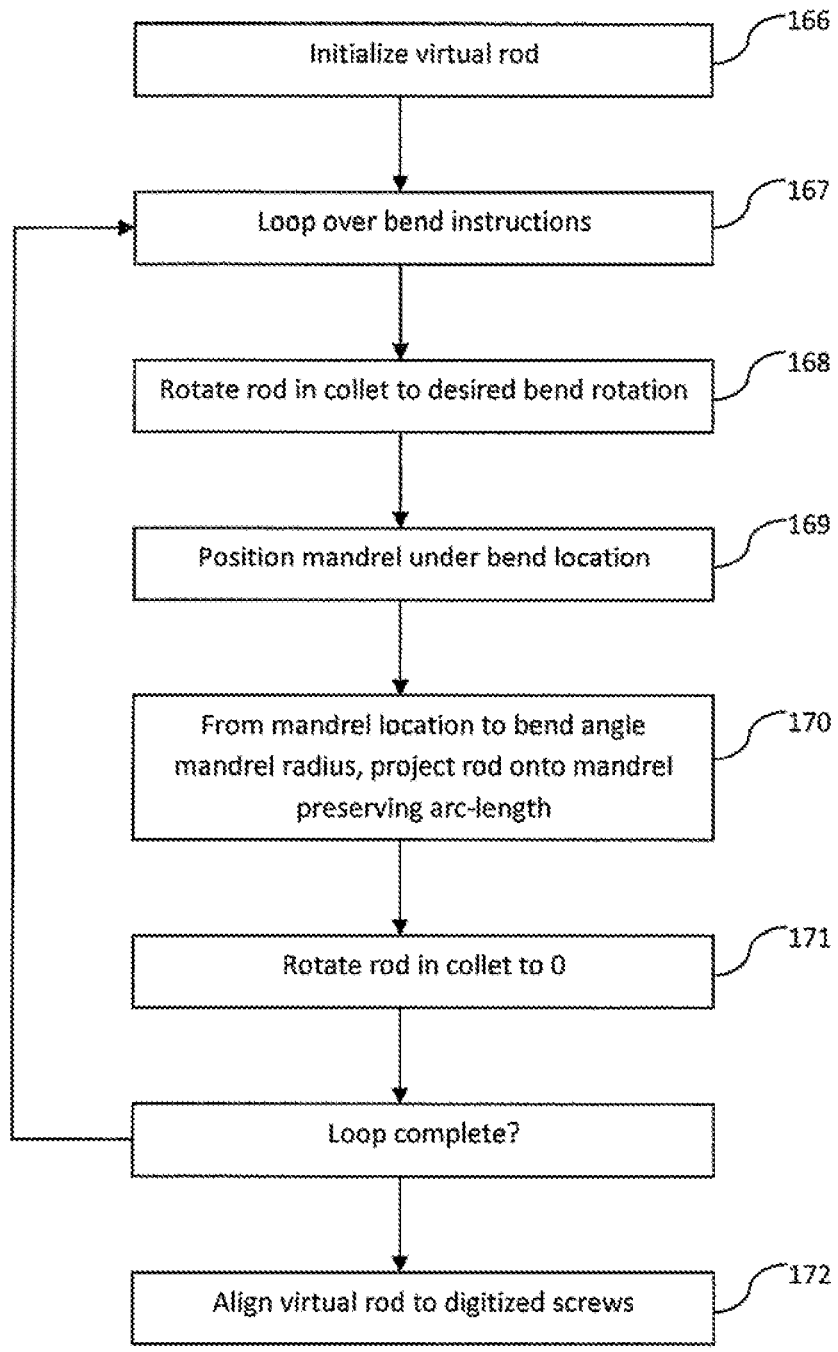
FIG. 13 is a flowchart depicting the steps in generating a rod solution according to a second embodiment.
Figure 14:
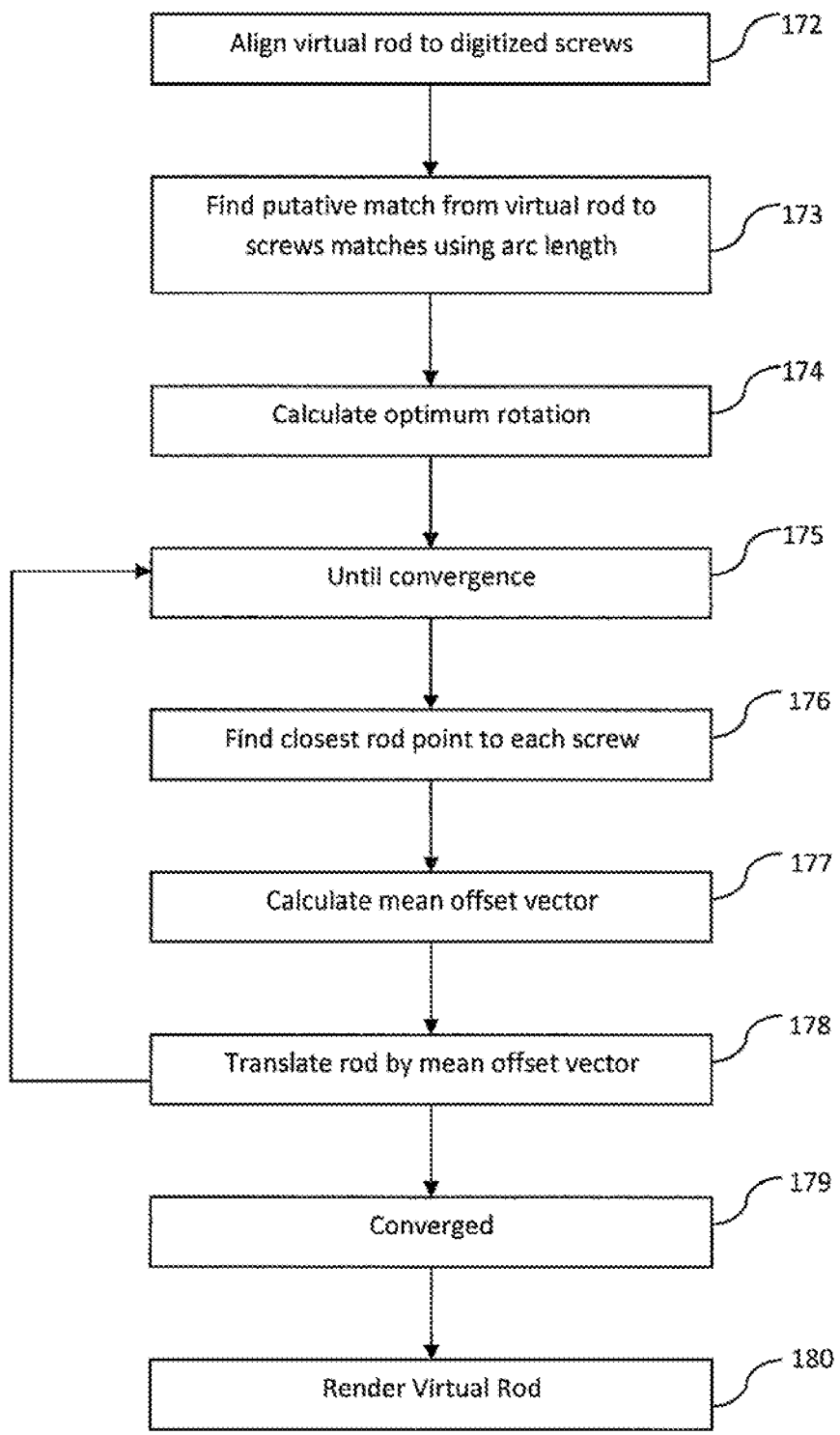
FIG. 14 is a flowchart depicting the steps in generating a rod solution according to a third embodiment.

FIGS. 13-14 depict a flow chart of a second embodiment of a custom bend algorithm. In accordance with this second embodiment, the custom bend algorithm includes a virtual bender used to render a virtual rod. The following calculations and the flowcharts of FIGS. 13-14 highlight the steps of this embodiment.

The 3D vector $s_i = [s_i^x, s_i^y, s_i^z]^T$ denotes the $i'^{th}$ screw digitized by the user such that the set of N acquired screws that defines a rod construct may be denoted as $$S = [s_0, \ldots, s_{N-1}] \in \mathbb{R}^{3 \times N} \tag{1}$$

It may be assumed that the screws have been collected in order (e.g. superior-most screw to inferior-most screw or inferior-most screw to superior-most screw) so the index i can also be thought of as the index through time.

A virtual rod (R) of length $L_r$ given in mm is broken down into Nr uniformly distributed points, $R = [r_0, \ldots, r_{Nr-1}]$. Each rod point $r_i$ is composed of two components, a spatial component and a directional component $r_i = \{r_i^s, r_i^d\}$, where $r_i^s, r_i^d \in \mathbb{R}^3$. The segments between rod points is constant and defined by $$\delta_i = |r_{i+1}^s - r_i^s|. \text{ Let } \Delta_d = \Sigma_{i=0}^d \delta_i, \text{ then } \Delta_{Nr-1} = L_r.$$

A virtual bender (B) consists of a mandrel (M) of radius $M_r$ (mm). Preferably, though not necessary, the key assumption when bending the virtual rod around M is the conservation of arc length. For illustrative purposes only, if a 90° bend is introduced to an example rod R of length 100 mm around a mandrel with radius 10 mm to produce a rod $\hat{R}$, then $$\int dR = \int d\hat{R} \tag{2}.$$

The virtual rod, R, is bent according to a list of instructions. Each instruction consists of a location ($I_l$), rotation ($I_r$), and bend angle ($I_\theta$). The location is the position of the rod in the bender and corresponds to the point directly under the mandrel M. The rotation is given in degrees (0°-360°) and corresponds to the amount the rod is rotated from 0 in the collet. The bend angle is given by a single letter that corresponds to a specific angle in degrees. There is a corresponding notch on the bender with the same letter for the user to select.

The rod is initialized (step 166) such that the spatial component $r_i^s = [\Delta_i, 0, 0]^T|_{i=0}^{N_r-1}$, and the direction component $r_i^d = [0, 1, 0]^T|_{i=0}^{N_r-1}$ which effectively orients the virtual rod to be at zero rotation in the virtual bender. For each bend instruction (step 167), the system 10 rotates the virtual rod around the x-axis by $I_r$ (step 168). The system 10 finds the point $\hat{r}_i$ that matches $I_l$. The virtual rod is translated by $-\hat{r}_i$. Next, each rod point from i to i+$M_r$*$I_\theta$ is projected onto the mandrel M while preserving segment length (step 169-170). The virtual rod is then rotated around the x-axis by angle $-I_r$. Next, the system 10 checks that $r_0^d = [0, 1, 0]^T$ to verify that the virtual rod in the collet has the correct direction vector (step 171). At this point, R has approximated the geometry of the rod as it would be bent in the physical mechanical bender 18.

The next step is to align the bent virtual rod to the acquired screw positions (step 172). According to one embodiment, the alignment process has two stages—first, the system 100 finds the optimum rotation coarse scale (step 174). Second, the system performs the iterative closest point iteration algorithm fine scale.

Preferably, the system first initializes the result close to a global minimum (step 173). In the rod alignment algorithm, this initialization follows the approach described below:

Using the arc length of the custom rod and the arc length of the screws, putative matches from the screws to the rod are produced. This produces two 3D point sets of equal size. Given two 3D mean centered point sets $\Sigma = [\sigma_0, \ldots, \sigma_{N-1}]$ and $\Gamma = [\gamma_0, \ldots, \gamma_{N-1}]$, then in the least squares sense, it is desirable to minimize $$E = \frac{1}{N} \sum_{i=0}^{N-1} (\sigma_i - T\gamma_i)^T (\sigma_i - T\gamma_i) \tag{3}$$

Where T denotes the rotation matrix. Let $\hat{T}$ denote the optimum 3D rotation matrix, then $$\hat{T} = \operatorname*{argmin}_T \frac{1}{N} \sum_{i=0}^{N-1} (\sigma_i - T\gamma_i)^T (\sigma_i - T\gamma_i) \tag{4}$$

It turns out that $\hat{T} = UV^T$, where (step 174)

$$C = SVD(H) = U\Sigma V^T \text{ and} \tag{5}$$

$$H = \frac{1}{N} \sum_{i=0}^{N-1} \sigma_i^T \gamma_i. \tag{6}$$

Due to error potentially introduced by differences in arc length, the proposed solution may not be the global minimum. Thus, the following are repeated until convergence (step 175):

For each $s_i$, find the closest $r_j$ (step 176)
Calculate the residual vector $e_i = s_i - r_j$
Calculate the average residual vector $$\hat{e} = \frac{1}{N} \sum_{i=1}^{N-1} e_i \quad \text{(step 177)}$$

Translate the rod by $\hat{e}$ (step 178)
Verify the error is reduced (step 179).

Next the virtual rod is rendered at step 180. The curve may be simplified for rendering purposes by traversing each triad of rod points and calculating the angle between the two vectors. If the first triad is $\{r_0, r_1, r2\}$, the two vectors are formed as $v = r_1 - r_0$ and $w = r_2 - r_0$. If $|v \times w| = 0$, then the middle point of the triad (in this case $r_1$) is redundant, provides no new information to the geometry of the rod and may be removed.

It will be appreciated that, in accordance with this embodiment of the rod bending algorithm, the virtual bender may be capable of bending a rod at any location of any angle perfectly to observe arc length. Using a virtually bent 3D rod to determine problem screws (i.e. screw locations with a high screw-rod fit error) may give an accurate fit between the actual screws and actual rod before the actual rod is bent. This may be particularly advantageous in certain surgical applications where it is desirable to quantify the amount of offset between a rod solution and the digitized screw locations as well as input one or more surgical parameters into the rod bending calculation.

In accordance with the present invention, there is described a third embodiment of an algorithm for generating a custom bend which may be utilized in conjunction with the second embodiment. The approach is directed to one or more algorithms that sample from probability distributions and employ random sampling to obtain a numerical result. A Markov chain is a sequence of random variables, $X_0, X_1 \ldots$, such that the current state, the future and past states are independent.

$$p(X_{n+1} = x | X_0 = x_0, X_1 = x_1, \ldots X_n = x_n) = p(X_{n+1} = x | X_n = x_n) \quad (1)$$

Given an ordered set of screws that define a construct $$S = [s_0, \ldots, s_{N-1}] \in \mathbb{R}^{3 \times N} \quad (2)$$

where $s_i = [s_i^x, s_i^y, s_i^z]^T$ denotes the $i^{th}$ 3D screw digitized by the user, the system 10 finds the set of bend instructions that define a rod that fits the screws in an optimum way defined by an error function. It is to be appreciated that the search of the bender space is quite complex as there are several constraints that must be observed for the algorithm to produce valid bend instructions (e.g., the bend locations cannot be in close proximity to the screws, the bend locations must be in multiples of 5 mm apart, the bend angles must be in multiples of 5°, no bend angle can be greater than 60°, etc.).

In accordance with the second embodiment, the likelihood or error function may be constructed based on how well the virtual rod fits the data. Here, the rod is fit to the data in the least squares sense. In this way, a likelihood function is defined that incorporates, for example, a prior to prefer fewer bend instructions:

$$L = \prod_{i=0}^{N_s-1} \frac{1}{\sigma_s \sqrt{\pi}} e^{\frac{-(x_i - v_i)^2}{\sigma_s^2}} e^{\frac{-N_b}{\alpha}}$$

$$= \left( \frac{1}{\sigma_s \sqrt{\pi}} \right)^{N_s} e^{\sum_{i=0}^{N_b-1} \frac{-(s_i - r_i)^2}{\sigma_s^2}} e^{\frac{-N_b}{\alpha}}$$

such that the log-likelihood function may be defined as $$\log(L) = -N_s \log(\sigma_s) - \sum_{i=0}^{N_e-1} \frac{-(s_i - r_i)^2}{\sigma_s^2} - \frac{-N_b}{a} \quad (3)$$

Where $N_b$ denotes the number of bends in the rod, $N_s$ denotes the number of screw locations, $s_i$ is the i'th screw, $r_i$ is the i'th rod point, and $\alpha$ is the control hyper-parameter for the number of bends (e.g. $\alpha = 0.05$).

As can be seen from equation (3), there has been introduced a prior to control the number of bends introduced into the rod. This probabilistic approach to bend instruction generation allows for tailoring of constraints, for instance, a prior on the severity of the bends could also be introduced. Further, a prior could be introduced on how to define how close to the screws the bends may be located. This prior may have a "preferred" value, but probabilistically, there may be an optimal solution away from this idealized value. By way of example, some hypothesized rules that may be applied to this algorithm include, but are not limited to: birth move: add a bend to the current solution; death move; remove a bend from the current solution; update move: translate rod points along the rod. Use of this embodiment may provide more potential rod solutions to the user.

Figure 15:
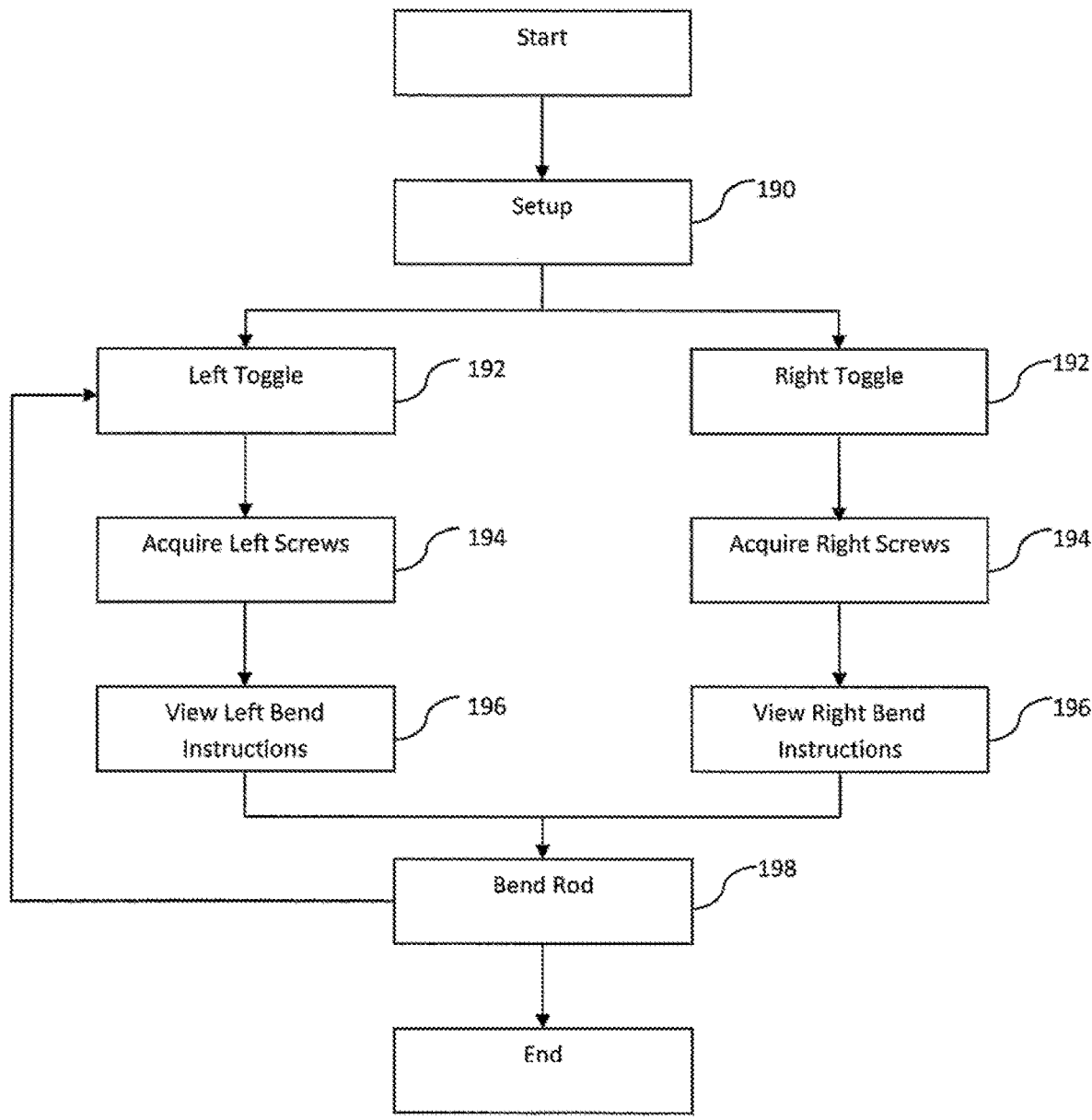
FIG. 15 is a flowchart depicting the steps of the rod bending process according to a first embodiment.

Details of the system 10 are now discussed in conjunction with a first embodiment of a method for obtaining a custom-fit rod. The system 10 is typically utilized at the end of a posterior or lateral fixation surgical procedure after screws, hooks or other instrumentation have been placed, but prior to rod insertion. As shown in the flowchart of FIG. 15, the system 10 obtains position information of the implanted screw positions and outputs bend instructions for a rod shaped to custom-fit within those implanted screws. At step 190, pertinent information is inputted into the system via a setup screen. At step 192, the user designates the side for which a rod will be created (patient's left or right side). At step 194, the system 10 digitizes the screw locations. At step 196, the system 10 outputs bend instructions. At step 198, the user bends the rod according to the bend instructions. Steps 190-198 may then be repeated for a rod on the contralateral side of the patient if desired.

Figure 16:
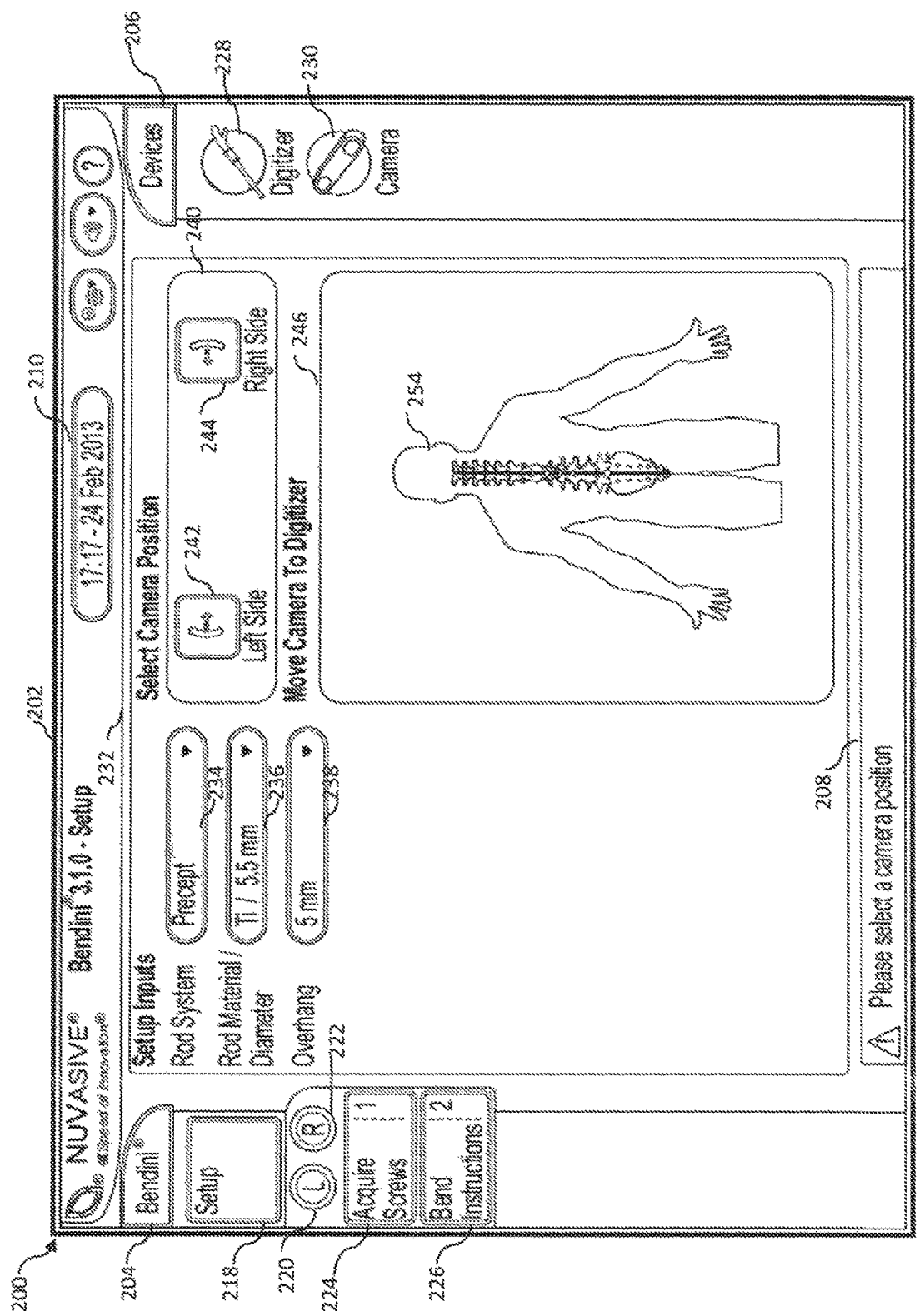
FIG. 16 is a screen shot depicting an example setup screen of the system of FIG. 1.

FIG. 16 illustrates, by way of example only, one embodiment of a screen display 200 of the control unit 16 capable of receiving input from a user in addition to communicating feedback information to the user. In this example (though it is not a necessity), a graphical user interface (GUI) is utilized to enter data directly from the screen display 200. As depicted in FIG. 16, the screen display 200 may contain a header bar 202, a navigation column 204, device column 206, and a message bar 208.

Header bar 202 may allow the user to view the date and time, alter settings, adjust the system volume, and obtain help information via date and time display 210, settings menu 212, volume menu 214, and help menu 216 respectively. Selecting the settings drop-down menu 212 allows the user to navigate to system, history, and shutdown buttons (not shown). For example, choosing the system button displays the rod bending software version and rod bender configuration file; choosing the shutdown option shuts down the rod bending software application as well as any other software application residing on the control unit 16 (e.g. a neuromonitoring software application); and choosing the history option allows the user to navigate to historical bend points/instruction data in previous system sessions as will be described in greater detail below. Selecting the help menu 216 navigates the user to the system user manual. As will be described in greater detail below, navigation column 204 contains various buttons (e.g., buttons 218, 220, 222, 224, 226) for navigation through various steps in the rod bending process. Pressing button 204 expands/minimizes the details of the navigation column. Devices column 206 contains various buttons indicating the status of one or more devices associated with the system 10. By way of example, devices column 206 may include buttons 228 and 230 for the digitizer 23 and IR sensor 20 components of the system 10, respectively. Pressing button 206 expands/minimizes the details of the devices column. Furthermore, pop-up message bar 208 communicates instructions, alerts, and system errors to the user.

Figure 17:
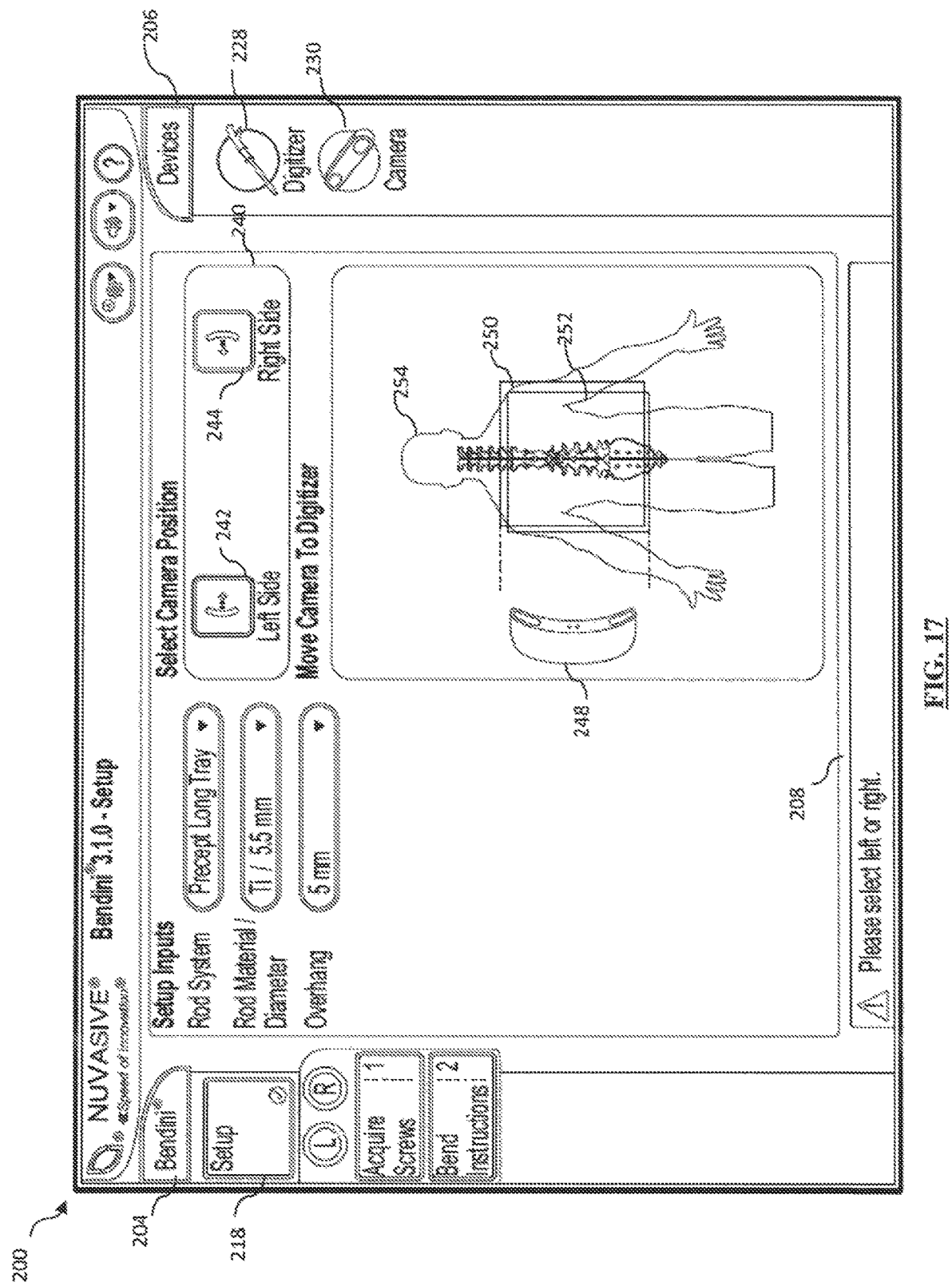
FIG. 17 is a screen shot depicting an example IR positioning sensor setup screen of the system of FIG. 1.

FIGS. 16-17 depict an example setup screen. Upon selecting setup button 218 on the display screen 200, the system 10 automatically initiates the setup procedure. The system 10 is configured to detect the connection status of each of its required components. By way of example only, icons 228, 230 indicate the connectivity and activity status of the digitizer 23 and IR sensor 20, respectively. If one or more required components are not connected or are connected improperly, the display 200 may alert the user to address the issue before proceeding via textual, audio, and/or visual means (e.g., textual messages, audible tones, colored icons or screens, blinking icons or screens, etc.). According to one embodiment, the digitizer icon 228 is a status indicator for the active acquisition and/or recognition of the digitizer and the presence and background color of the icon 228 may change to indicate the digitizer tracking status. By way of example, the icon 228 may be absent when the system 10 is not acquiring screws and does not recognize the digitizer, gray when the system 10 is not acquiring screws and recognizes the digitizer, green when the system 10 is in screw acquisition mode and recognizes the digitizer, and red when the system 10 is in screw acquisition mode and does not recognize the digitizer. Pressing button 206 expands/minimizes the details of the device column 206. Depending on the type of surgery, type of patient deformity, etc., it may be advantageous for the user to choose a digitizer from a selection of different digitizers. According to one embodiment, pressing icon 228 expands a pull-out window for the different stylus options available with the system 10 (e.g., styluses 22, 24, 26, 30 as described above). According to another embodiment, the IR sensor graphic icon 230 is a status indicator for the IR sensor 20. The presence and background color of the icon 230 may change to indicate the status of the IR sensor 20. By way of example, the icon 230 may be absent when the system 10 does not recognize the IR sensor 20, gray when the system 10 recognizes the IR sensor 20 is connected to the system 10, and red when the system 10 senses a communication or bump error for the IR sensor 20. Preferably, the IR sensor 20 should be recognized if it is connected after initialization of the bending application.

With all of the required components properly connected to the system 10, the user may then input one or more pieces of case-specific information from one or more drop-down menus. By way of example, drop-down menus for rod system 234, rod material/diameter 236, rod overhang 238, procedure type (not shown), and anatomical spinal levels of the surgical procedure) may be accessed from the setup selection panel 232 of the screen display 200. The rod system drop-down menu 234 allows the user to choose the rod system he/she plans to use. This selection drives choices for the rod material/diameter 236 drop-down menus. By way of example, under the rod system drop-down menu 234, the system 10 may be programmed with numerous fixation options from one or more manufacturers. Alternatively, it may be programmed with the fixation system selections for one manufacturer only (e.g. NuVasive® Precept®, Armada®, and SpherX® EXT). The user may also choose the combination of rod material (e.g. titanium, cobalt chrome, etc.) and rod diameter (e.g. 6.5 mm diameter, 5.5 mm diameter, 3.5 mm diameter, etc.). The drop-down menu 238 for material and diameter options may preferably be dependent upon the choice of rod system. Because the geometry and sizes can vary between manufacturers and/or rod systems, programming the system 10 with these specific inputs can aid in outputting even more accurate bend instructions. The user may also choose the amount of overhang from the rod overhang pull-down menu 238. By way of example, the amount of overhang may be selectable in 0 mm, 2.5 mm, 5 mm, 7.5 mm, and 10 mm lengths. According to one embodiment, this function prescribes a symmetric overhang on both the superior and inferior ends of the rod. According to another embodiment, this function also prescribes different overhang lengths on either end of the rod based on user preference and patient anatomical considerations. Although not shown, the system 10 also contains functionality for accommodating multiple rod diameters and transitional rods as used, for example in Occipital-Cervical-Thoracic (OCT) fusion procedures After the setup inputs have been inputted into the setup selection panel 232, the system 10 aids the user in setting up the IR sensor 20 in an optimal position for positional data acquisition. It is to be appreciated that any visual (textual, graphic) indicator may be used to indicate the IR sensor placement instructions. According to some implementations, an active graphic directs the user to position the IR sensor 20 relative to the digitizer array 22 held static within the patient's body. As shown in FIG. 17, the user first selects the side of the patient the IR sensor 20 is located on by selecting the left side sensor position button 242 or right side sensor position button 244 in the IR sensor setup panel 240. Choosing the left or right side sensor position button 242, 244 activates a the IR sensor positioning panel 246 such that sensor graphic 248 and a tracking volume box graphic 250 appear on the display screen 200. Tracking volume box 252 that moves with the sensor graphic 248 as the IR sensor 20 is moved. Next, the user positions the digitizer array 22 into the body of the patient. Once recognized by the system 10, a target volume box 252 (which may be displayed as white in color) is positioned over the patient graphic 254. Next, the user moves the IR sensor 20 relative to the digitizer array 22 until the tracking volume box 250 matches up to the position of the target volume box 252. According to some implementations, the sensor graphic 248 increases in size if it is moved superior to the target tracking volume and decreases in size if it is moved inferior to the target volume. According to some other implementations, the tracking volume box 250 may be color-coded to depict the relative distance to the target volume. By way of example, the tracking volume box 250 may be depicted in red if the distance to the target volume is outside of a certain distance in one or more axes (e.g., outside±8 cm in all 3 axes.) and green if within or equal to ±8 cm in all 3 axes. Once the optimal position of the IR sensor 20 has been ascertained, the setup process is complete.

Figure 18:
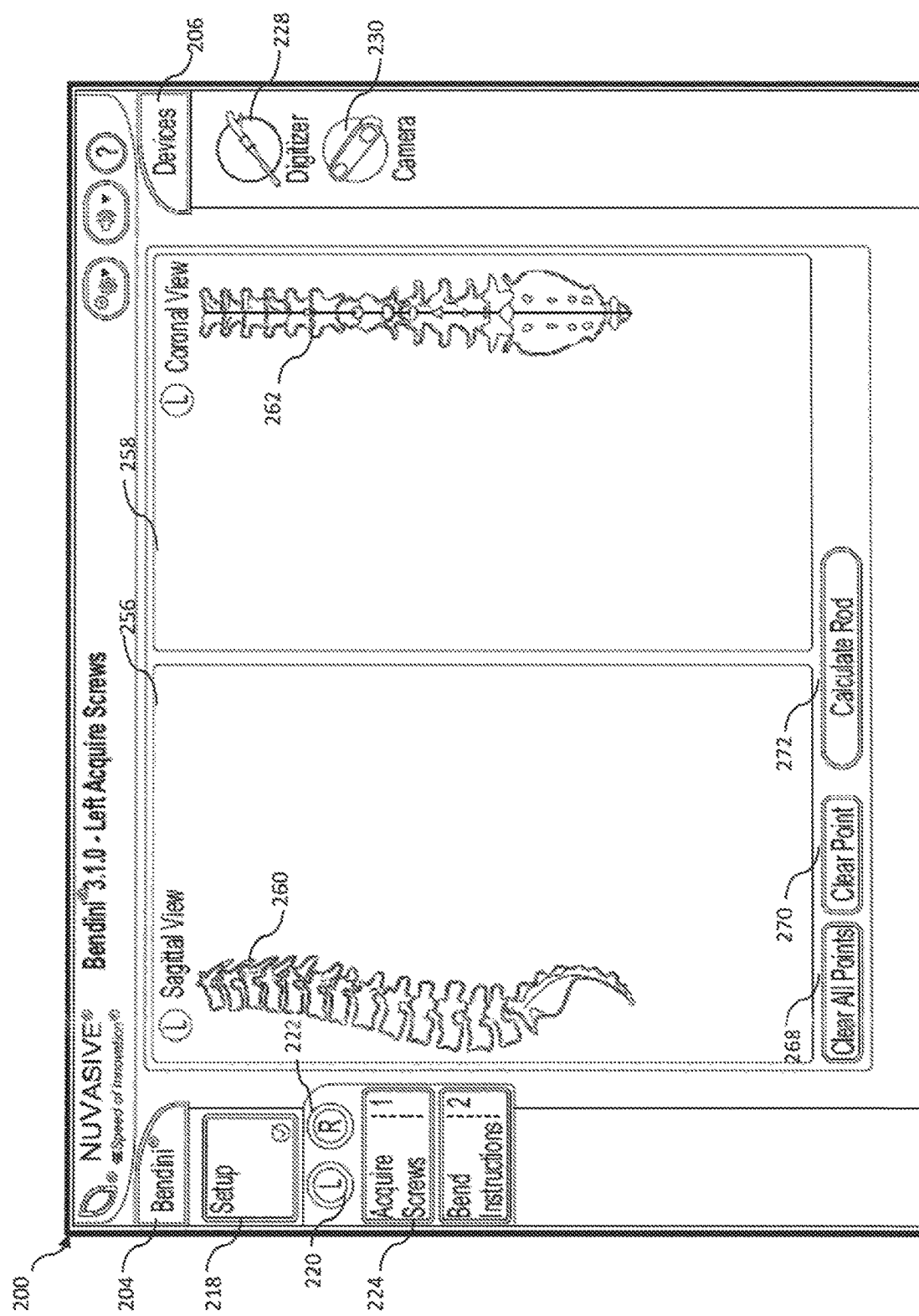
FIG. 18 is a screen shot depicting an example screw location digitization screen during a first step in the Acquire Screws step of FIG. 15.
Figure 19:
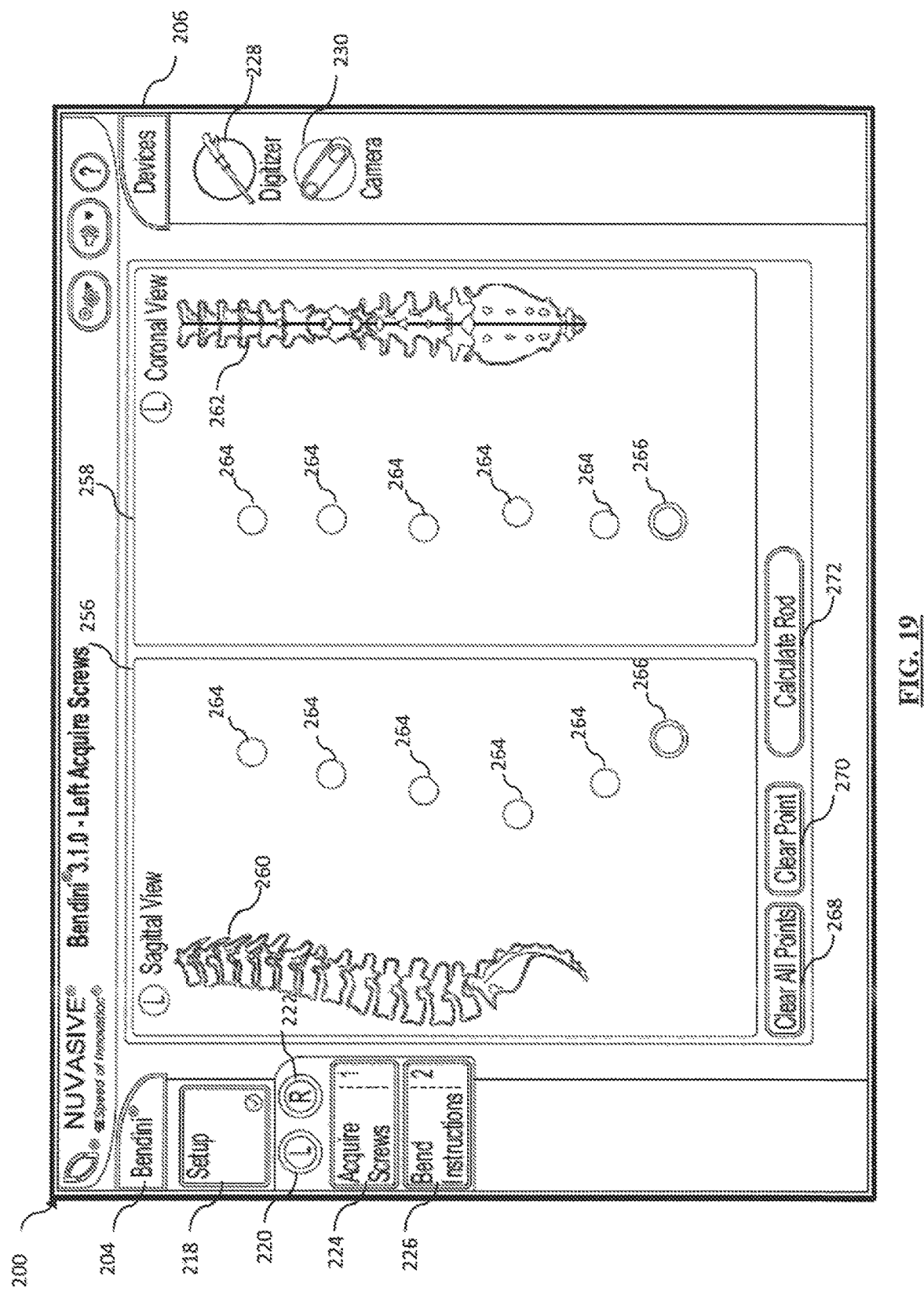
FIG. 19 is a screen shot depicting an example screw location digitization screen during a second step in the Acquire Screws step of FIG. 15.

Once the user has completed all of the required steps in the setup screen, a graphic (e.g., a check) may appear on setup button 218 to indicate such a completion and the system 10 proceeds to step 192 in the flowchart of FIG. 15. Using the GUI, the user designates which side of the patient's spine to acquire digitized positional information from by selecting either the Left "L" toggle/status button 220 or Right "R" toggle/status button 222. The user then selects the Acquire Screws button 224 which navigates the display screen 200 to an Acquire Screws (left or right) screen shown by way of example in FIGS. 18-20. In Acquire Screws mode, the display screen 200 includes a sagittal view panel 256 and a coronal view panel 258 with spine graphics 260, 262 in each of the sagittal and coronal views, respectively. Spine graphic 260 may flip orientation depending on which side of the spine the user is digitizing (left or right). Additionally, spine graphic 262 may highlight the side of the patient the user is digitizing (left or right). The user may digitize the location of each implanted screw using, by way of example, the digitizer pointer 23 as described above. As each screw point 264 is digitized, its relative location with respect to the other acquired screw points 264 can be viewed in both sagittal and coronal views via the sagittal view panel 256 and the coronal view panel 258 as shown in FIG. 19. Optionally, the last screw point digitized may have a different graphic 266 than the previously-acquired screw points 264 (by way of example, the last screw point acquired 266 may be a halo and the previously-acquired screw points 264 may be circles). The screws locations may be digitized from a superior-to-inferior or inferior-to-superior direction and according to some embodiments, the system 10 can detect which direction the digitization is occurring in after the acquisition of two consecutive screw point locations. If during the digitization process, the user wishes to delete a digitized screw point, he/she may do so by pressing the "Clear Point" button 270. If the user wishes to delete all digitized screw points, he/she may do so by pressing the "Clear All Points" button 268.

Once the digitized screw points 264 are deemed acceptable, the user may press the "Calculate Rod" button 272 which initiates the curve calculation preferably using one of the algorithms discussed above. Once a rod solution has been calculated, a rod graphic 274 populates through the screw points 264, 266 and a confirmation graphic (e.g., a check) may appear on the "Acquire Screws" button 224 to indicate that the system 10 has generated a rod solution. Simultaneously, the "Calculate Rod" button 272 becomes the "Undo Rod" button 272. If the user presses the "Undo Rod" button 272, the rod solution 274 is cleared and the user may acquire more screw points or clear one or more screw points. After the "Undo Rod" button 272 is pressed, it then changes back to the "Calculate Rod" button 272. Optionally, the system 10 may include a visual graphic for where along a rod the curve calculation is generating a severe bend (acute angle). The user may select "Undo Rod" button 272, perform one or more surgical maneuvers (e.g. reduce the screw, backup the screw, adjust the screw head, etc.), redigitize the screw point, and generate a more feasible solution. If the rod solution is acceptable to the user, the Screw Acquisition step 194 is complete and the system 10 proceeds the Bend Instructions step 196 in the flowchart of FIG. 15. Alternatively, although not shown the system 10 may display the offending point resulting in the severe bend angle in red and offer the next-best solution that includes a bend angle falling within a pre-determined range of angles for that bender. If the rod solution is acceptable to the user, the Screw Acquisition step 194 is complete and the system 10 proceeds the Bend Instructions step 196 in the flowchart of FIG. 15.

Figure 20:
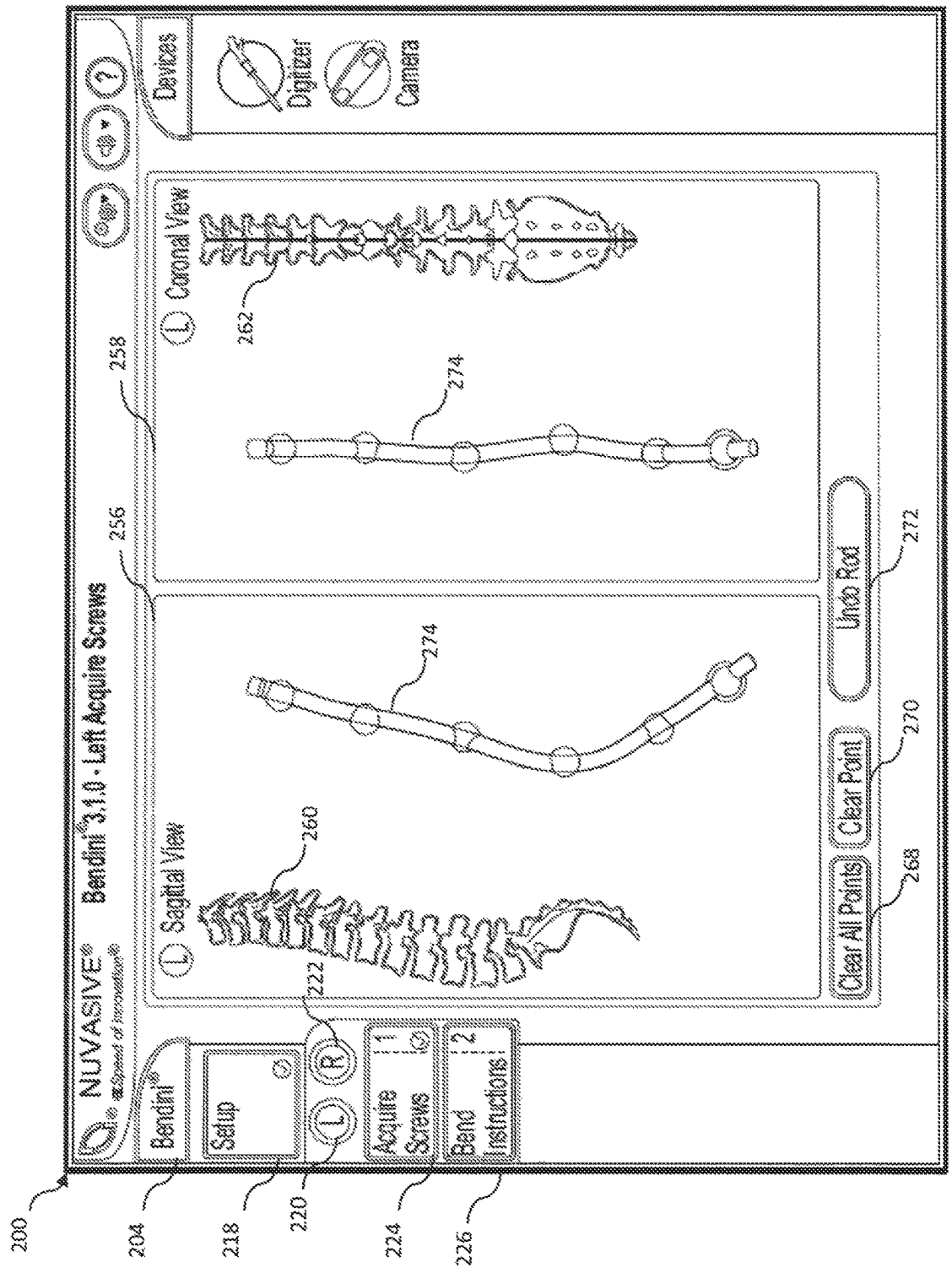
FIG. 20 is a screen shot depicting an example screw digitization screen during a third step in the Acquire Screws step of FIG. 15.
Figure 21:
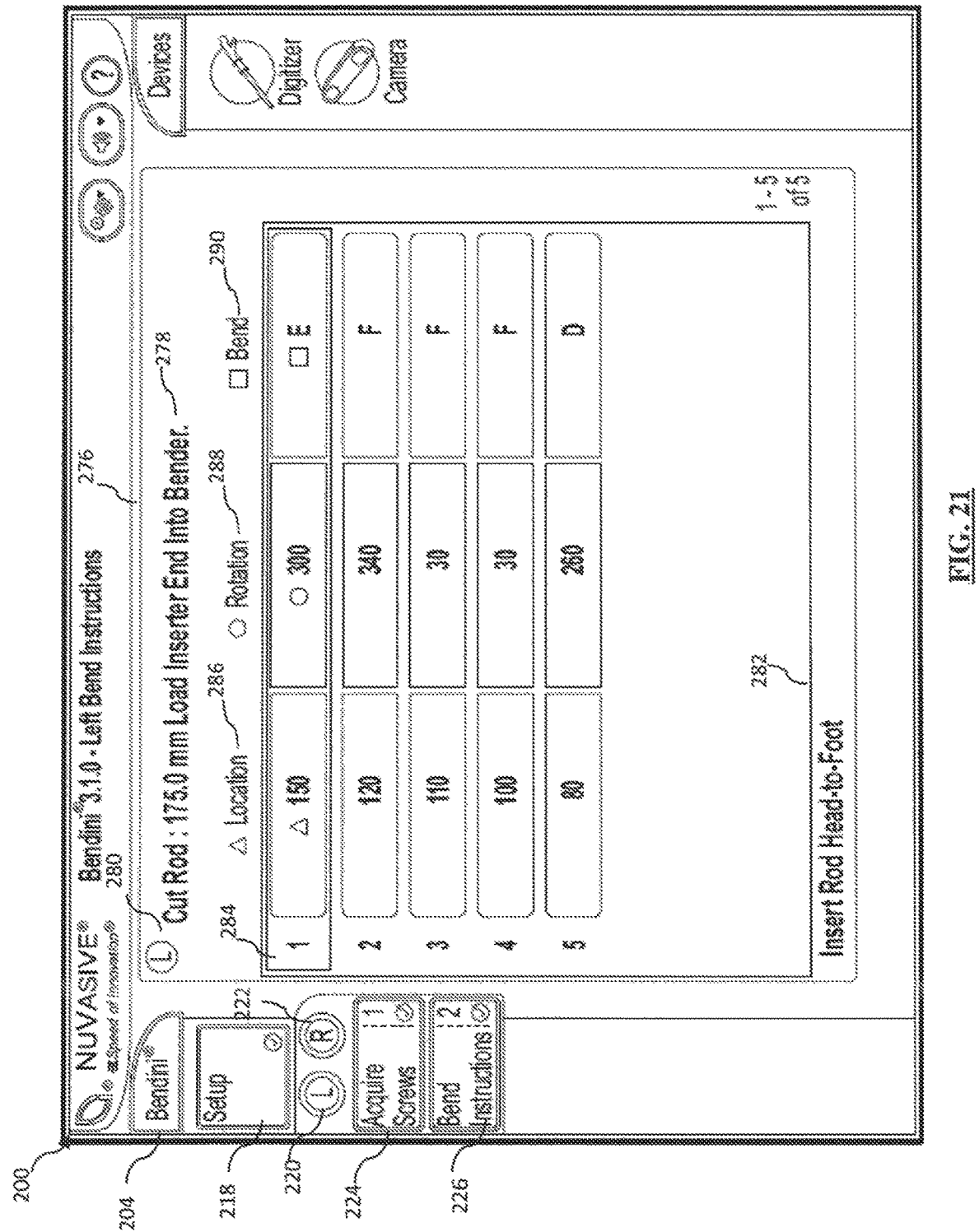
FIG. 21 is a screen shot depicting an example bend instructions screen in the Bend Instructions step of FIG. 15.

The user then selects the "Bend Instructions" button 226 which navigates the display screen 200 to a Bend Instructions (left or right) screen shown by way of example in FIG. 21. The bend instructions within the bend instructions panel 276 allows the user to view the bend instructions corresponding to the resulting rod solution in the Acquire Screws screen (FIG. 20). By way of example, the bend instructions panel 276 contains three fields containing various aspects of the bending instruction: upper message field 278, bender instructions field 280, and lower message field 282. By way of example, the upper message field 278 may communicate the rod cut length, rod type, and/or rod loading instructions to the user (e.g. "Cut Rod: 175.00 mm Load Inserter End Into Bender"). The bender instructions field 280 displays rows 284 of bend maneuvers in location 286, rotation 288, and bend angle 290 to perform on the mechanical bender 18 as will be described in greater detail below. In the example shown in FIG. 21, there are five rows indicating five bend instructions. The lower message field 282 may communicate the direction of insertion or orientation of implanting the rod to the user. For example, the lower message field 282 shown in FIG. 21 provides the following sample instruction: "Insert Rod head to foot." In some implementations, the rod insertion direction into the patient is dependent on the sequence of screw digitization (superior-to-inferior or inferior-to-superior). According to one or more preferred embodiments, the bend instruction algorithm takes into account the orientation of the inferior, superior, anterior, and posterior aspects of the rod and ensures that these aspects are known to the user. As the instructions for use direct the user to load the rod into the bender, the system 10 manages which bends are imparted on the rod first based on the severity of the bend angles. The section of the bend instructions with greater bend angles may be performed first then the straighter bend sections of the bend instructions may be performed last. Further, the instructions may also direct the user to align a laser line or orientation line on the rod to an alignment arrow (not shown) on the mechanical rod bender 18. This alignment controls the Anterior/Posterior orientation of the rod geometry and generates bend instructions accordingly. The user follows the bend instructions generated by the system 10 for location (location may be color-coded on the bender 18 and on the screen 200 as green triangle), rotation (rotation may be color-coded on the bender 18 and on the screen 200 as red circle), and bend angle (bend angle may be color-coded on the bender 18 and on the screen 200 as blue square), sequentially, starting at the first bend instruction and working sequentially until the final bend is completed. From here, the user may repeat steps 190-198 on the rod construct for the contralateral side of the patient's spine.

Within a surgical procedure, a user may wish to toggle between left and right screens to view left and right digitized screw points, rod previews, and bend instructions for reference or comparison. Selecting the Left "L" toggle/status button 220 and right "R" toggle/status button 222 allows the user to do so. According to one more implementations, the GUI may additionally include a History feature. Selecting the History button (not shown) will allow the user to refer back to any previous rod bending solution. The user navigates to the Bend Instructions screen 226 based on choice of the L/R toggle buttons 220, 222 and pressing Bend Instruction button 226. If navigating to previous bend instructions, the Bend Instructions screen will display previous bend instructions. Once the user has selected the desired rod solution, the user then executes the bends using the mechanical bender 18.

Figure 22:
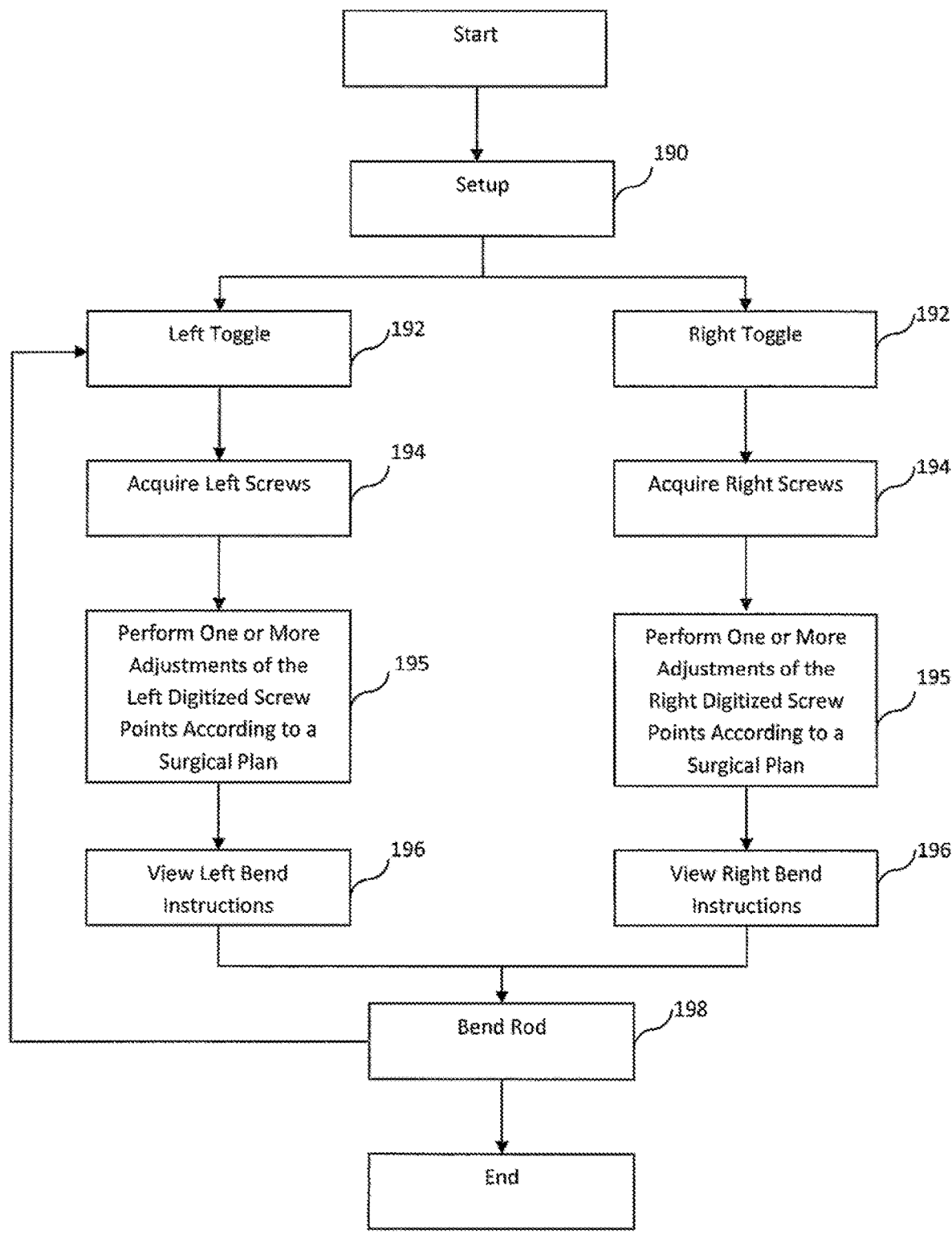
FIG. 22 is a flowchart depicting the steps of the rod bending process according to a second embodiment.

The embodiments described with respect to FIGS. 15 and 18-21 above contemplate digitizing the implanted screw positions and outputting bend instructions for a rod shaped to custom-fit within those implanted screws. In one or more additional embodiments, the system 10 obtains position information of the implanted screws (steps 192 and 194), accepts correction inputs via one or more advanced options features (step 195), and generates for viewing bend instructions for a rod shaped to fit at locations apart from those implanted screw positions (step 196) as depicted in the flowchart of FIG. 22. Installing a rod shaped in this manner could correct a curvature or deformity in the patient's spine according to a user's prescribed surgical plan. Details of the system 10 are discussed now discussed with examples for obtaining a rod bent according to one or more surgical plans.

Figure 23:
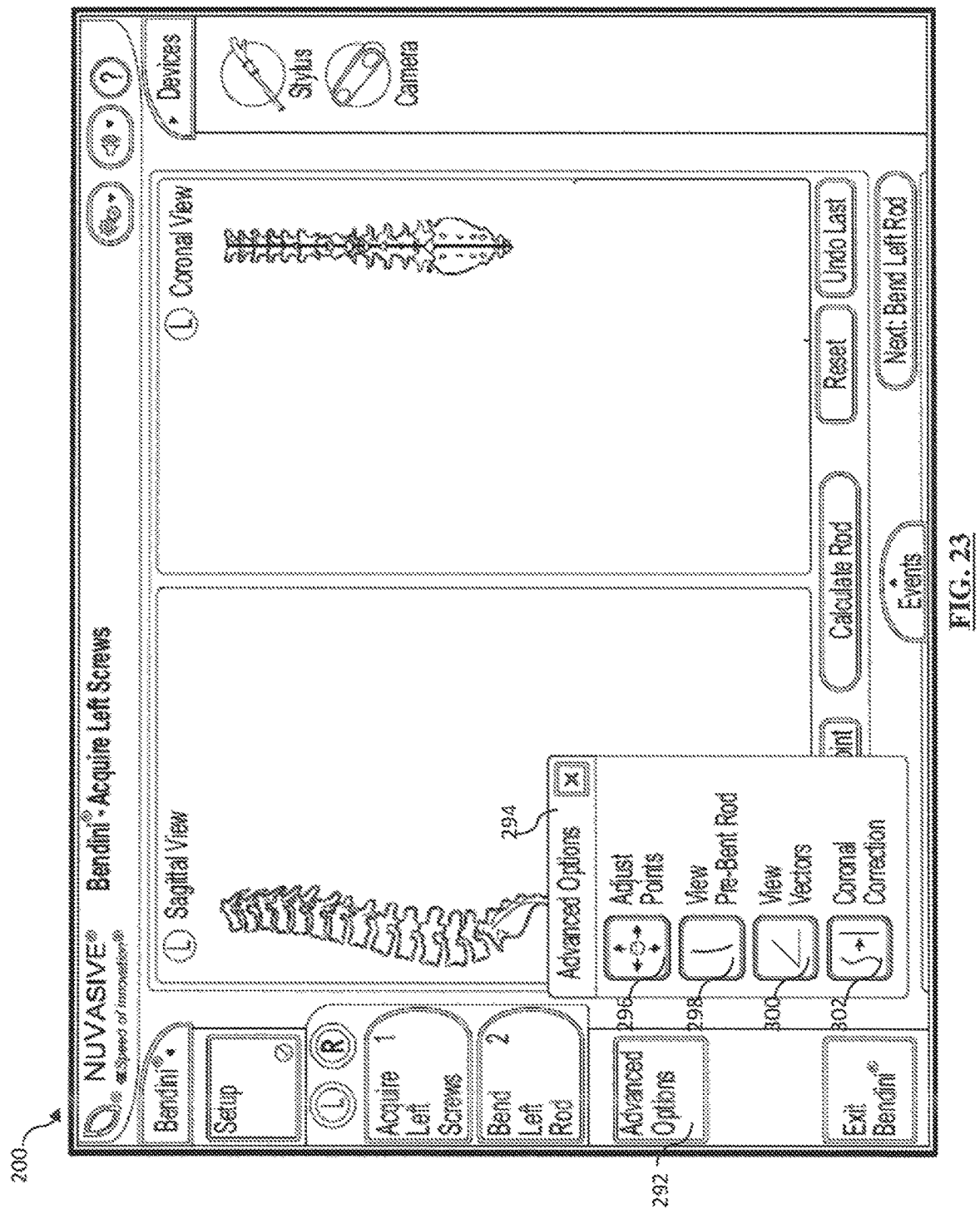
FIG. 23 is a screen shot depicting an example Advanced Options menu screen of the system of FIG. 1.

As depicted in FIG. 23, selecting the "Advanced Options" button 292 expands an Advanced Options menu 292 from which the user may perform one or more corrections to the digitized screw points and the system 10 generates bend instructions that will achieve those desired corrections on the patient's spine once the rod is implanted and the screws are brought to the rod.

Figure 24:
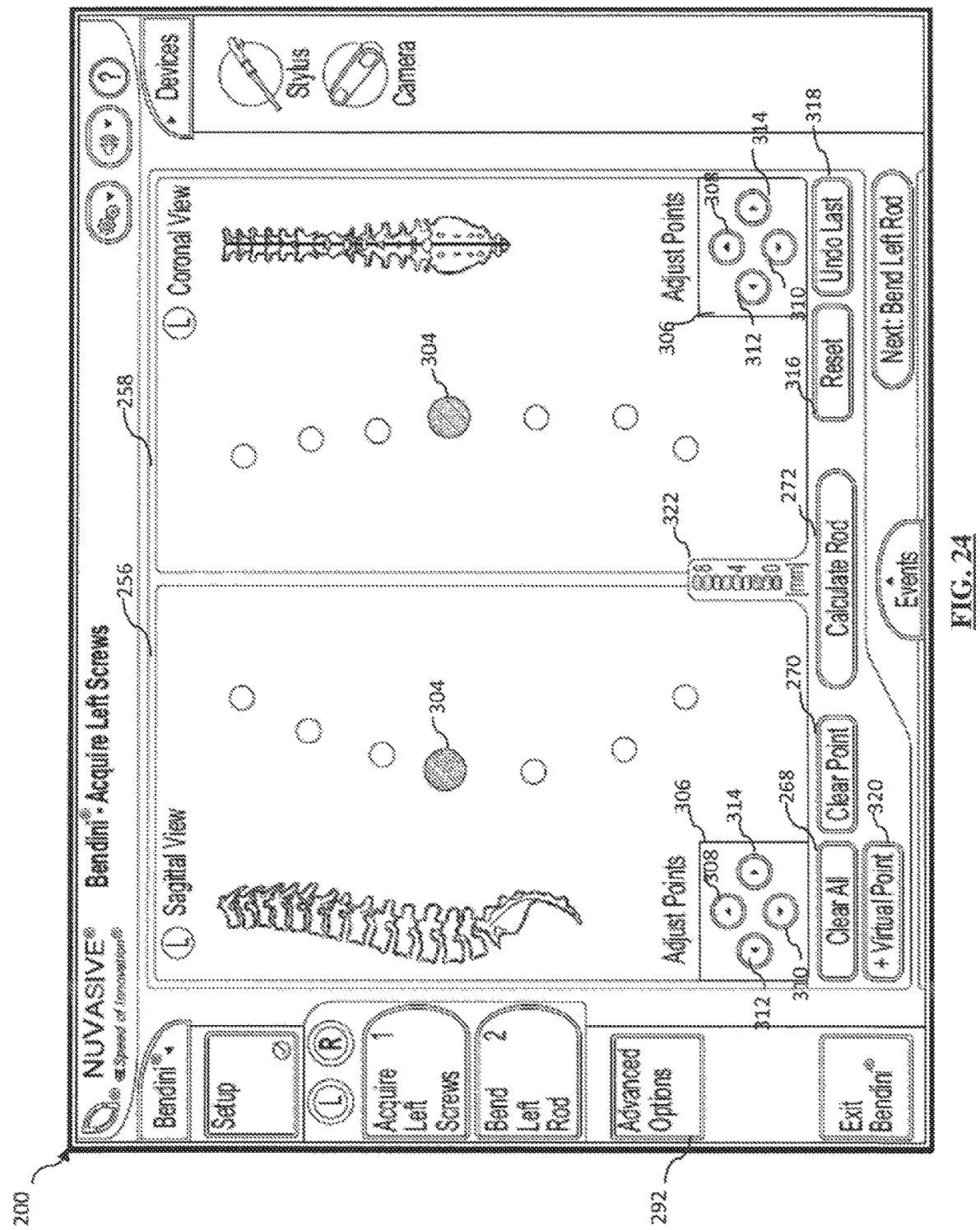
FIG. 24 is a screen shot depicting a first example screen of an Adjust Points feature according to one embodiment.
Figure 25:
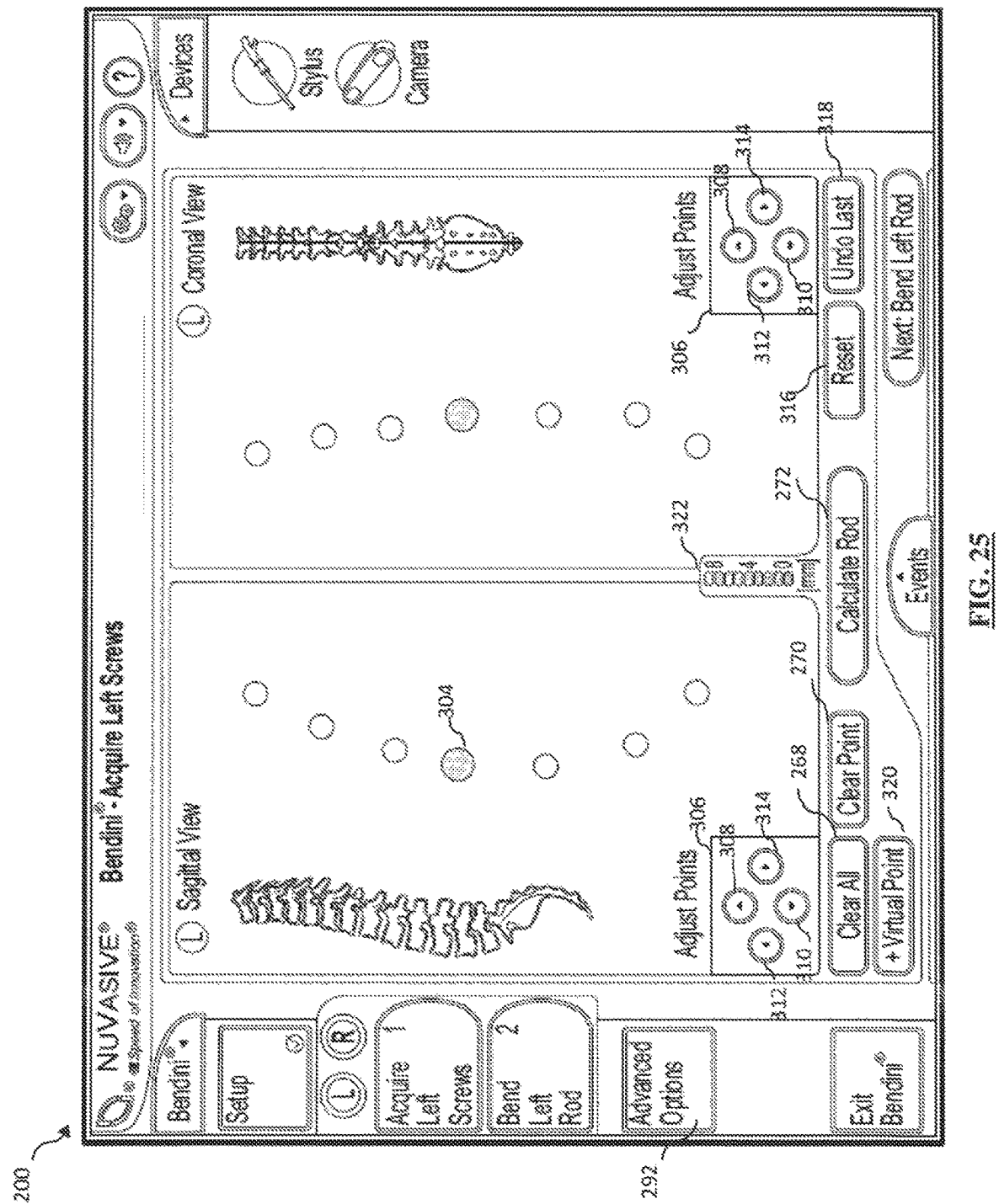
FIG. 25 is a screen shot illustrating a second example screen of the Adjust Points feature of FIG. 24.
Figure 26:
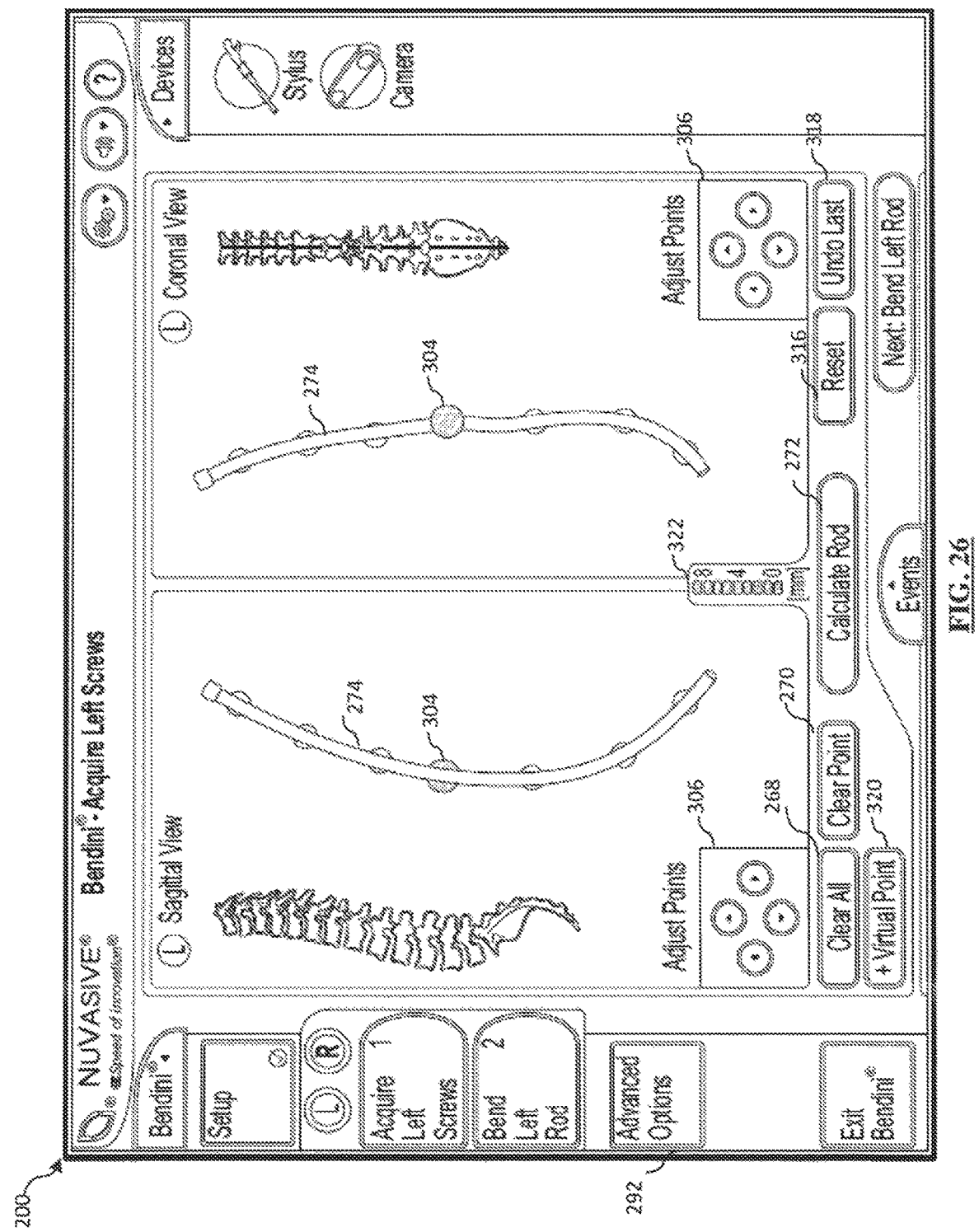
FIG. 26 is a screen shot illustrating a third example screen of the Adjust Points feature of FIG. 24.

In some surgical procedures, a user may wish that the rod bend solution will consider a point that is not a digitized screw point in determining the bend instructions. According to some implementations, this point is an adjusted distance from the digitized screw point location. Selecting the "Adjust Points" button 296 from the Advanced Options menu 292 navigates the user to an Adjust Points screen as depicted in FIG. 23. Selecting a digitized screw location of interest (for example the screw point represented as dot 304 in FIG. 24) highlights the screw point and brings up an adjust points control 306 in each of the sagittal and coronal views 256, 258. The user adjusts point 304 to its desired location in the sagittal and coronal planes using arrows 308, 310, 312, and 314. In some implementations, as the point moves, dot 304 changes color based on the distance from the originally digitized screw location as shown in FIG. 25. Preferably, that color corresponds to color-coded offset distance indicator 322 which provides visual feedback to the user as to the distance the point has been adjusted. As depicted by way of example, dot 304 appears yellow in FIG. 25 indicating that the point has moved 4 mm in each of the sagittal and coronal planes. In some implementations, the system 10 may have a maximum distance from the digitized point past which it will not allow the manipulated point to exceed (by way of example only, this distance may be 5 mm). In other implementations, this distance may be depicted as a distance (for example, the numeral 18 in FIG. 48, indicating that a screw point is 18 mm from its original location). The user may adjust as many points as desired in this fashion. The user may reset all adjusted points to their original configurations via "Reset" button 316 or may undo the last adjusted point via the "Undo Last" button 318. Once satisfied with the adjusted points, the user may either proceed to one or more additional advanced options as set forth below or select "Calculate Rod" 272. Once "Calculate Rod" 272 has been selected, the system 10 generates a rod in which the curve traverses the adjusted points, as in FIG. 26, thereby creating a correction-specific rod and providing the user with the ability to correct the curvature or deformity in the spine according to his or her prescribed curve.

According to other implementations, a user may wish for a smoother rod bend. When the "Virtual Point" button 320 (shown by way of example in FIG. 25) is selected, the system 10 allows the user to add an additional point anywhere in between the superior-most and inferior-most digitized screw locations. While there is no screw at this location, this point is taken into consideration during the curve calculation and may coerce the curve into a more natural shape yielding a smoother rod bend. Once satisfied with the virtual points, the user may either proceed to one or more additional advanced options as set forth below or select "Calculate Rod" 272 and as described above, the system 10 generates a correction-specific rod solution 274 that the user may use to correct the spine to the shape of the rod.

Figure 27:
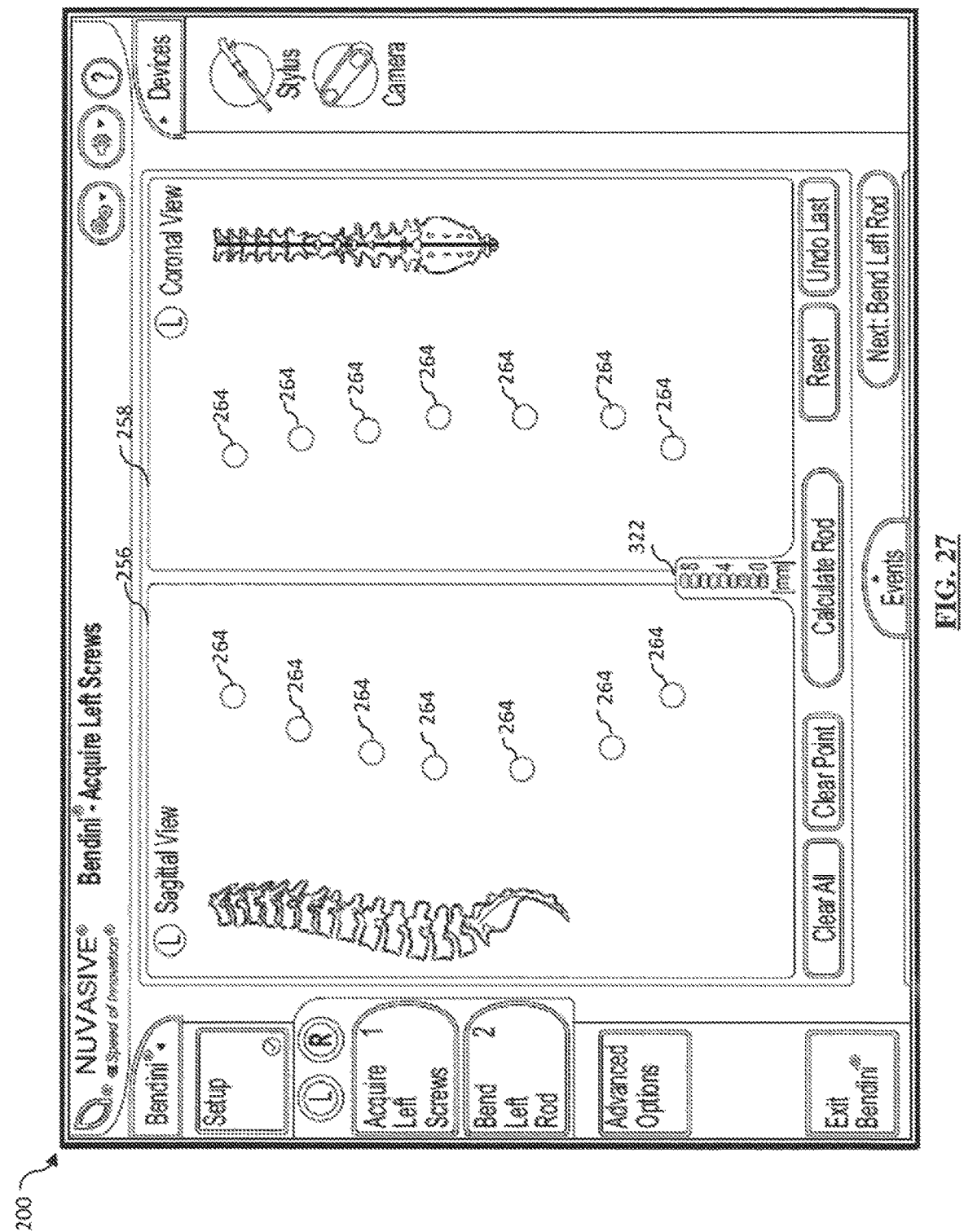
FIG. 27 is a screen shot illustrating a first example screen of a Pre-Bent Preview feature according to one embodiment.
Figure 28:
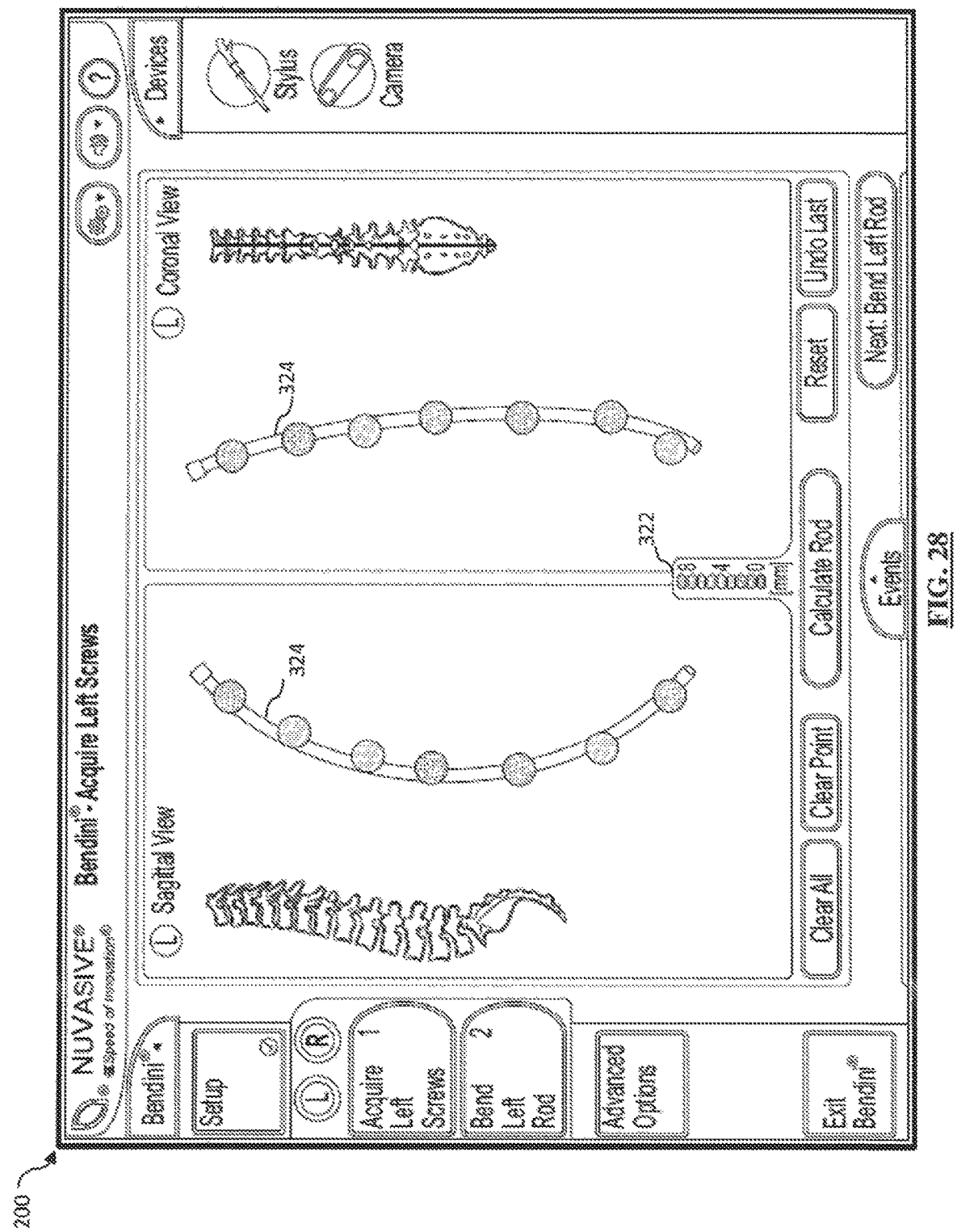
FIG. 28 is a screen shot illustrating a second example screen of the Pre-Bent Preview feature of FIG. 27.
Figure 29:
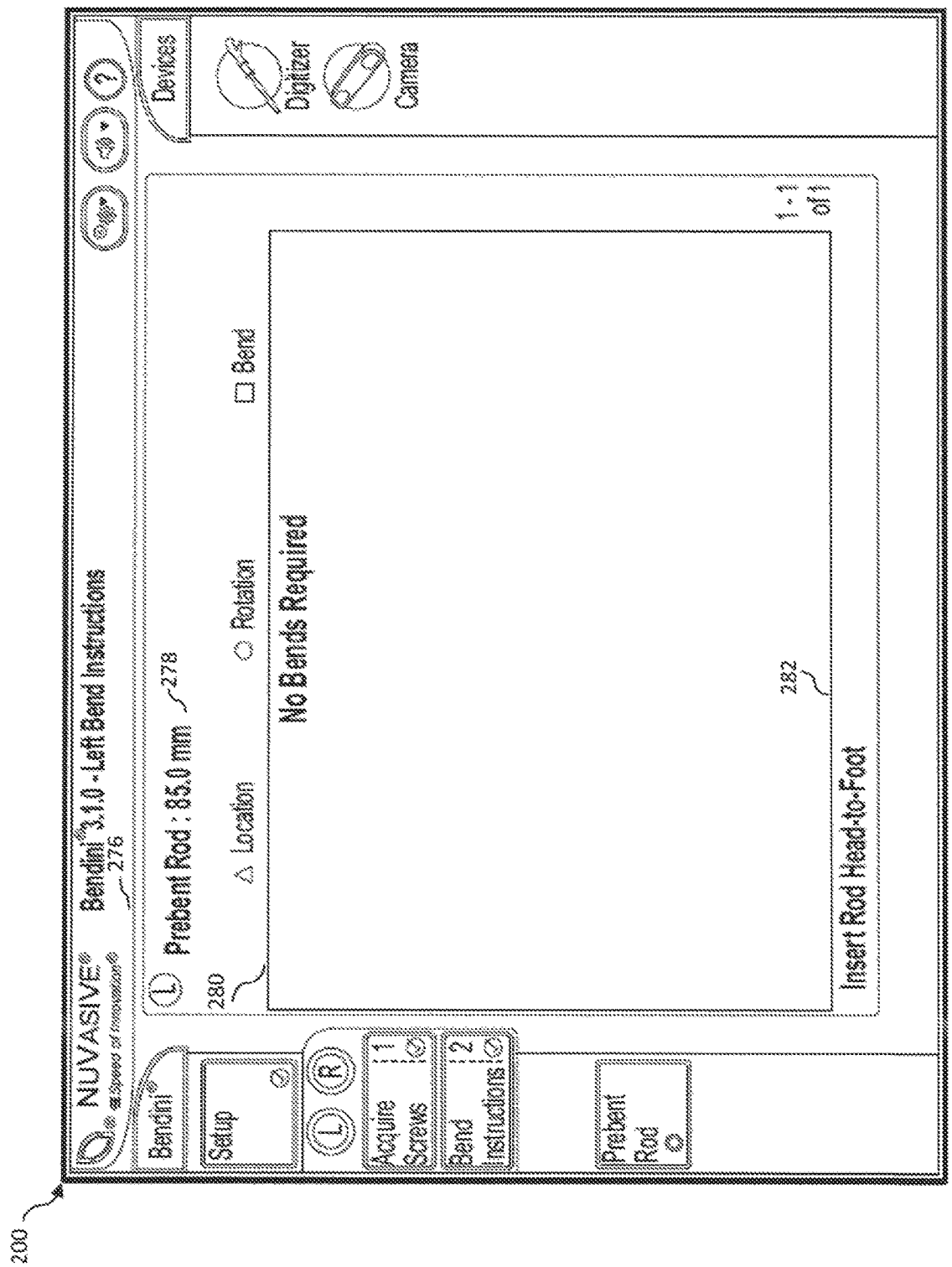
FIG. 29 is a screen shot illustrating a third example screen of the Pre-Bent Preview feature of FIG. 27.

It may be advantageous for some patient anatomies for a user to use a pre-bent rod. Use of a pre-bent rod eliminates the need for making additional bends to a rod while assuring that a desirable rod curve is achieved. After all screw points have been digitized in the Acquire Screws step 194, selecting the "View Pre-Bent Rod" button 298 from the Advanced Options menu 292 navigates the user to a "View Pre-Bent Rod" screen as depicted in FIGS. 27-28. Based on the digitized screw locations shown in FIG. 27, the system 10 calculates and outputs the best pre-bent rod geometry based on the selected manufacturer's rod system that was chosen during the setup step 190 (e.g. NuVasive® Precept®) and displays the best fit virtual pre-bent rod solution 324 available on top of the digitized screw points for viewing in the sagittal and coronal views 256, 258 (see FIG. 28). Preferably, the system 10 only generates a pre-bent rod solution if the geometry of the pre-bent rod fits the digitized screw points within a predetermined curve fitting tolerance (e.g. 7 mm). According to one or more embodiments (as depicted in FIG. 28), a color-coded offset distance indicator 322 may provide the user with an indication of the distance each screw position will be from the pre-bent rod construct. If the user is satisfied with the pre-bent rod suggestion, the system 10 proceeds to the Bend Instructions step 196 which displays the corresponding pre-bent rod specifications in the Bend Instructions Screen (FIG. 29). The upper message field 278 instructs the user that, based on the digitized screw points, an 85.0 mm pre-bent rod is recommended. From here, the user may decide whether the patient's anatomical and surgical requirements would be better suited with a pre-bent option or a custom-bent option. Armed with the information from FIGS. 27-29, the user may then adjust the screw positions to fit the pre-bent rod if needed (e.g., adjust the screw head, adjust the screw depth, etc.).

In some instances, a user may want to align or correct the patient's spine in the sagittal plane (i.e., add or subtract lordosis or kyphosis). The system 10 includes a sagittal correction feature in which the user is able to measure the amount of lordosis in the spine and adjust angles in the sagittal plane. The system 10 then incorporates these inputs into the bend algorithm such that the rod solution includes the desired alignment or correction.

Figure 30:
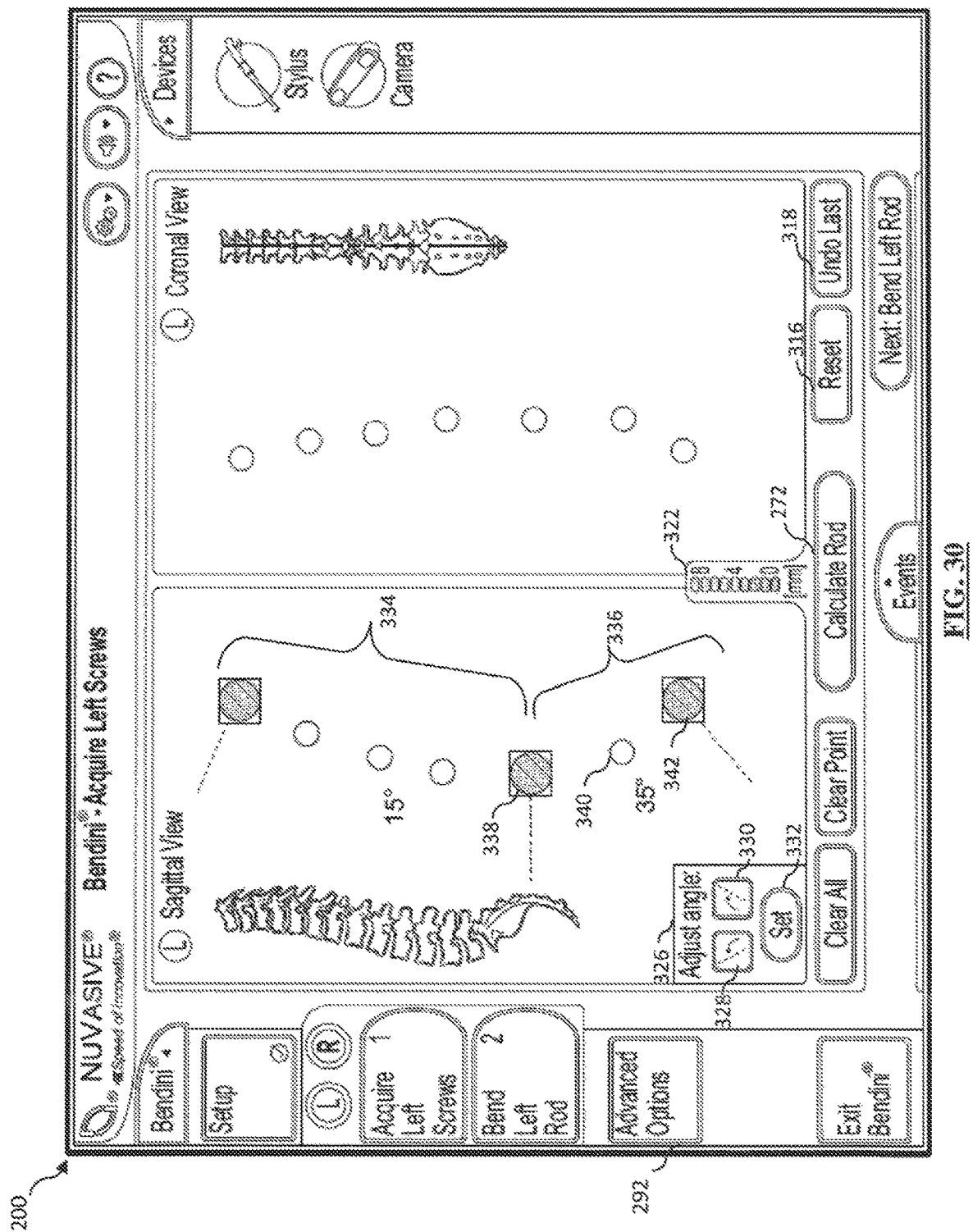
FIG. 30 is a screen shot illustrating a first example screen of a Sagittal Correction feature according to one embodiment.
Figure 31:
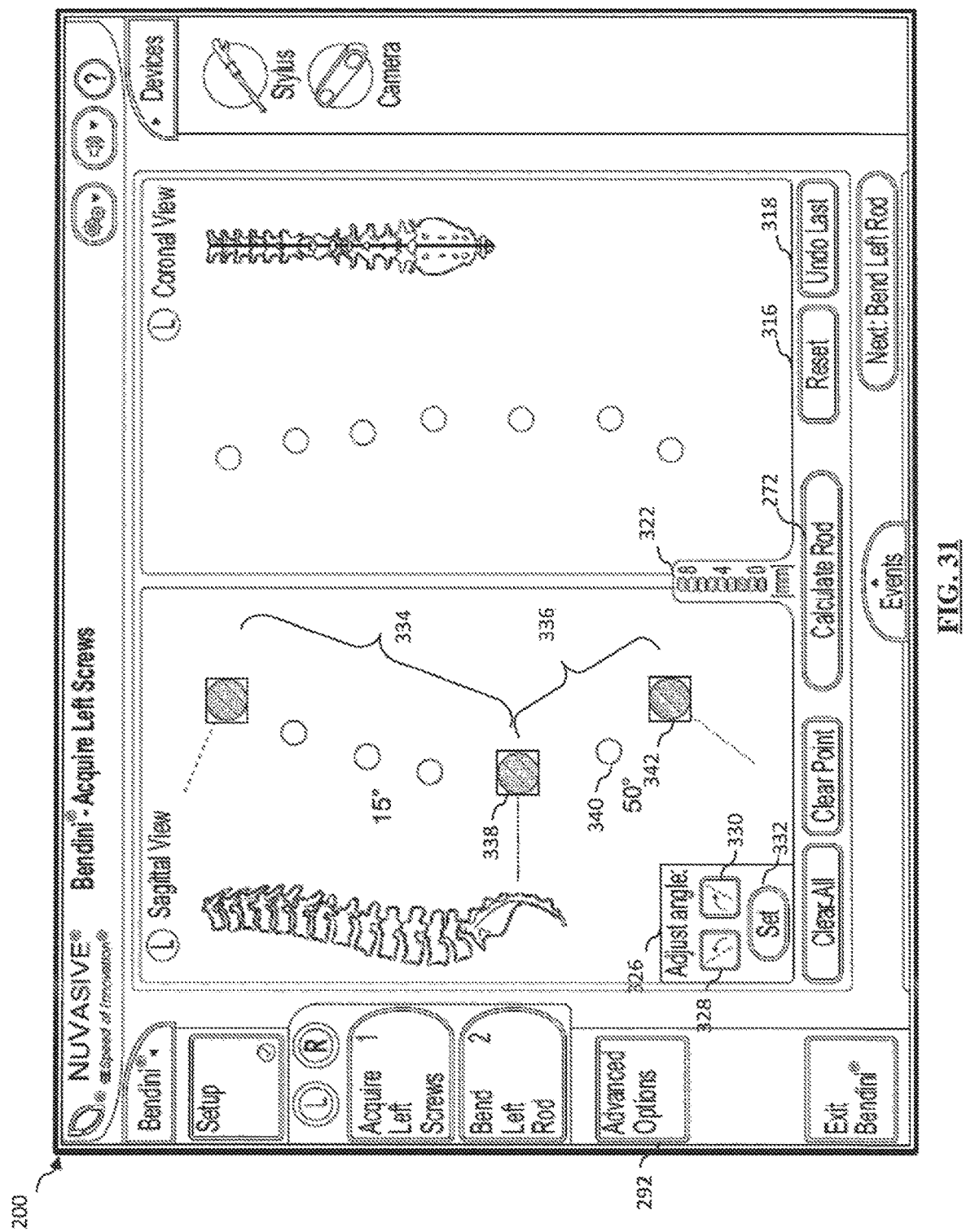
FIG. 31 is a screen shot illustrating a second example screen of the Sagittal Correction feature according to the first embodiment.
Figure 33:
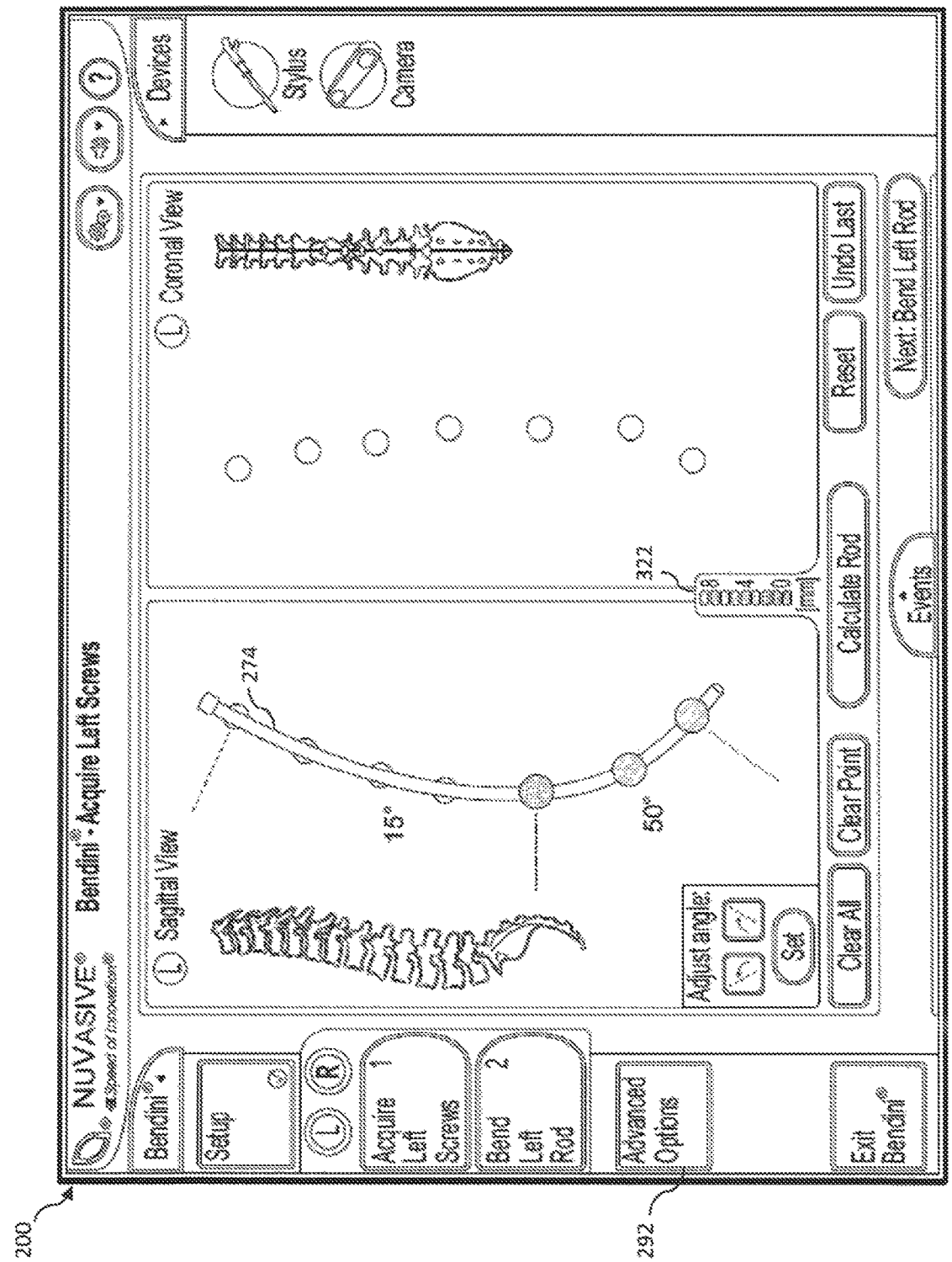
FIG. 33 is a screen shot illustrating an additional example screen of the Sagittal Correction feature according to the first and/or second embodiment.

Selecting the "View Vectors" button 300 from the Advanced Options menu 292 initiates the sagittal correction feature. The user may select at least two points of interest and the system then determines the appropriate vector in the sagittal view. According to the embodiment shown in FIGS. 30-31 and 33, the angles are measured and adjusted based on the screw trajectory screw axis position) using the digitized screw data acquired in the Acquire Screws step 194. As shown in FIG. 30, the user selects at least two screw points of interest (e.g., screw points 338 and 342). The system 10 then measures the angle between the screw trajectories (shown here as 35 degrees). In some implementations, the system 10 may measure the total amount of lumbar lordosis by measuring the lumbar lordosis angle 334 in the superior lumbar spine (shown in FIG. 30 as 15 degrees) and the lumbar lordosis angle 336 in the inferior lumbar spine (show in FIG. 30 as 35 degrees). Using the angle adjustment buttons 328, 330 on the Angle Adjustment Menu 326, the user may increase or decrease the desired angle correction of the spine in the sagittal plane (i.e., add or subtract lordosis or kyphosis superiorly or inferiorly). As the angle is adjusted, the angular position 336 between the two screw points 338, 342 is changed as well. FIG. 31 illustrates an example in which the angular position 336 between points 338 and 342 is increased to 50 degrees). The system 10 may include a color-coded offset distance indicator 322 to provide the user with an indication of the distance each digitized screw position will be adjusted in the sagittal plane as described above. Once the desired amount of angular correction is achieved, the user may select the "Set" button 332, and then the "Calculate Rod" button 270. The system 10 then displays a rod solution 274 incorporating the user's clinical objective for correction of the spine in the sagittal plane as depicted in FIG. 33.

Figure 32:
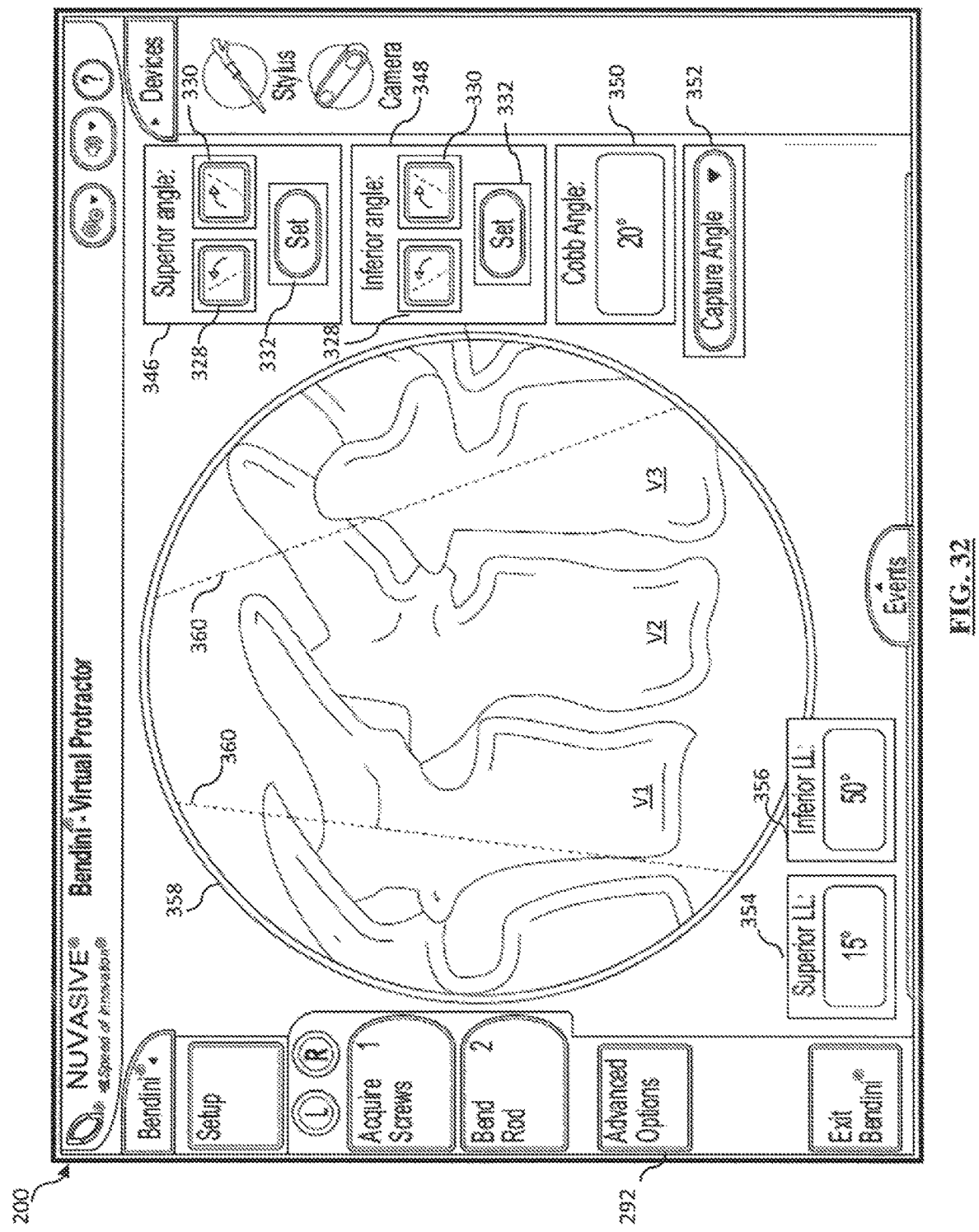
FIG. 32 is a screen shot illustrating a first example screen of the Sagittal Correction feature according to a second embodiment.

According to the embodiment of the sagittal correction feature shown in FIG. 32, the superior and inferior lumbar lordosis angles 334, 336 are measured, displayed, and adjusted referencing anatomy from an imported lateral radiographic image. By way of example, lateral radiographic image 358 may be inputted into the system 10. The user may touch the screen 200 and move lines 360 over at least two points of interest (e.g. the superior endplate of V1 and the inferior endplate of V3) and the system 10 then measures the angle between the two lines 360. The Using the angle adjustment buttons 328, 330 on the Superior Angle Adjustment Menu 346 or Inferior Angle Adjustment Menu 348, the user may increase or decrease the desired angle correction of the spine in the sagittal plane (i.e., add or subtract lordosis or kyphosis superiorly or inferiorly). As either the superior or inferior lumbar lordosis angle is adjusted, the amount of adjustment is dynamically altered in its respective angle measurement box (i.e., either superior lumbar lordosis angle box 354 or inferior lumbar lordosis angle box 356). As depicted in FIG. 32, the user adjusts angle lines 360 as part of the inferior lumbar lordosis angle. The system 10 measures this angle as 20 degrees as depicted in angle measurement field 350. The user then uses button 330 in superior angle adjustment menu 346 to increase the angle. This change is depicted in inferior lumbar lordosis angle box 356. Once the desired amount of correction is achieved, in this example, it is achieved at 50 degrees. The user may then press the capture angle button 352 and this parameter may be correlated to the digitized screw positions corresponding to the vertebral levels that those angles were measured off of. The system 10 may include a color-coded offset distance indicator 322 to provide the user with an indication of the distance each digitized screw position will be adjusted in the sagittal plane as described above. Once the desired amount of angular correction is achieved, the user may select the "Set" button 332, and then the "Calculate Rod" button 272. The system 10 then displays a rod solution 274 incorporating the user's clinical objective for correction of the spine in the sagittal plane as depicted in FIG. 33.

It is to be appreciated that, because patient position (e.g., pelvic tilt) may have an effect on the lumbar lordosis measurements, the sagittal correction feature of the system will be able to account for any patient positioning-related deviations. It will also be appreciated that in addition to lordotic corrections, the sagittal angle assessment tool may be useful for other types of surgical maneuvers, including but not limited to pedicle subtraction osteotomy (PSO) procedures and anterior column reconstruction (ACR) procedures.

In some instances, a user may want to align or correct the patient's spine in the coronal plane (i.e., correct scoliosis). The system 10 includes one or more coronal correction features in which the user is able to view the patient's spine (and deformity) in the coronal plane via anterior-posterior x-rays; measure one or more anatomic reference angles; and/or persuade one or more screw locations towards a particular coronal alignment profile by manually or automatically biasing which direction the rod bend curve is adjusted. The system 10 may then incorporates these inputs into the bend algorithm such that the rod solution includes the desired alignment or correction.

Selecting the "Coronal Correction" button 302 from the Advanced Options menu 292 initiates the coronal correction feature. The user may wish to ascertain the degree of coronal deformity by referencing spinal anatomy, measuring the coronal Cobb angles between two anatomical references in the coronal plane, and adjusting those angles intraoperatively as part of the surgical plan to bring the spine into (or closer to) vertical alignment.

Figure 34:
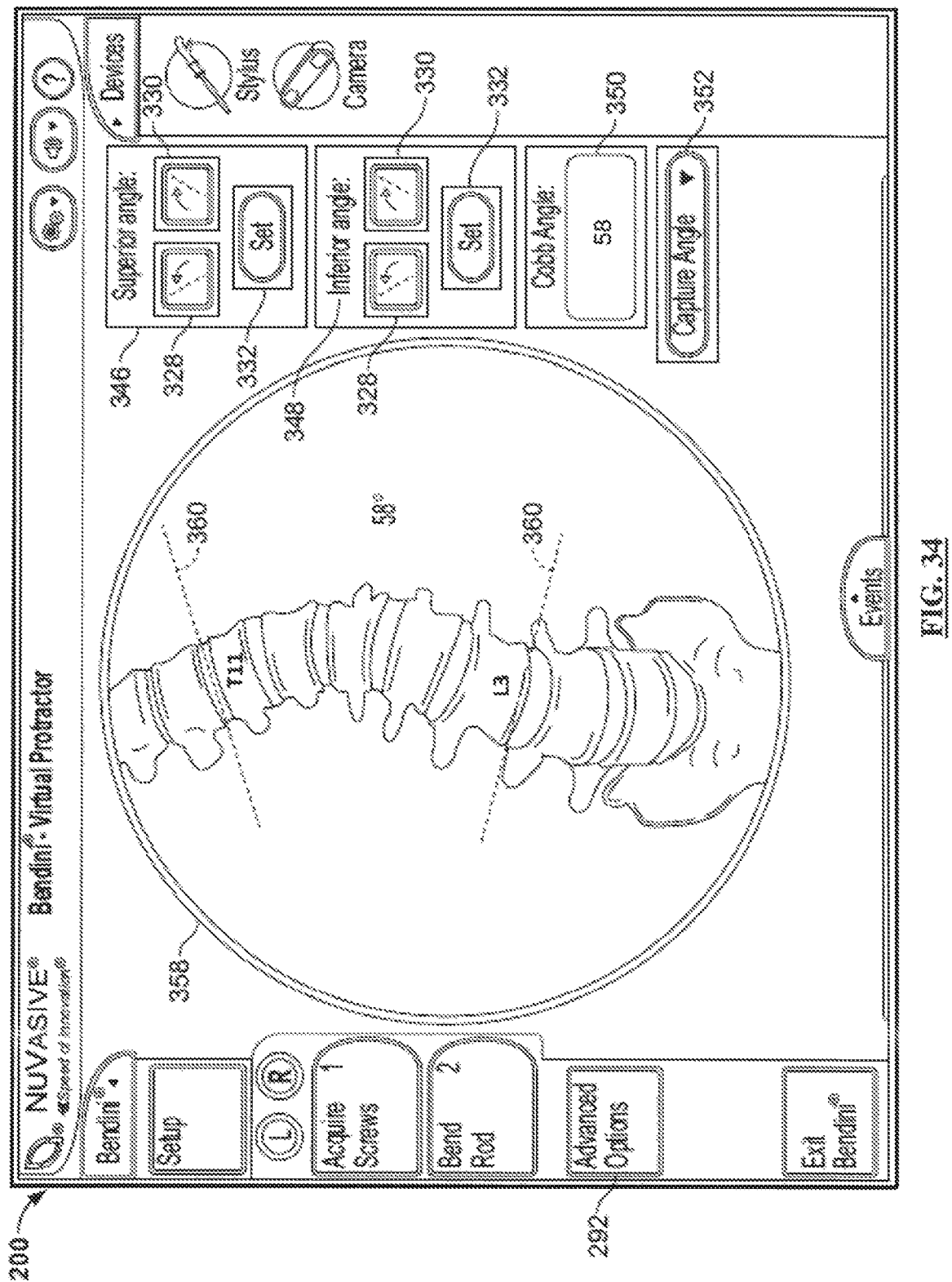
FIG. 34 is a screen shot illustrating a first example screen of the Coronal Correction feature according to a first embodiment.
Figure 35:
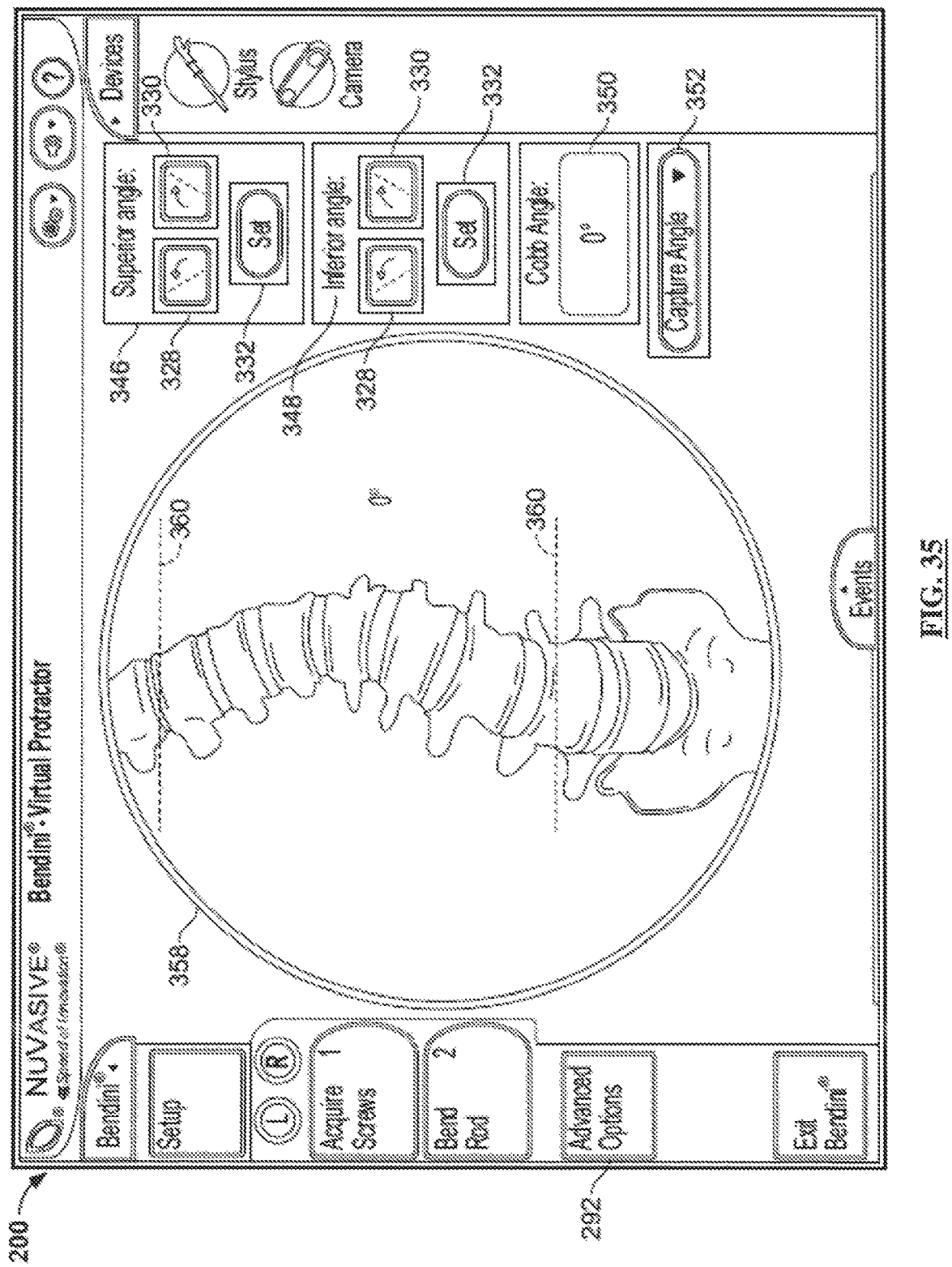
FIG. 35 is a screen shot illustrating a second example screen of the Coronal Correction feature according to the first embodiment.

According to the embodiment shown in FIGS. 34-35, the coronal Cobb angles may be ascertained using anterior-posterior radiographic images. Anterior-posterior radiographic image 358 may be inputted into the system 10. According to one implementation, the coronal Cobb angle may be determined by drawing lines parallel with the endplates of the most tilted vertebrae above and below the apex of the curve and measuring the angle between them. The user may touch the screen 200 and move lines 360 over at least two points of interest (e.g. the superior endplate of T11 and the inferior endplate of L3) and the system 10 then measures the angle between the two lines 360. Using the angle adjustment buttons 328, 330 on the Superior Vertebra Angle adjustment menu 346 and/or the Inferior Vertebra Angle adjustment menu 348, the user may increase or decrease the desired angle correction of the spine in the coronal plane (i.e., add or subtract correction to make the endplates of the superior and inferior vertebrae selected more parallel with one another). As either the superior or inferior component of the coronal angle is adjusted, the coronal Cobb angle measurement may be dynamically altered in the coronal Cobb angle measurement box 350. By way of example, in FIG. 34, the starting coronal Cobb angle is 58 degrees. The user uses buttons 328, 330 to reduce the angle lines 360 between T11 and L3. Once the desired amount of correction is achieved (shown, by way of example, in FIG. 35 as a coronal Cobb Angle of 0 degrees), the user may then press the capture angle button 352. This parameter may be correlated to the digitized screw positions corresponding to the vertebral levels that those angles were measured off of. The system 10 may include a color-coded offset distance indicator 322 to provide the user with an indication of the distance each digitized screw position will be adjusted in the coronal plane as described above (not shown here). Once the desired amount of angular correction is achieved, the user may select the "Set" button 332, and then the "Calculate Rod" button 272. The system 10 then displays a rod solution 274 incorporating the user's clinical objective for correction of the spine in the coronal plane.

Figure 36:
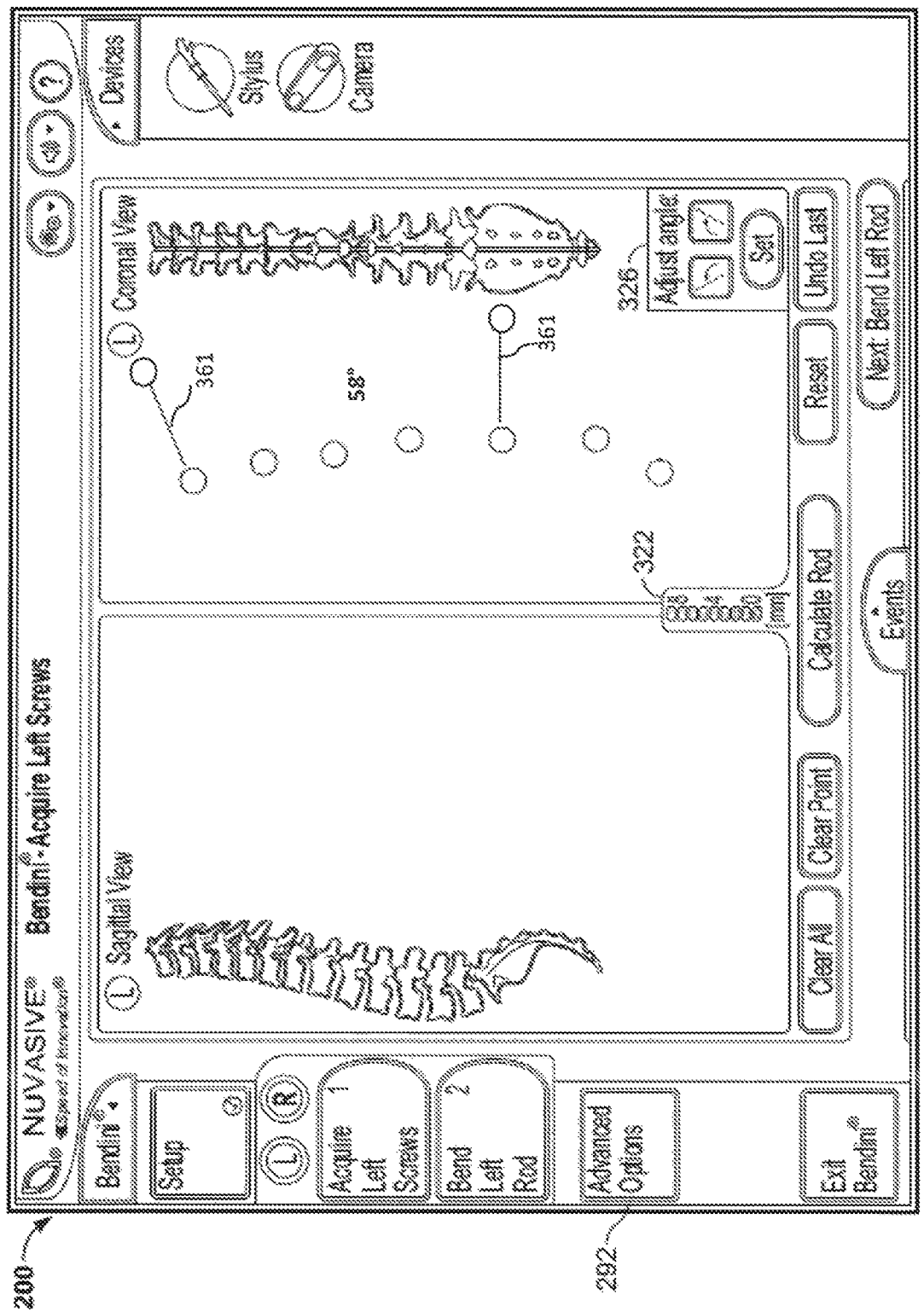
FIG. 36 is a screen shot illustrating a first example screen of the Coronal Correction feature according to a second embodiment.
Figure 37:
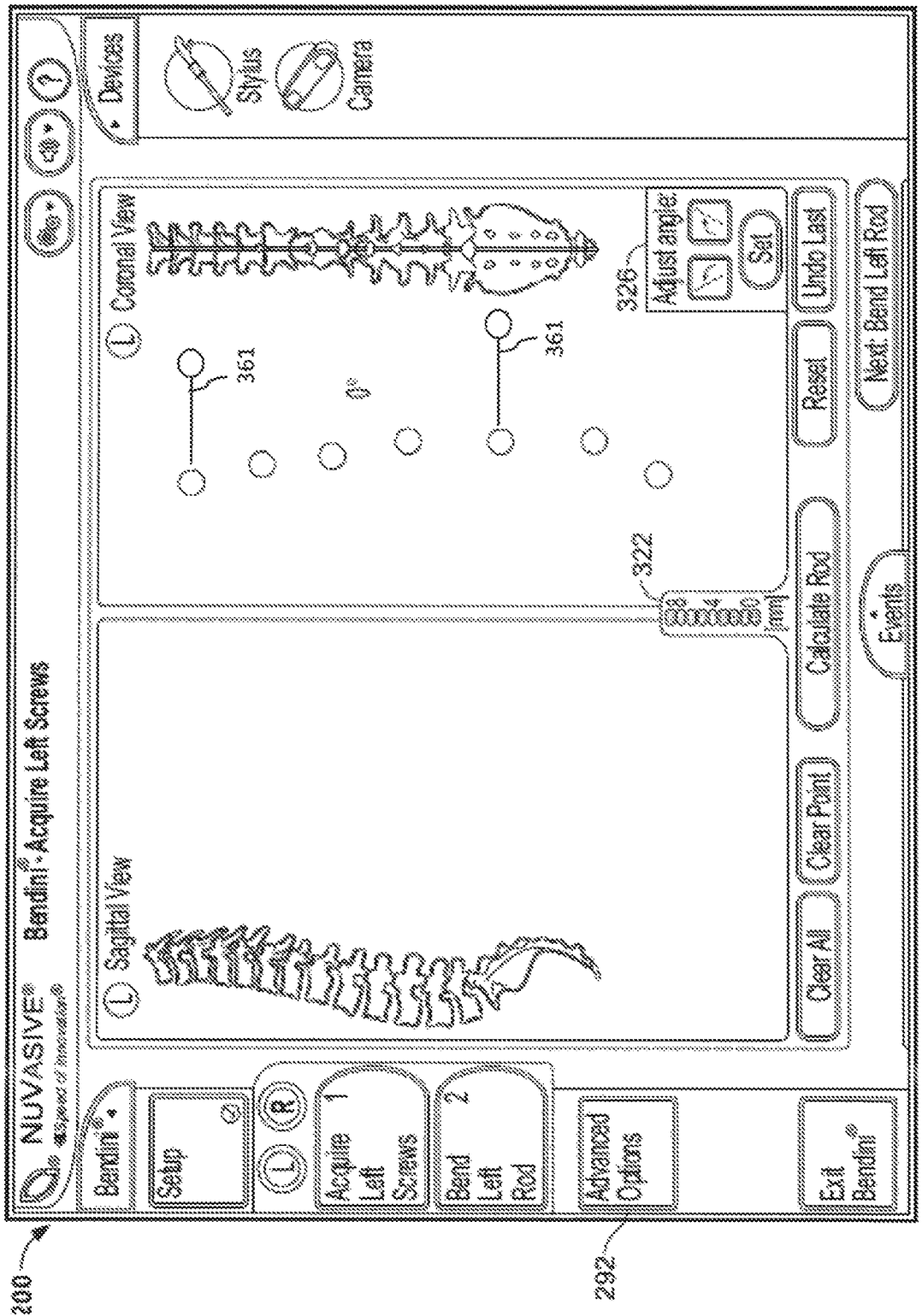
FIG. 37 is a screen shot illustrating a second example screen of the Coronal Correction feature according to the second embodiment.
Figure 38:
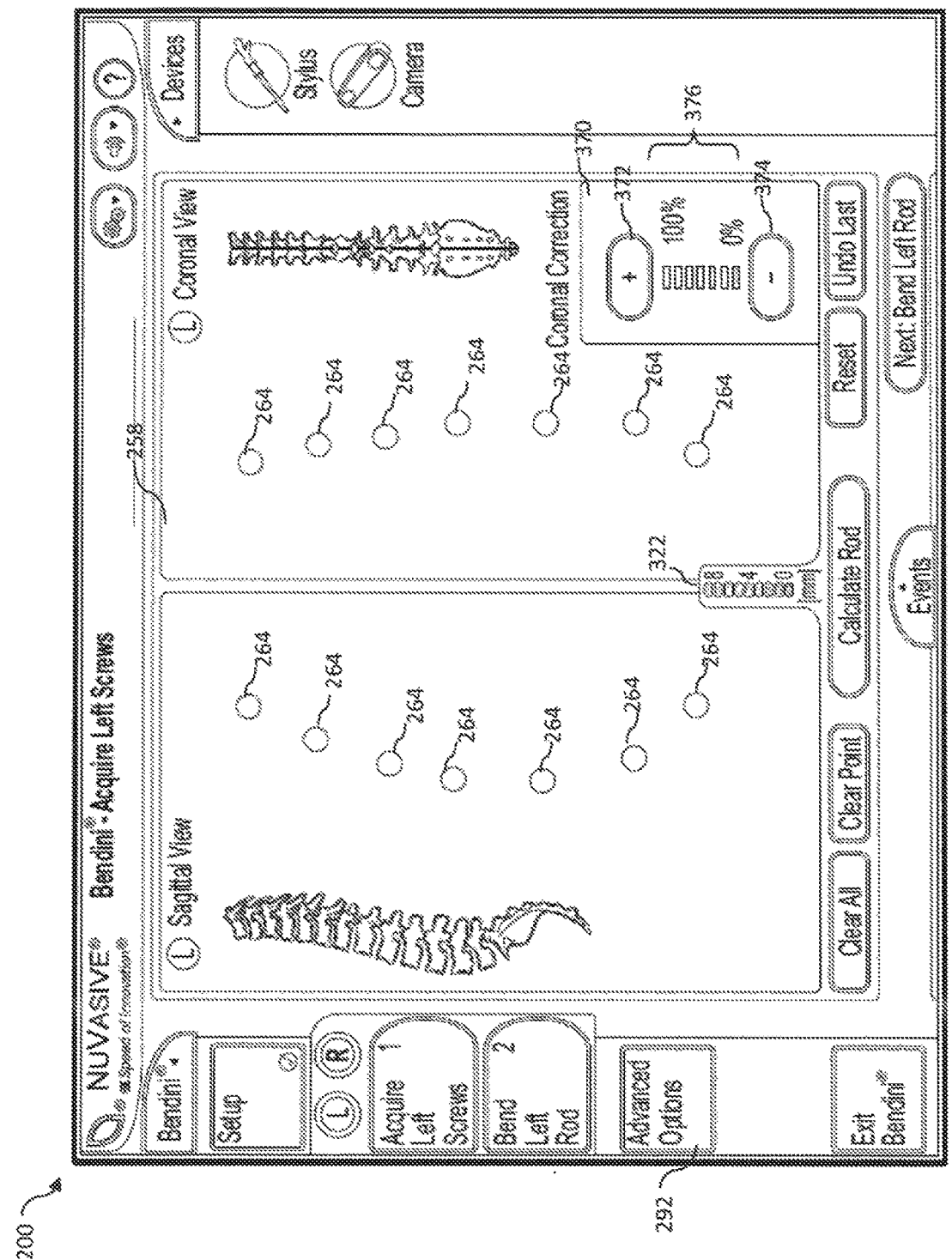
FIG. 38 is a screen shot illustrating a first example screen of the Coronal Correction feature according to a third embodiment.
Figure 39:
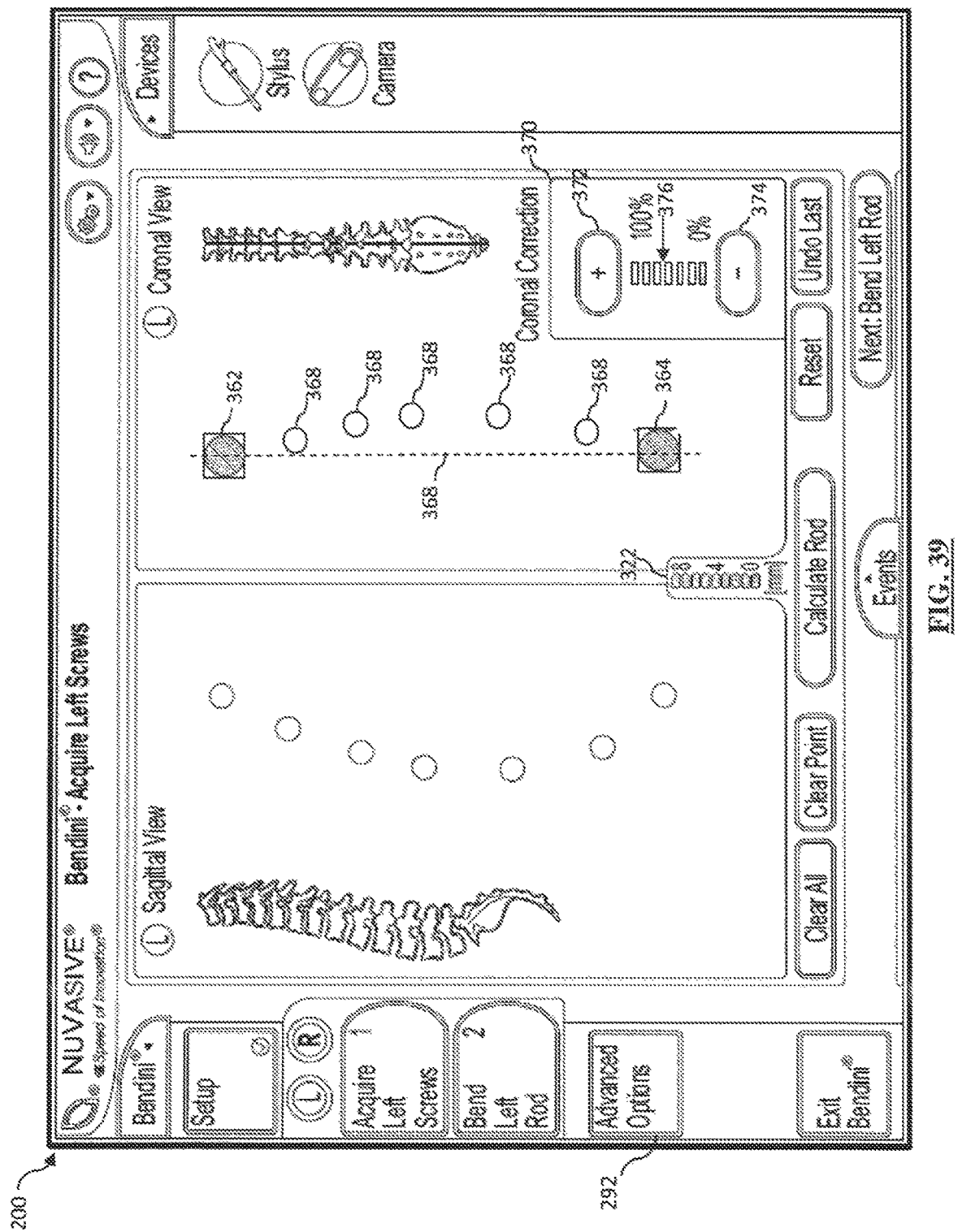
FIG. 39 is a screen shot illustrating a second example screen of the Coronal Correction feature according to the third embodiment.

According to the embodiment shown in FIGS. 36-37, the coronal Cobb angle may be displayed and adjusted referencing anatomy from digitized locations of screws placed in the left and right pedicles of the vertebrae of interest. The system links left and right digitized screw locations for each respective vertebrae (line 361) and measures the angle between the two lines 361 (shown here in FIG. 36 as 58 degrees). According to one implementation, the coronal Cobb angle may be determined by selecting the screw location of the most tilted vertebrae above and below the apex of the curve. Using the angle adjustment buttons on the Angle Adjustment menu 326, the user may increase or decrease the desired angle correction of the spine in the coronal plane (i.e. add or subtract correction to make the endplates of the superior and inferior vertebrae selected by the user more parallel with one another). As the coronal angle is adjusted, the Cobb angle measurement may be dynamically altered as set forth above. Here, however, instead of coronal Cobb angle measurement box 351, the Cobb angle may displayed alongside the radiographic image (shown in FIG. 36 with a starting coronal Cobb angle of 58 degrees). The user uses the buttons in menu 326 to reduce the angle lines 361 between T11 and L3. Once the desired amount of correction is achieved (shown, by way of example, in FIG. 37 as 0 degrees, the user may then press the "Set" button 332 and this parameter may be correlated to the digitized screw positions corresponding to the vertebral levels that those angles were measured off of. The system 10 may include a color-coded offset distance indicator 322 to provide the user with an indication of the distance each digitized screw position will be adjusted in the coronal plane as described above (not shown here). Once the desired amount of angular correction is achieved, the user may select the "Calculate Rod" button 272. The system 10 then displays a rod solution 274 incorporating the user's clinical objective for correction of the spine in the coronal plane.

According to one or more other implementations of the coronal correction feature, the user may select at least two points of interest and the system then generates a best fit reference line through all points including and lying between the at least two points of interest. In some instances, the ideal correction of the spine in the coronal plane is a straight vertical line extending between the superior-most and inferior-most screw locations of interest. However, depending on a patient's individual anatomy, achieving a straight vertical line may not be feasible. The user may wish to achieve a certain amount of correction relative to the ideal correction. From the display screen, the user may select a percentage of relative correction between the screw points as digitized (0% correction) and the best fit reference line (100%). Furthermore, the system then calculates a rod solution and shows an off-center indicator 322 to provide a user with an indication of the distance each screw is from the coronally-adjusted rod construct as set forth above.

Figure 40:
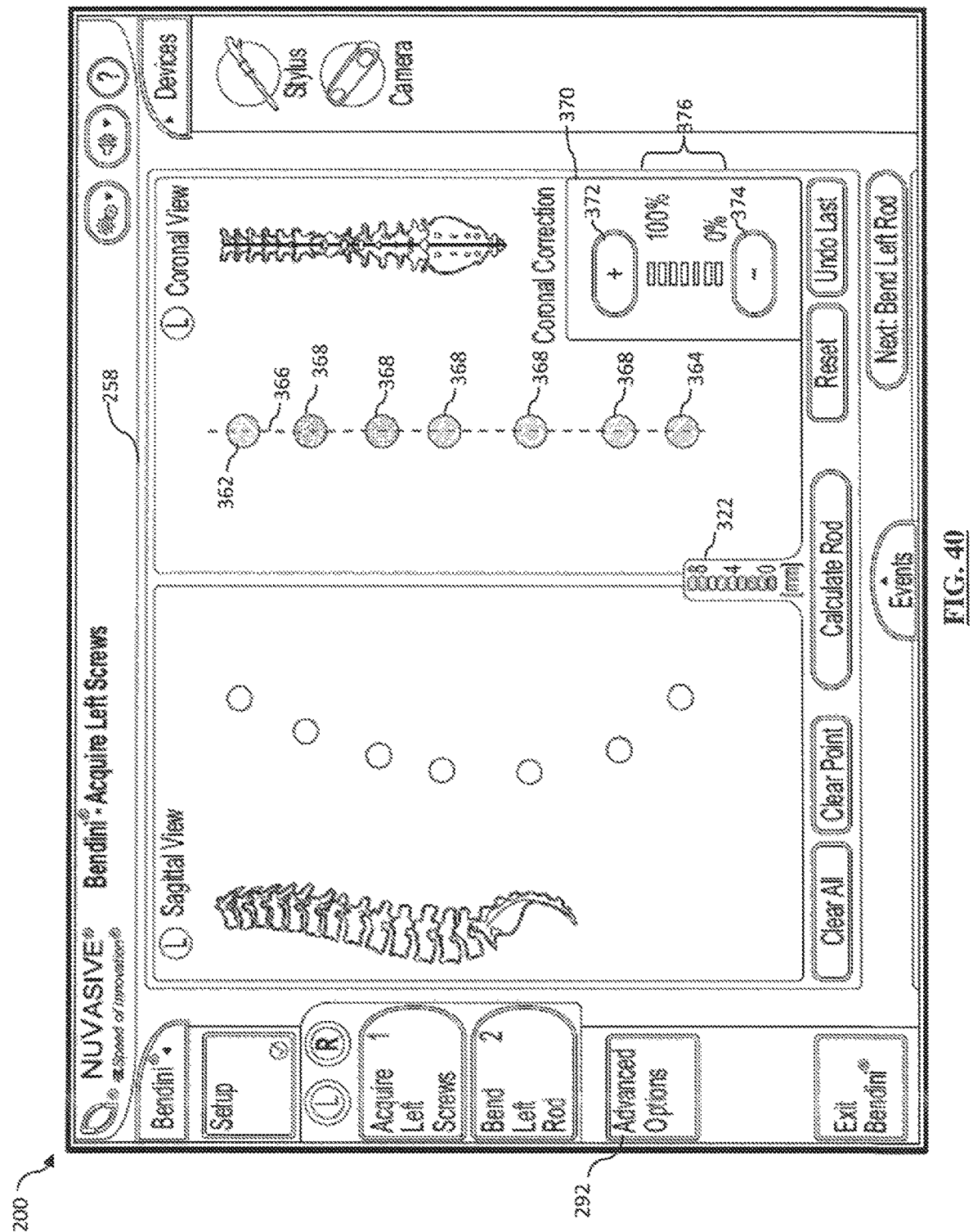
FIG. 40 is a screen shot illustrating a third example screen of the Coronal Correction feature according to the third embodiment.
Figure 41:
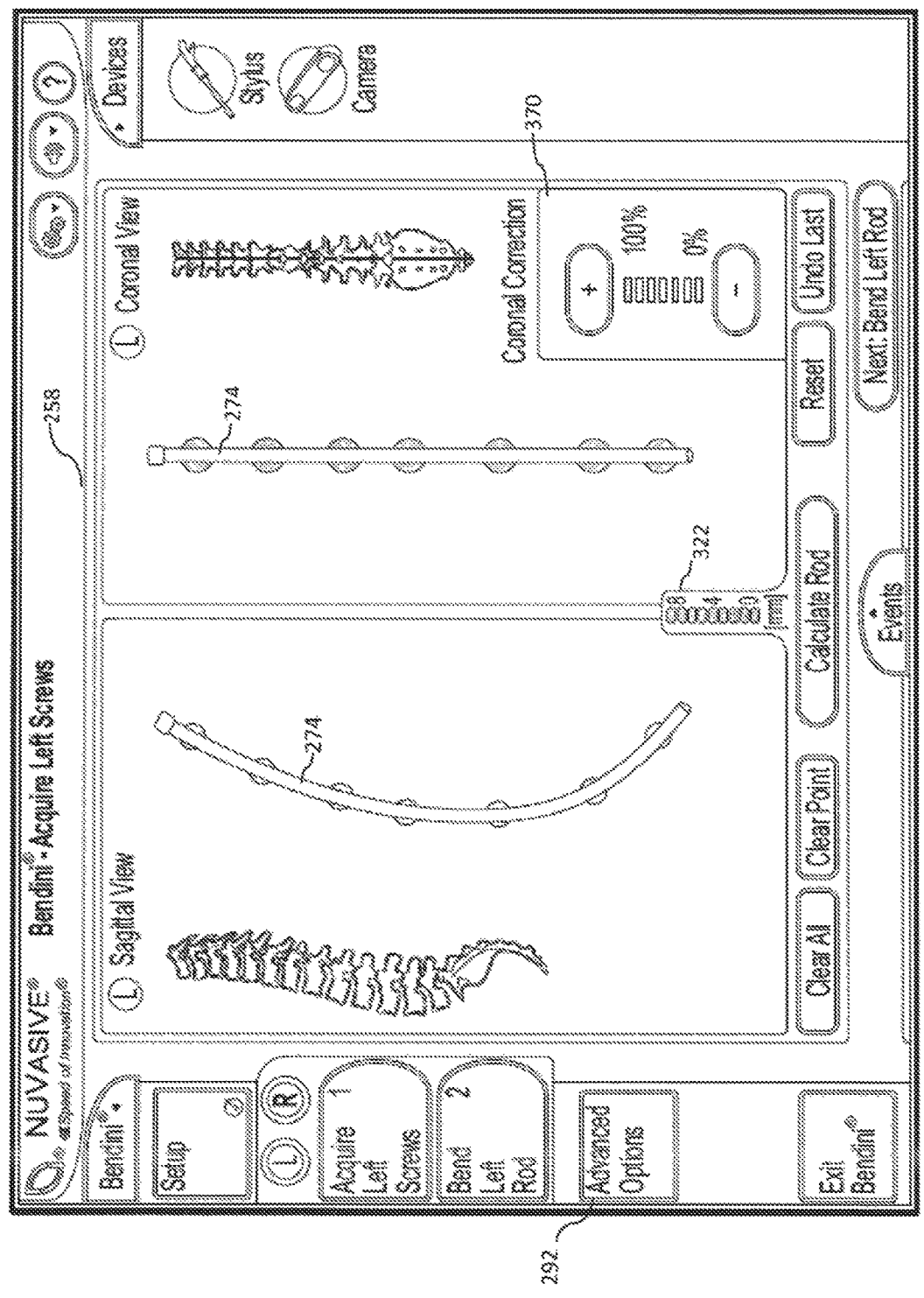
FIG. 41 is a screen shot illustrating a fourth example screen of the Coronal Correction feature according to the third embodiment.

According to the embodiment shown in FIGS. 38-41, the user may straighten all points within the construct (global coronal correction). From the display screen 200, the superior and inferior screw points 362, 364 are selected and the system 10 generates a best fit global reference line 366 through all points 362, 364, 368. Using the Coronal Correction Menu 370, the user manipulates the + and − buttons 372, 374 to adjust the percentage of correction desired. In the example shown in FIG. 36, the amount of desired correction is shown as 100% on the percentage correction indicator 376, meaning the rod solution 274 will be a straight line in the coronal plane and all screw locations will be adjusted to fit the rod/line. As depicted in FIG. 40, the system 10 may include a color-coded offset distance indicator 322 to provide the user with an indication of the distance each digitized screw position will be adjusted in the coronal plane as set forth above. If the user deems this an acceptable rod solution, the user selects the "Calculate Rod" button 272 to view the rod solution 274 (FIG. 41) and receive bend instructions or proceeds to another advanced feature as will be described in greater detail below.

Figure 42:
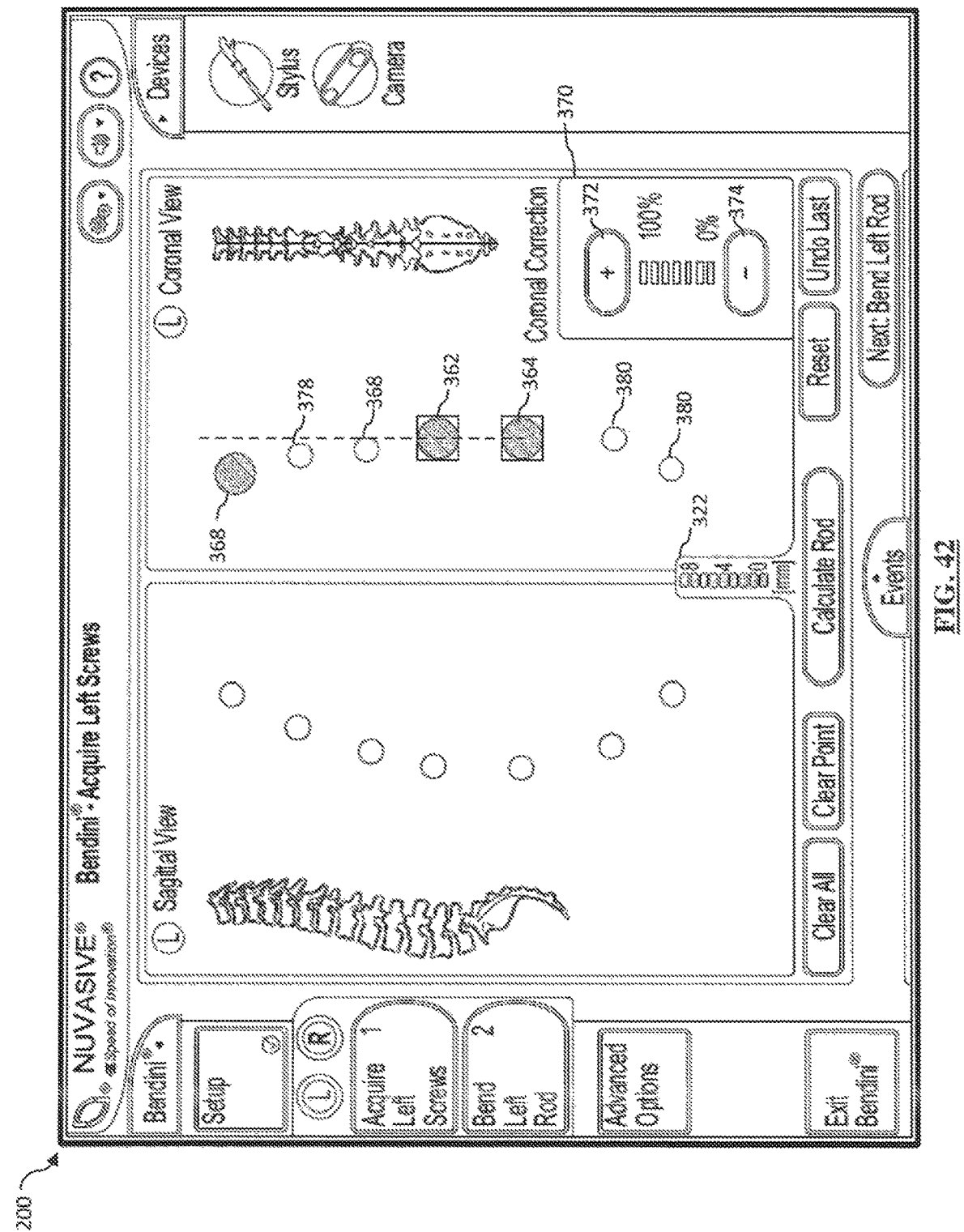
FIG. 42 is a screen shot illustrating a first example screen of the Coronal Correction feature according to a second embodiment.
Figure 43:
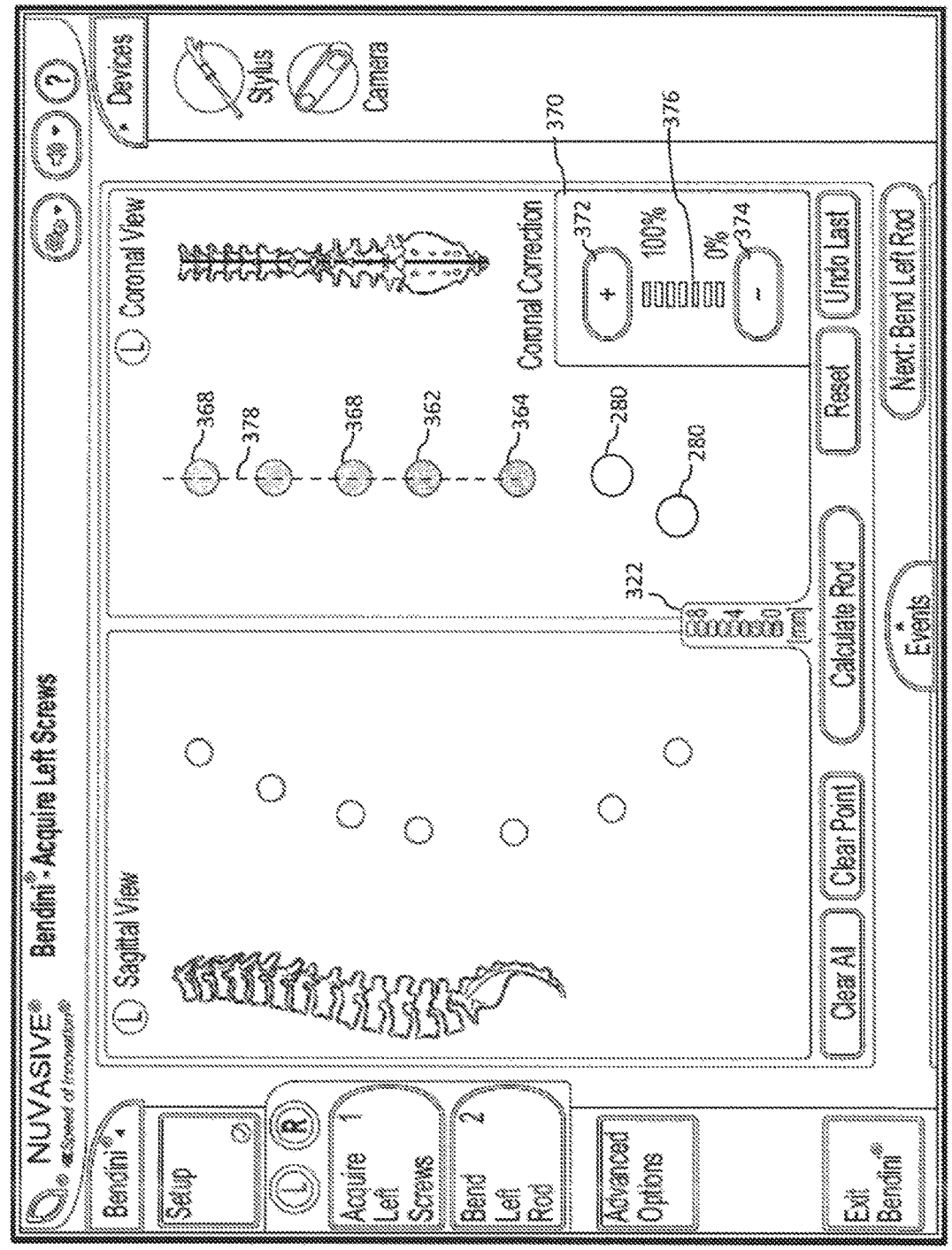
FIG. 43 is a screen shot illustrating a second example screen of the Coronal Correction feature according to the second embodiment.
Figure 44:
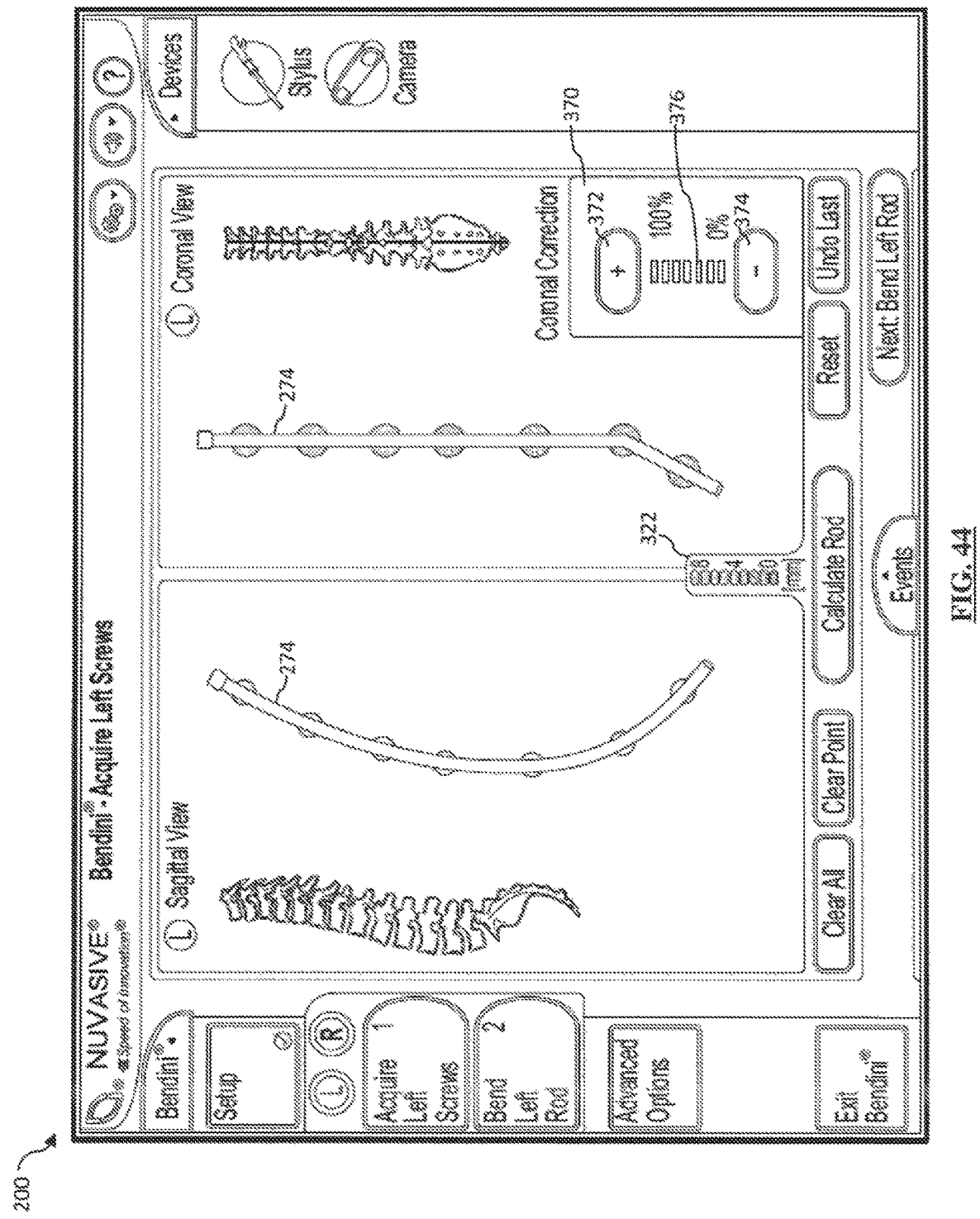
FIG. 44 is a screen shot illustrating a third example screen of the Coronal Correction feature according to the second embodiment.

According to the embodiment shown in FIGS. 42-44, the user may straighten a subset of the screw points within the construct (segmental coronal correction). Based on the sequence those points are inputted into the system, a best-fit segmental reference line is generated through the points in the direction of the last chosen point. If an inferior point 364 is selected first and then a superior point 362 is selected second, the system 10 will draw the best-fit segmental reference line 378 superiorly as shown in FIG. 42. Conversely, if a superior point 362 is selected first and then an inferior point 364 is selected second, the system 10 will draw the best-fit segmental reference line 378 inferiorly. Using the Coronal Correction Menu 370, the user manipulates the + and − buttons 372, 374 to adjust the percentage of correction desired. In the example shown in FIG. 43, the amount of desired correction is shown as 100% on the percentage correction indicator 376, meaning the rod solution 274 will be a straight line in the coronal plane and all selected screw locations will be adjusted to fit the rod/line. As shown in FIG. 44, however, unselected screw locations 380 will not be adjusted to fit the rod/line and their relative locations will be inputted into the system 10 and taken into consideration when the rod calculation is made. As depicted in FIG. 43, the system 10 may include a color-coded offset distance indicator 322 to provide the user with an indication of the distance each digitized screw position will be adjusted in the coronal plane as set forth above. If the user deems this an acceptable rod solution, the user selects the "Calculate Rod" button 272 to view the rod solution 274 (FIG. 44) and receive bend instructions or proceeds to another advanced feature as will be described in greater detail below.

According to another embodiment, segmental coronal correction may be achieved relative to the patient's central sacral vertical line (CSVL) instead of a best-fit segmental reference line running through two selected digitized screw locations. The CSVL is the vertical line passing through the center of the sacrum that may serves as the vertical reference line for the patient's coronal deformity as well as a guide for spinal correction in the coronal plane in accordance with the coronal assessment and correction features of the present disclosure.

Figure 45:
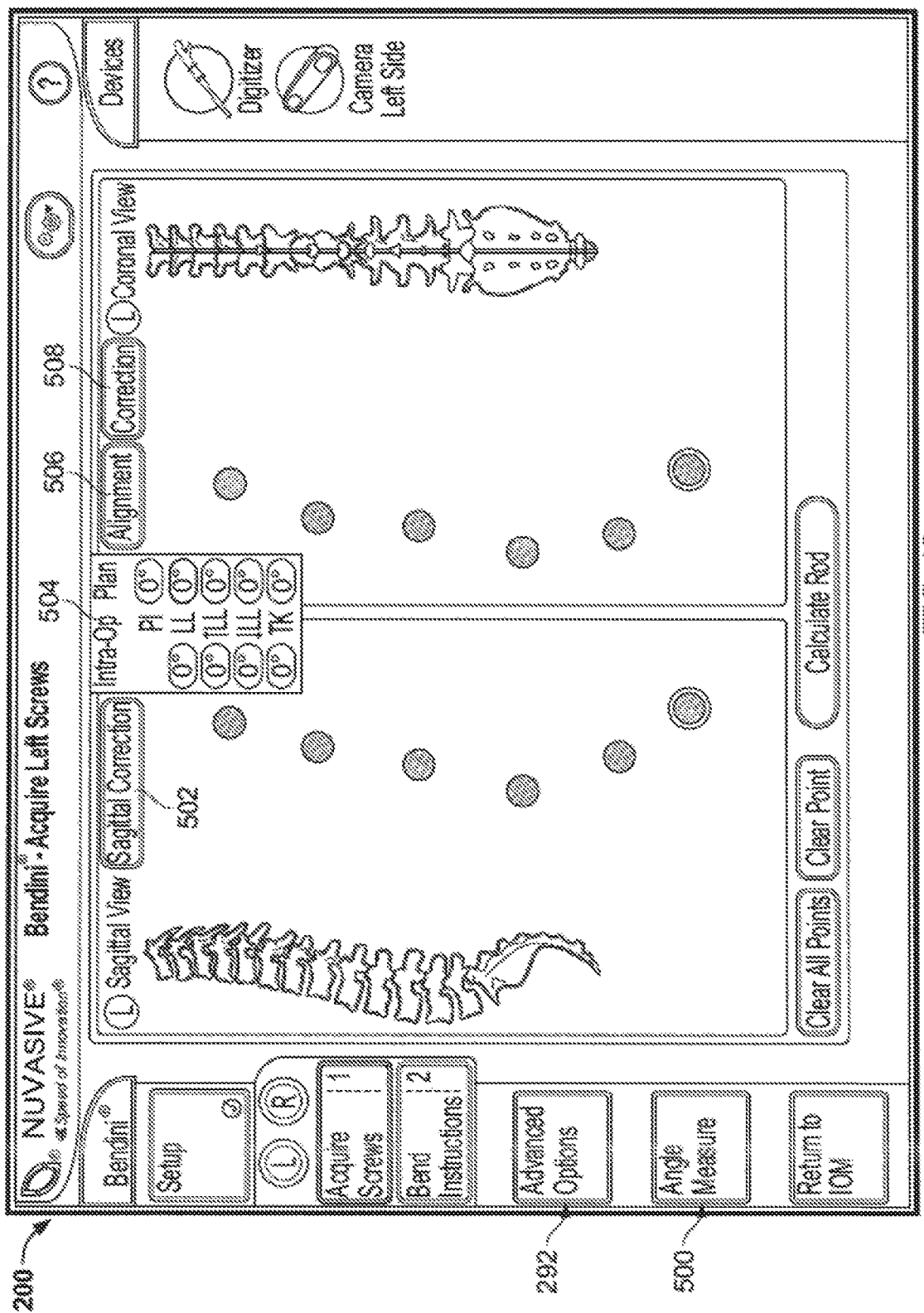
FIG. 45 is a screen shot illustrating a first example screen of the Coronal Correction feature according to the third embodiment.
Figure 46:
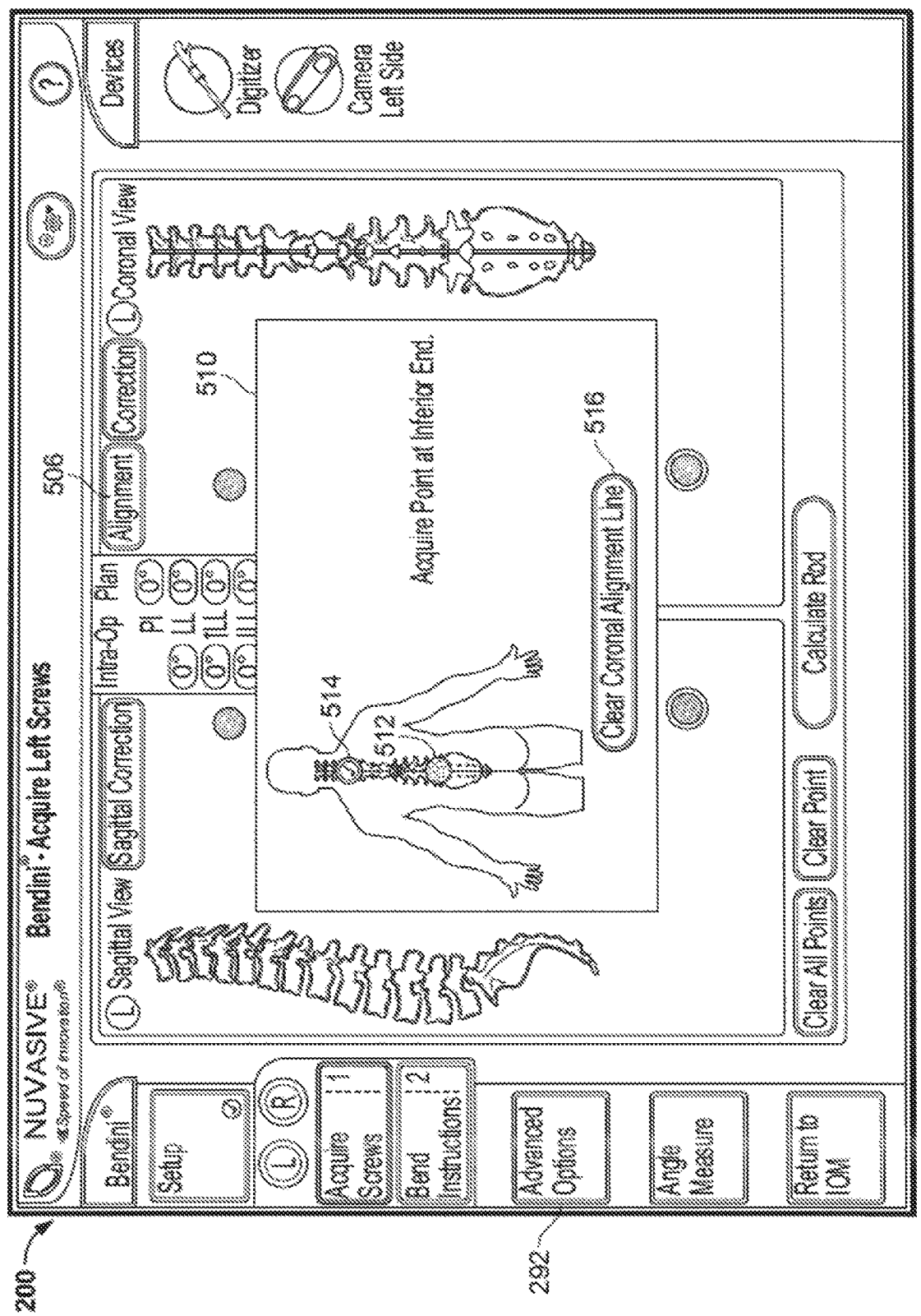
FIG. 46 is a screen shot illustrating a second example screen of the Coronal Correction feature according to the third embodiment.
Figure 47:
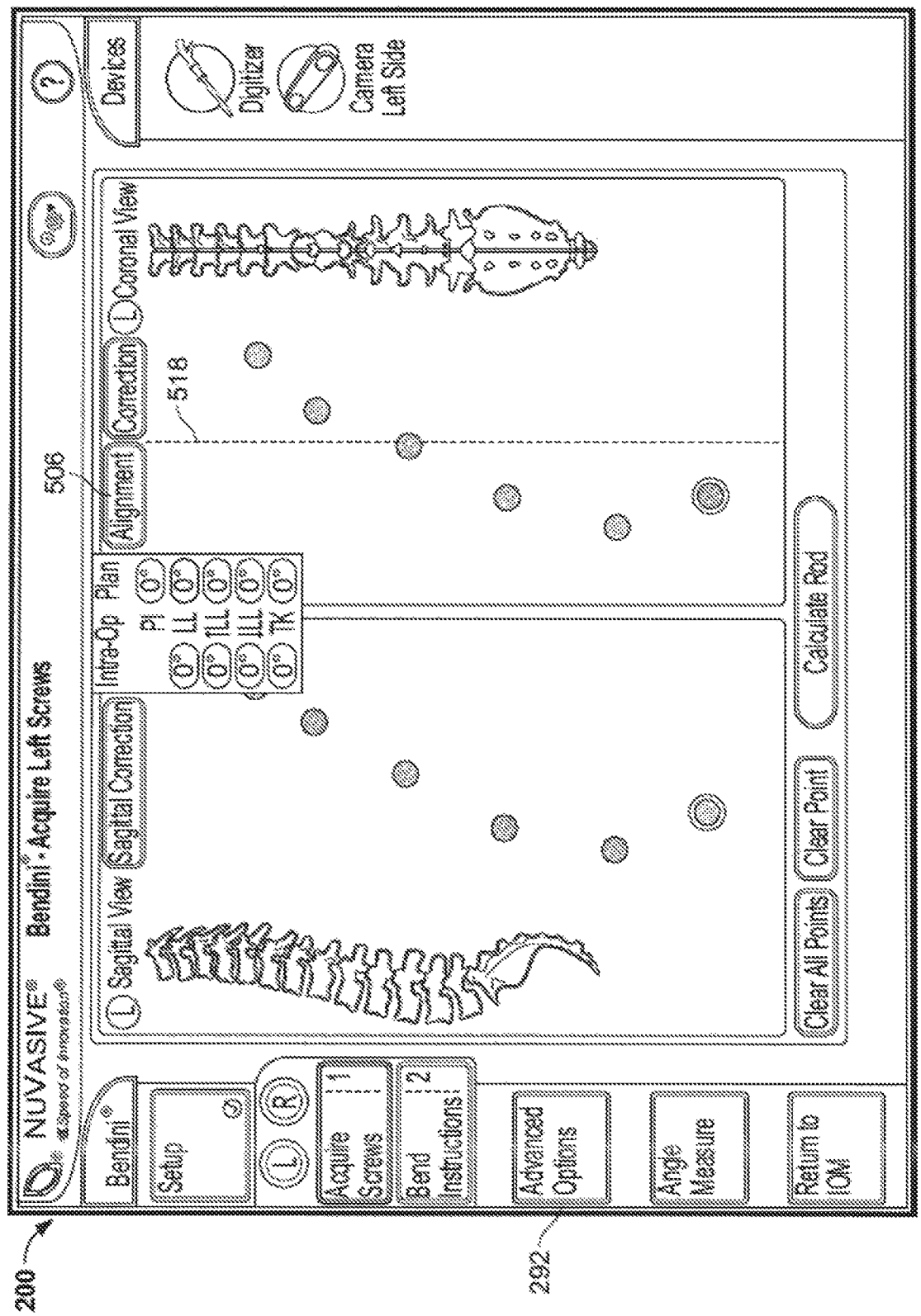
FIG. 47 is a screen shot illustrating a third example screen of the Coronal Correction feature according to the third embodiment.
Figure 48:
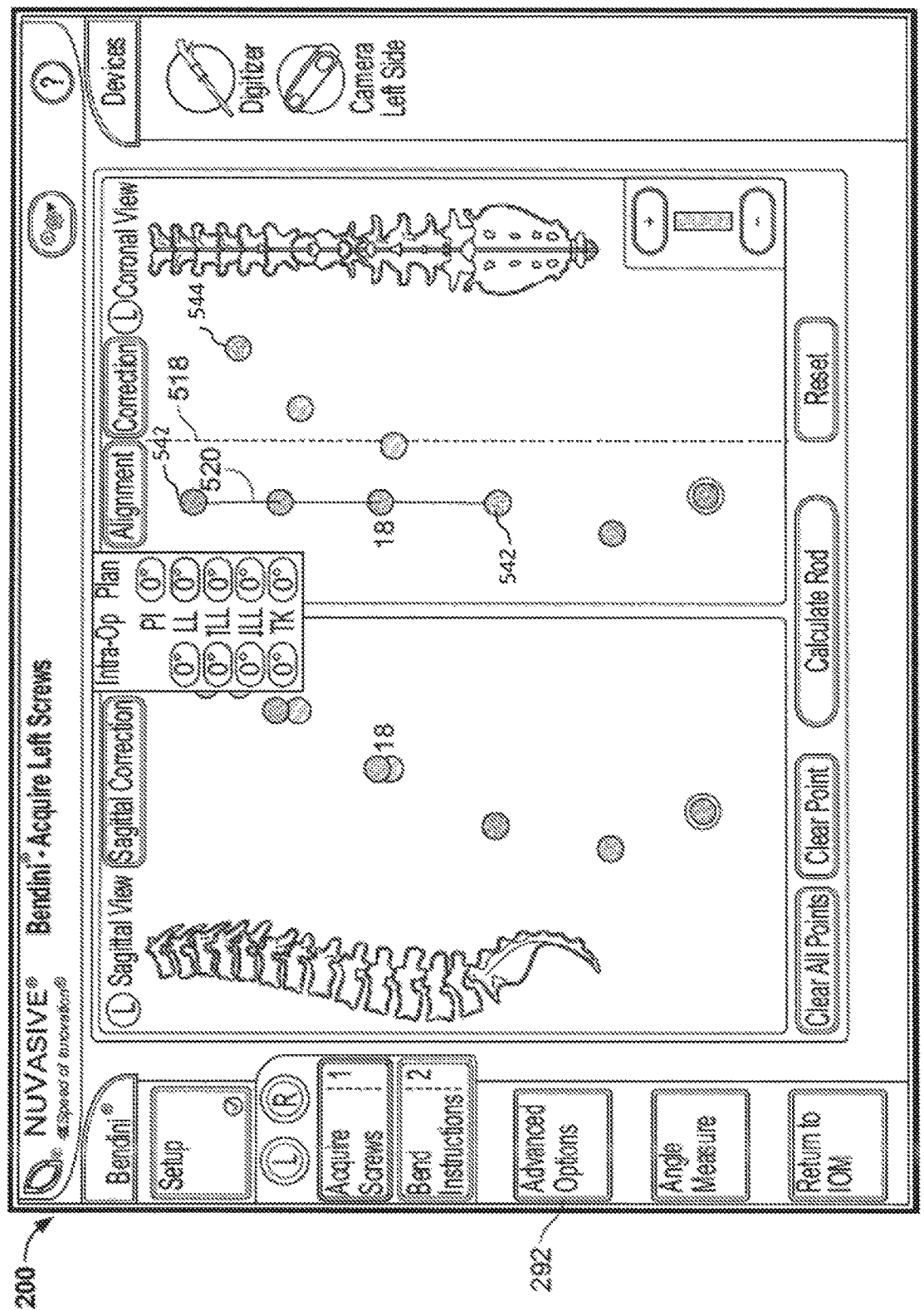
FIG. 48 is a screen shot illustrating a fourth example screen of the Coronal Correction feature according to the third embodiment.
Figure 49:
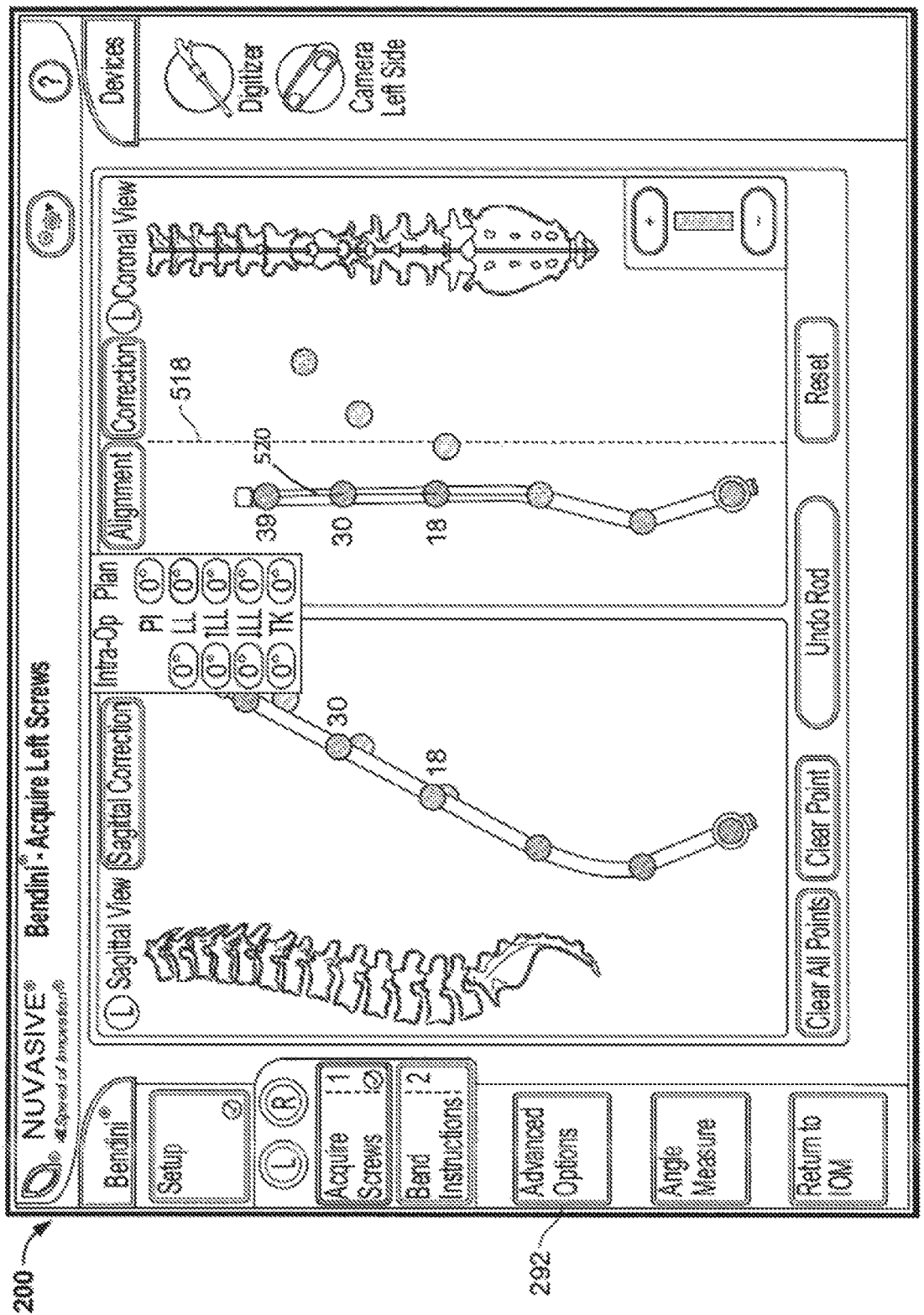
FIG. 49 is a screen shot illustrating a fifth example screen of the Coronal Correction feature according to the third embodiment.

FIGS. 45-49 illustrate a method for using the CSVL line for assessing coronal deformity and achieving coronal correction according to one embodiment. Preferably, this method commences after all screws are implanted into the patient and digitized in the manner set forth above. The user generates one or more radiographic images of the sacrum, localizes a superior and inferior point on the sacrum, and marks those points (e.g., implants Caspar pins, marks the patient's skin with a marker, etc.). Next, the user selects the "Alignment" button 506 (FIG. 45). Upon such a selection, the user is prompted to digitize the marked skin points representing the superior and inferior sacral landmarks. As shown by way of example in FIG. 46, box 510 may pop up to instruct the user of the various steps of the workflow. Here, the superior point on the sacrum has already been digitized (shown as digitized point 512) and check mark 514. Box 510 further instructs the user to "Acquire Point at Inferior End." Selecting "Clear Coronal Alignment Line" 516 to re-digitize the sacral points and/or exit out of the CSVL coronal correction feature. Once the superior and inferior sacral points are digitized, a dashed line 518 representing the patient's true CSVL line appears on the screen (FIG. 47) and the digitized screw locations 264 are reoriented in system 10 relative to the CSVL line 518. The display 200 in the coronal view now represents the patient's current coronal curve relative to a vertical reference (CSVL). From here, the user may select two points (i.e., the screw segment) he/she would like to correct or straighten relative to the CSVL. As shown in FIG. 48, by way of example, the user selects points 542 and 544. According to one implementation, the first point chosen 542 is the point of rotation of the segment and the origin of the straightening line 520. The second point 544 determines the direction of the straightening line 520. The straightening line 520 may be drawn parallel to the CSVL line 518 as the objective of coronal correction is to make the spine as vertical as possible in the coronal plane. If the user deems this an acceptable rod solution, the user selects the "Calculate Rod" button 272 to view the rod solution 274 (FIG. 49) and receive bend instructions. The user now has a rod solution he/she can pull the screws to, knowing that it is straight relative to the CSVL line and therefore providing the desired correction of the coronal deformity. The user will and receive bend instructions or proceeds to another advanced feature as will be described in greater detail below.

In some spinal procedures (e.g., anterior column deformity correction procedures), restoring a patient's spine to a balanced position may be a desired surgical outcome. According to a broad aspect of the invention, the system 10 may include a Global Spinal Balance feature in which the control unit 16 is configured to receive and assess 1) preoperative spinal parameter measurements; 2) target spinal parameter inputs; 3) intraoperative spinal parameter inputs; and 4) postoperative spinal parameter inputs. One or more of these inputs may be tracked and/or compared against other inputs to assess how the surgical correction is progressing toward a surgical plan, assess how close the patient's spine is to achieving global spinal balance, and utilized to develop/refine an operative plan to achieve the desired surgical correction.

Spinal parameters may comprise the patient's Pelvic Incidence (PI), Pelvic Tilt (PT), Sacral Slope (SS), Lumbar Lordosis (LL), Superior Lumbar Lordosis (↑LL), Inferior Lumbar Lordosis (↓LL), C7 Plumb Line offset (C7PL), and Thoracic Kyphosis (TK), T1 tilt, and Sagittal Vertical Axis (SVA) measurements. The target spinal parameter measurements may be a clinical guideline (by way of example only, the SRS-Schwab classification, or a patient-specific goal based on that patient's anatomy). Depending on user preference, these spinal parameters may comprise Pelvic Incidence (PI), Pelvic Tilt (PT), Sacral Slope (SS), Lumbar Lordosis (LL), Superior Lumbar Lordosis (↑LL), Inferior Lumbar Lordosis (↓LL), C7 Plumb Line offset (C7PL), and Thoracic Kyphosis (TK), T1 tilt, and Sagittal Vertical Axis (SVA) measurements.

Figure 50:
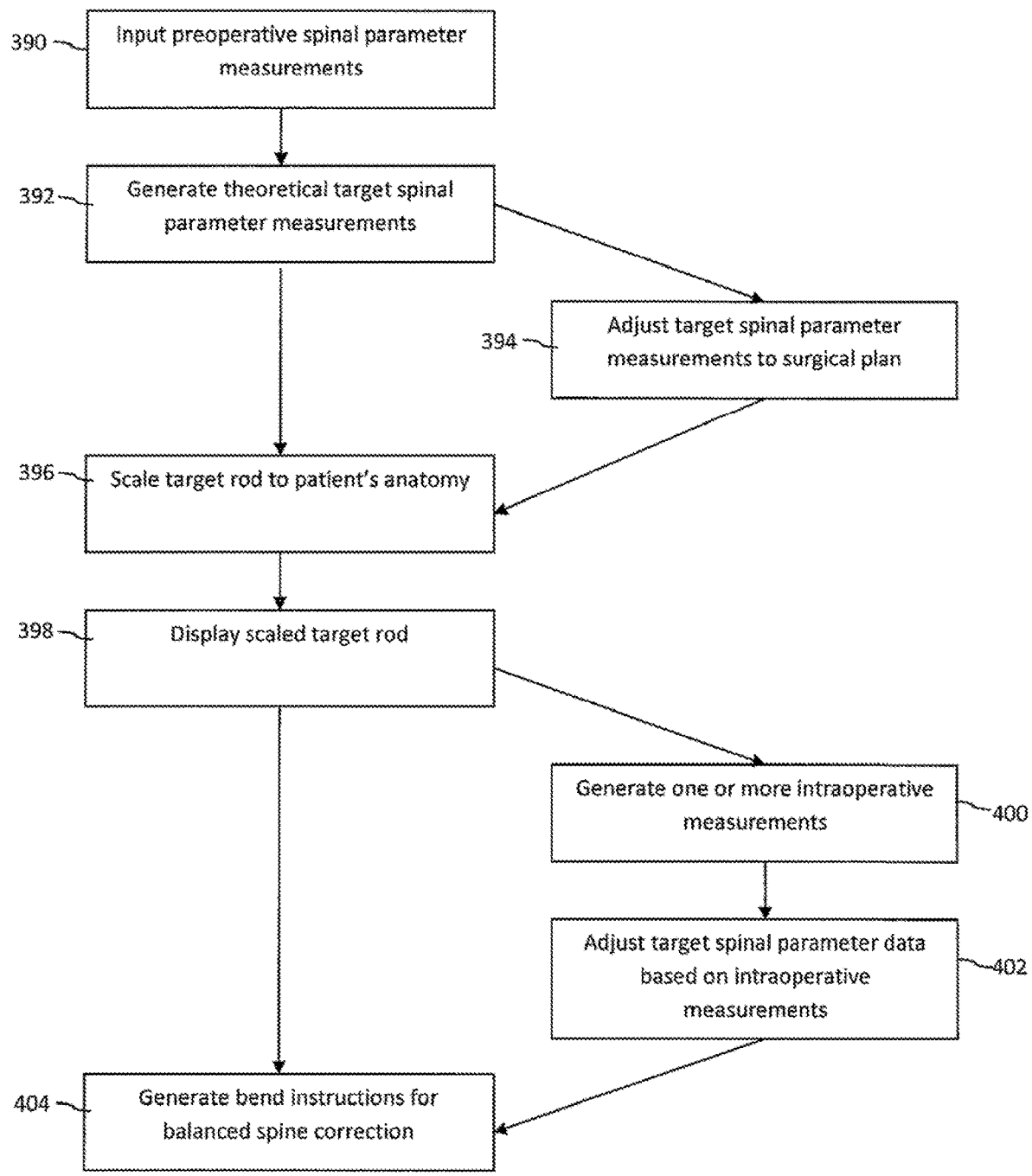
FIG. 50 is a flowchart illustrating the steps of the Global Spinal Balance feature according to one embodiment.

FIG. 50 depicts a flowchart indicating the steps of the Global Spinal Balance feature according to one embodiment. At step 390, the system 10 inputs a patient's preoperative spinal parameter measurements. Next, the system generates theoretical target spinal parameter measurements (step 392). One or more target spinal parameter measurements may be optionally adjusted the user in accordance with a surgical plan a step 394. At step 396, a target spinal rod may be scaled to match the patient's anatomy using the theoretical or adjusted target spinal parameter measurements from step 392 or 394. This scaled target rod may then be displayed 398 to the user. Optionally, the system 10 may generate one or more measurements (step 400) during the surgical procedure. At step 402, the target spinal parameter data may then be adjusted based on the intraoperative measurements from step 400. Finally, the system 10 may generate bend instructions for balanced spine correction.

Figure 52:
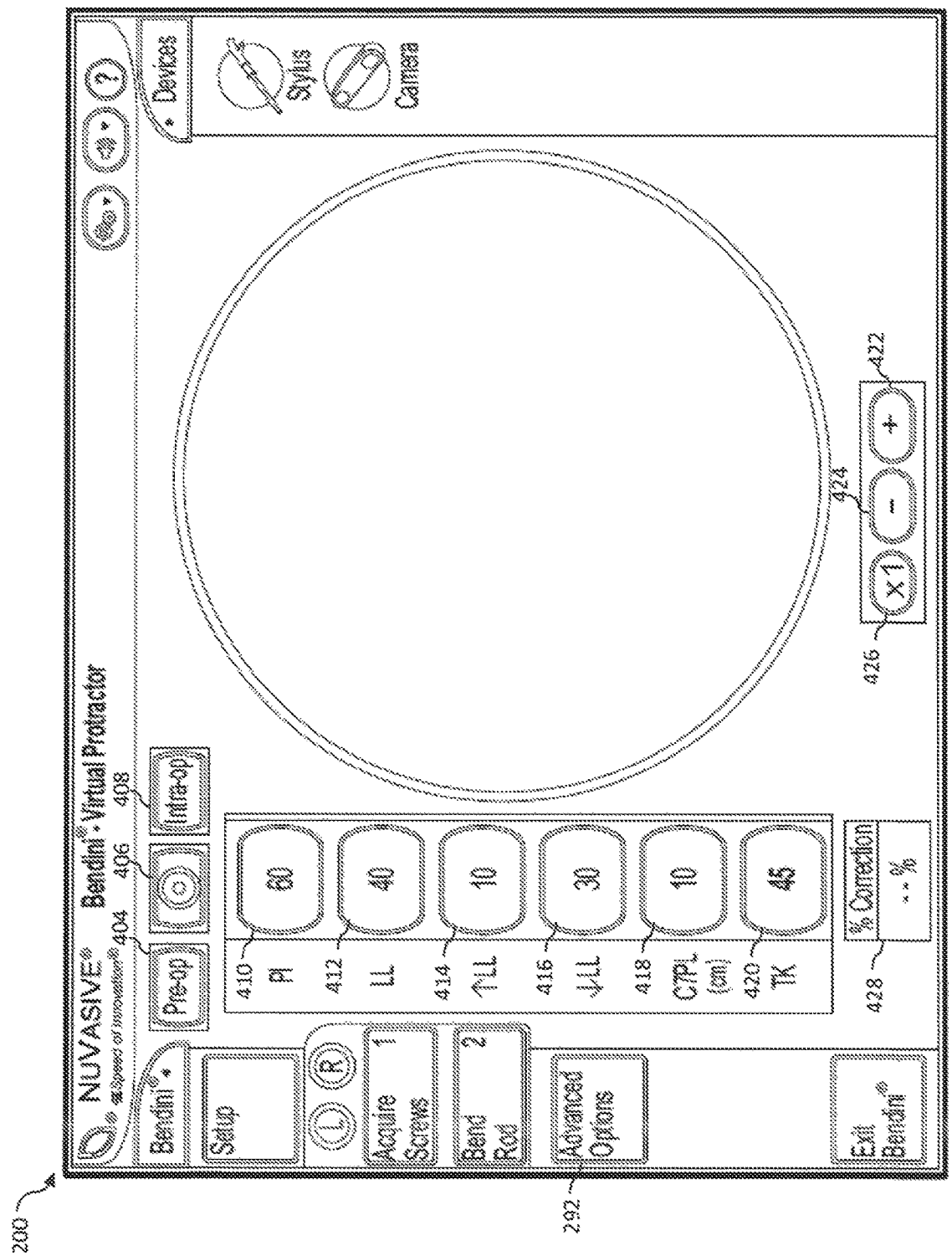
FIG. 52 is a screen shot illustrating a first example screen of the Global Spinal Balance feature in pre-operative mode.

The user may input a patient's preoperative measurements into the system 10 as depicted, by way of example in FIG. 52. Selecting the Pre-Op measurement button 404 allows the user to input measurements into PI, LL, Superior LL, Inferior LL, C7PL, and TK input fields 408, 410, 412, 414, 416, 418, and 420 respectively. Such pre-operative measurements may be obtained from manual measurement means imported from any number of commercially-available desktop and mobile software applications. These pre-operative anatomical measurements may be used to understand the imbalance in the patient's deformed spine as well as help determine an operative plan to implant devices that would adjust or form the spine to a more natural balance (e.g., rods, screws, a hyperlordotic intervertebral implant, etc.).

Figure 54:
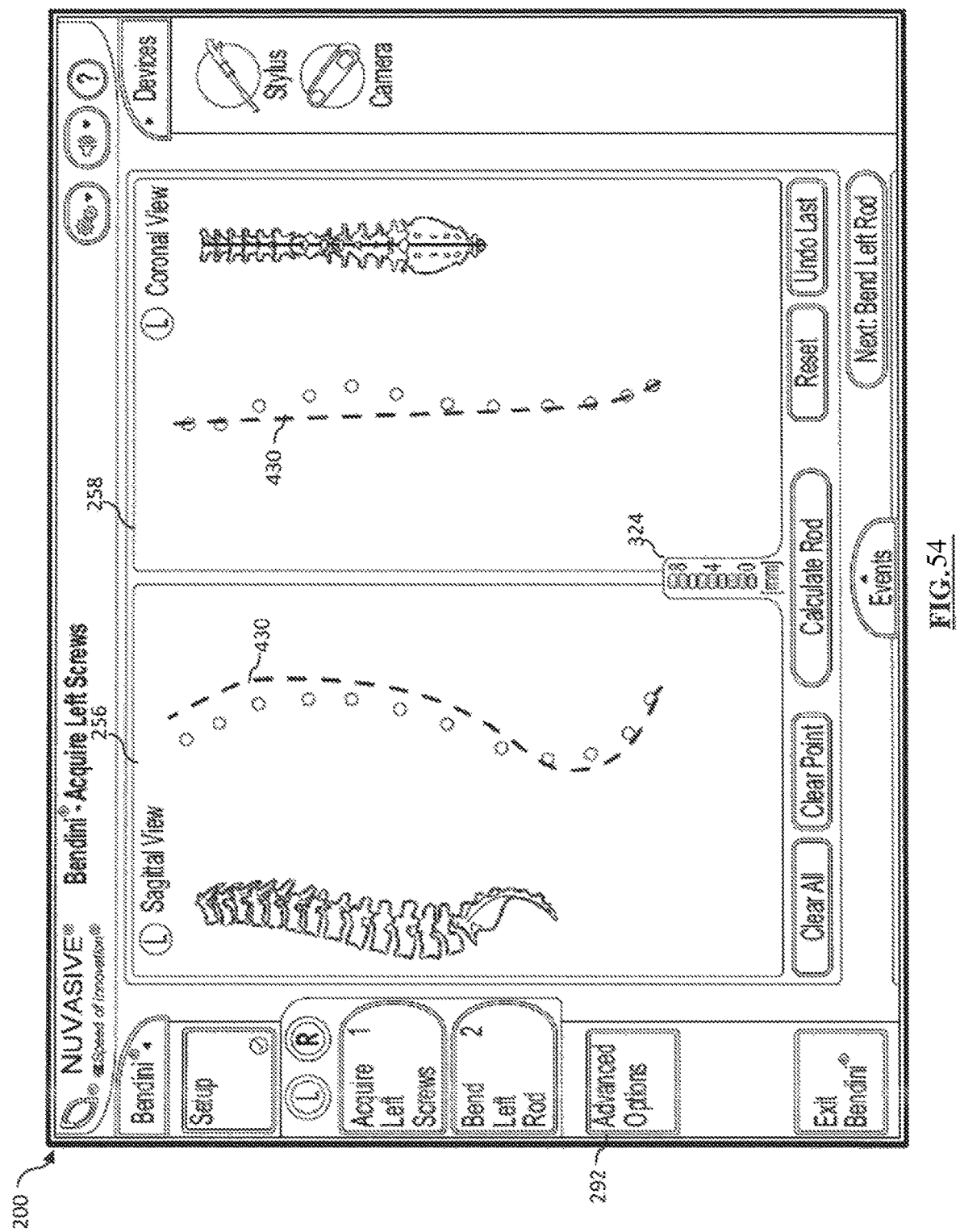
FIG. 54 is a screen shot illustrating a second example screen of the Global Spinal Balance feature in target mode.

As depicted in FIG. 52, the global spinal balance feature allows the user to adjust the patient's anatomical measurement values to the user's preferred target spinal parameters for a balanced and/or aligned spine. According to one implementation, selecting the target measurement button 406 populates measurements into input fields 410, 412, 414, 416, 418, 420 that represent an ideal or properly balanced spine. If the user accepts these target spinal parameters, the system 10 would output a theoretical rod solution comprising rod shapes and curves representing an ideal or properly balanced spine scaled and overlaid onto the digitized screw points as shown in FIG. 54. The system 10 may also include a color-coded offset distance indicator 322 to provide the user with an indication of the distance each digitized screw position is from the rod solution in the sagittal and coronal planes as set forth above. Alternatively, if the user seeks to achieve a different alignment, he or she may use buttons 422, 424, 426 to adjust these target spinal parameters. The user could then refer to the correction indicator 428 for an indication of how much correction (relative to the preoperative and theoretical spinal parameters) would be achieved based on those adjusted input correction values. The user's input correction values would then drive the rod bending algorithm (based on the digitized screw locations) to a rod shape customized to the user's plan for that particular placement. The final rod could be positioned within the patient and the screws and spine would be adjusted to the rod at the desired alignment.

Figure 55:
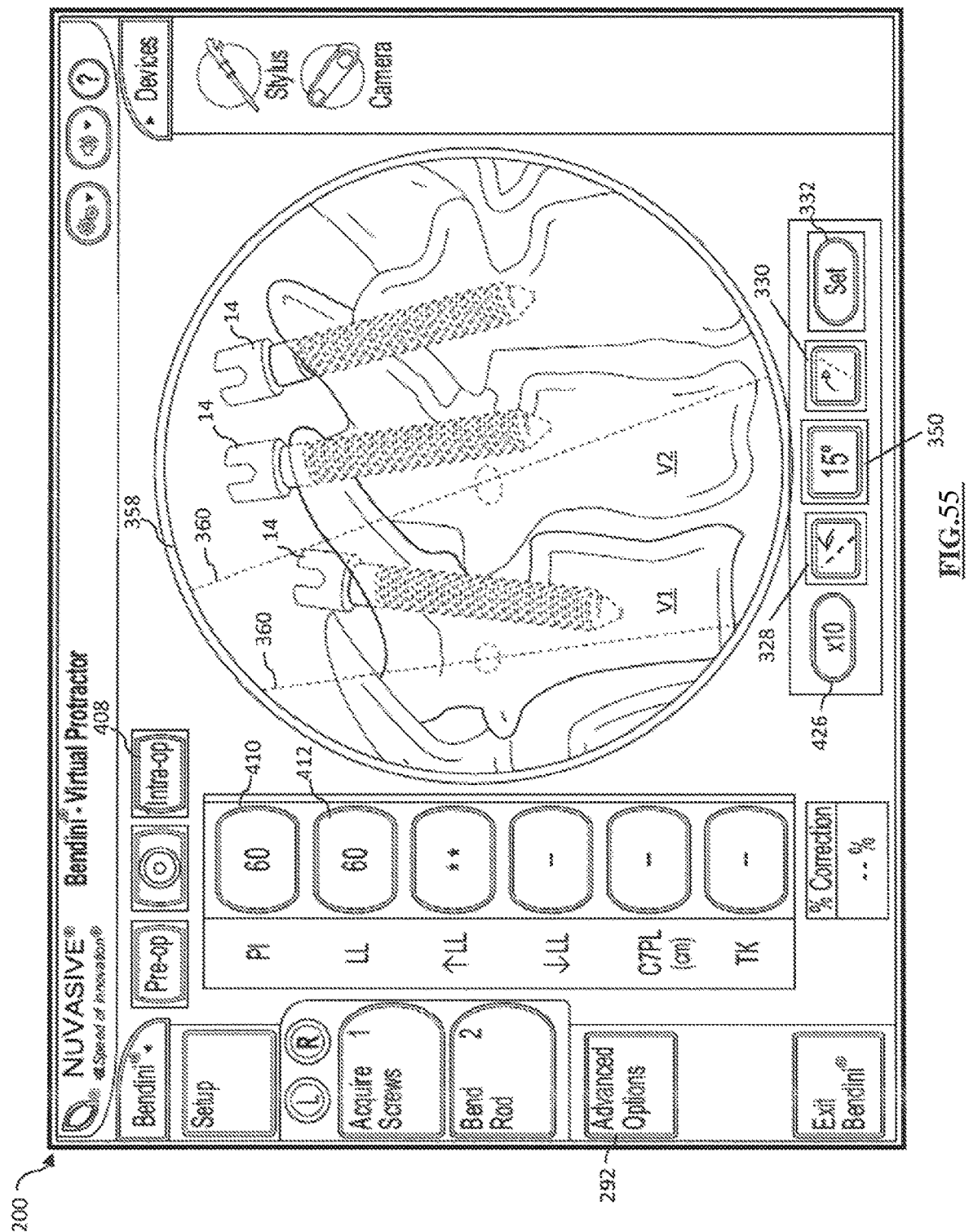
FIG. 55 is a screen shot illustrating a first example screen of the Global Spinal Balance feature in intraoperative mode.
Figure 56:
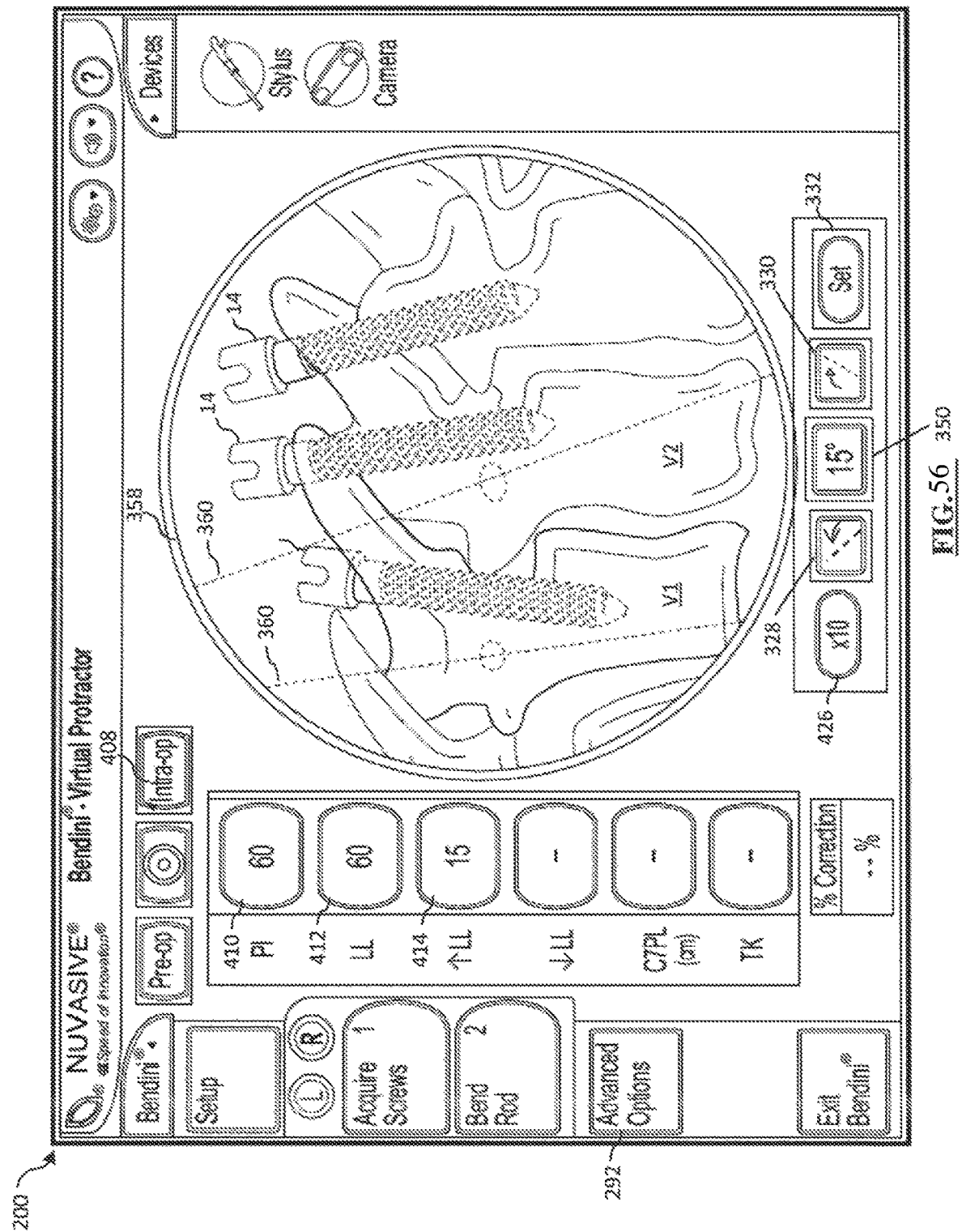
FIG. 56 is a screen shot illustrating a second example screen of the Global Spinal Balance feature in intraoperative mode.

In accordance with the Global Spinal Balance feature, spinal parameter inputs may be assessed intraoperatively. For example, the user may wish to intraoperatively measure the amount of lumbar lordosis that has been achieved (for example, after placement of an intervertebral implant). As depicted in FIGS. 55-56, the system 10 may include be configured to obtain or import one or more lateral images, generate one or more lines between two or more landmarks on the patient's anatomy, determine a relationship between those landmarks, and adjust one or more spinal parameters to be used in generating the rod solution. As shown by way of example in FIG. 55, the user first selects the intraoperative measurement button 408. Next, lateral radiographic image 358 may be inputted into the system 10. The user may touch the screen 200 and move lines 360 over at least two points of interest (e.g. the superior endplate of V1 and the superior endplate of V2) and the system 10 then measures the angle between the two lines 360. As shown in FIG. 56, the system 10 measures this angle as 15 degrees as indicated in the angle measurement field 350. Optionally, the system may compare the intraoperative measurement to the preoperative and/or target spinal parameter value and provide an indication to the user of how much correction has been achieved relative to the pre-operative and theoretical spinal parameters. Using the angle measurement buttons 328, 330, the user may increase the desired angle of correction of the spine in the sagittal plane (i.e., add or subtract lordosis or kyphosis). As the angle is adjusted, the amount of adjustment may dynamically displayed within angle measurement field 350. The system 10 may include a color-coded offset distance indicator (not shown) to provide the user with an indication of the distance each digitized screw position will be adjusted in the sagittal plane as described above. Once the desired amount of angular correction is updated, the user may press the "Set" button 332 and then the "Calculate Rod" button (not shown in this view). The system then displays a rod solution 274 incorporating the user's intraoperative objective for correction of the spine in the sagittal plane.

Figure 57:
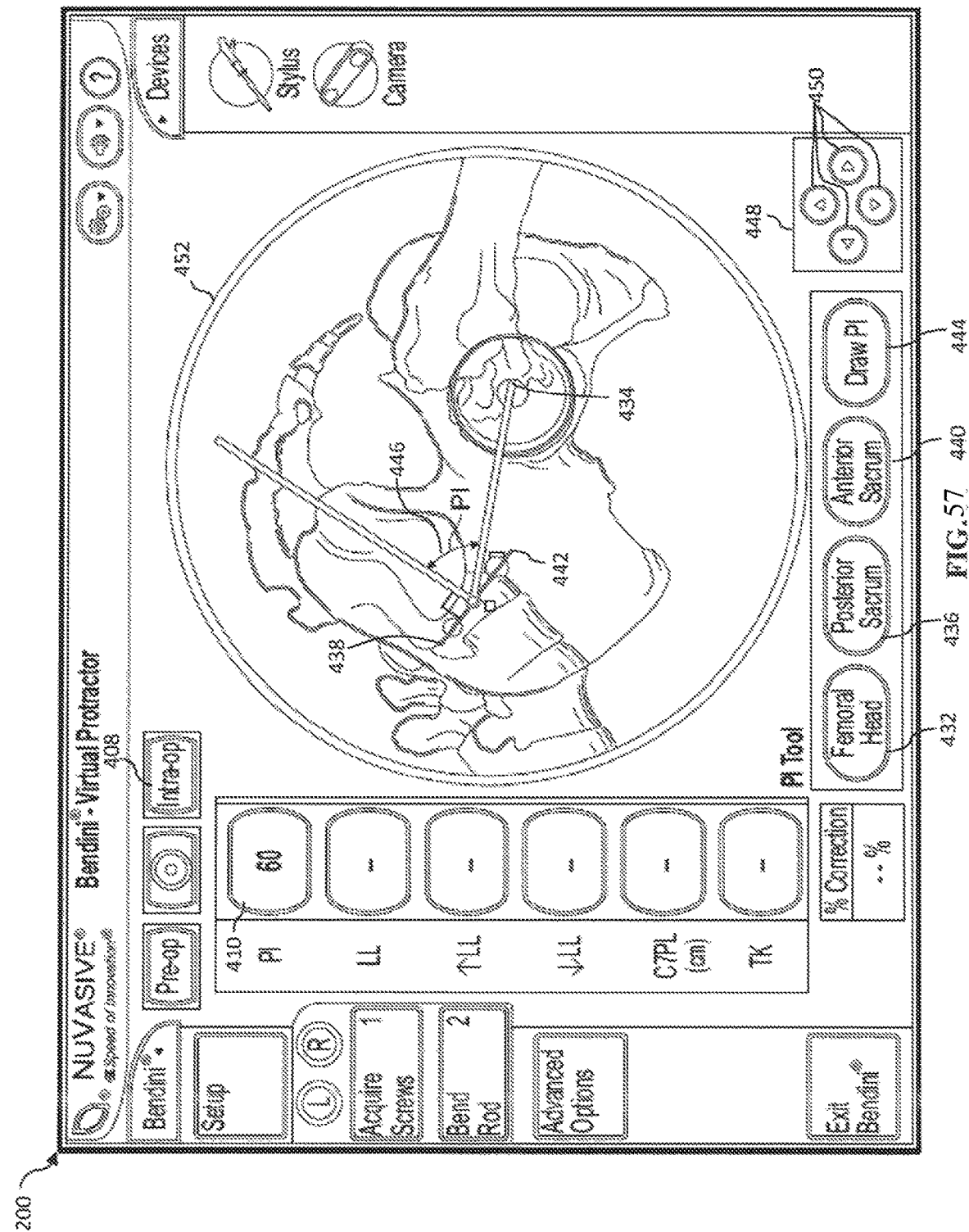
FIG. 57 is a screen shot illustrating a third example screen of the Global Spinal Balance feature in intraoperative mode.

The user may also wish to intraoperatively measure the patient's pelvic incidence angle. As shown in FIG. 57, selecting the intra-op measurement button 408 optionally brings up a PI assessment tool. The system 10 obtains a fluoroscopic image 452 of the patient's pelvis. The user first selects the femoral head button 432 and uses arrows 450 on the PI Adjustment Menu 448 to locate the center point of the femoral head 434. Next, the user selects the posterior sacrum button 436 and uses arrows 450 to identify the posterior aspect of the sacral endplate 438. Then, the user selects the anterior sacrum button 440 and uses arrows 450 to identify the anterior aspect of the sacral end plate 442. With all PI inputs selected, the user may press the "Draw PI" button 446 after which the system 10 automatically draws and measures the pelvic incidence angle 446 for the user.

Figure 51:
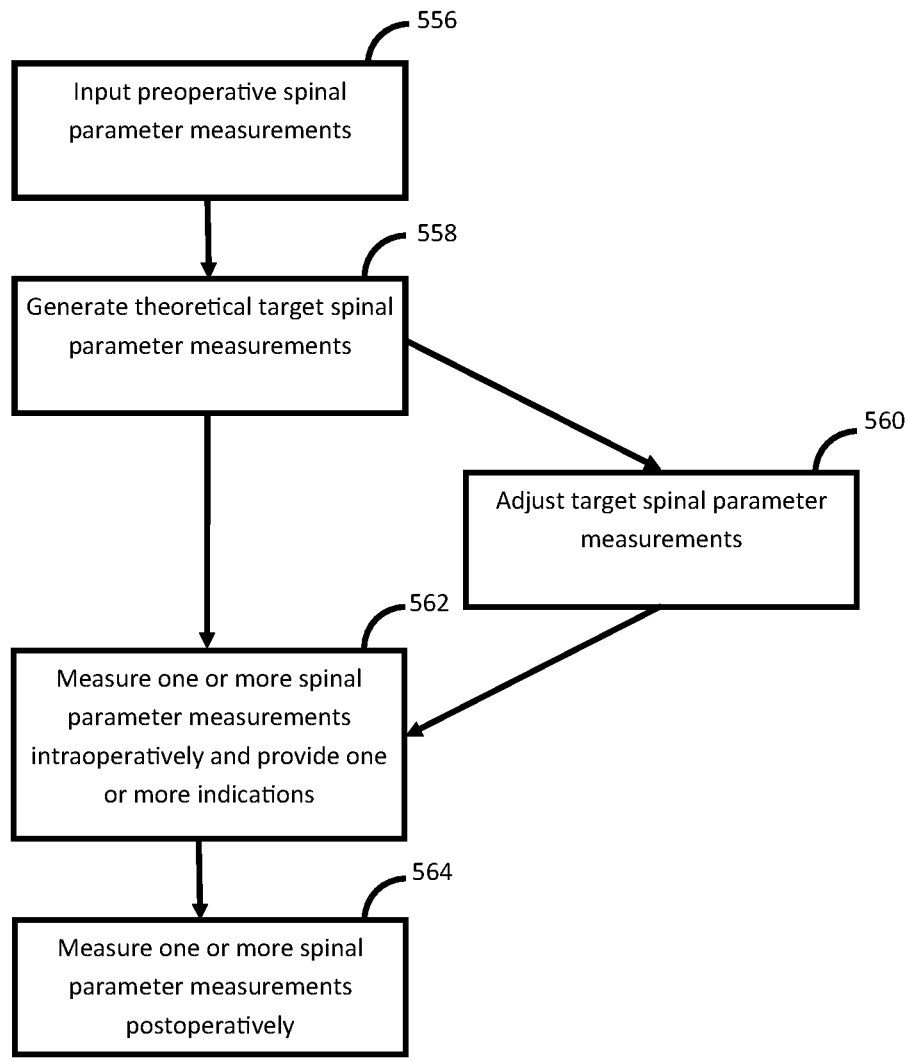
FIG. 51 is a flowchart illustrating the steps of the Global Spinal Balance feature according to a second embodiment.

The illustrative embodiment above included the use of target spinal parameter inputs to determine a target rod shape to restore or improve spinal balance. However, it is to be appreciated that not all embodiments require such a determination. FIG. 51 depicts a flowchart indicating the steps of an intraoperative Global Spinal Balance assessment feature according to one embodiment. At step 556, the system 10 inputs a patient's preoperative spinal parameter measurements. Next, the system generates theoretical target spinal parameter measurements (step 558). One or more target spinal parameter measurements may be optionally adjusted the user in accordance with a surgical plan at step 560. At step 562, the system may measure one or more spinal parameter measurements intraoperatively and provide one or more indications to the user how the surgical procedure is progressing. At step 564, the system may measure one or more spinal parameter measurements postoperatively to assess the final status of the deformity correction and balance achieved.

The user may input a patient's preoperative measurements into the system 10 as depicted, by way of example in FIG. 52. Selecting the Pre-Op measurement button 404 allows the user to input measurements into PI, LL, Superior LL, Inferior LL, C7PL, and TK input fields 408, 410, 412, 414, 416, 418, and 420 respectively. Such pre-operative measurements may be obtained from manual measurement means imported from any number of commercially-available desktop and mobile software applications. These pre-operative anatomical measurements may be used to understand the imbalance in the patient's deformed spine as well as help determine an operative plan to implant devices that would adjust or form the spine to a more natural balance (e.g., rods, screws, a hyperlordotic intervertebral implant, etc.).

Figure 53:
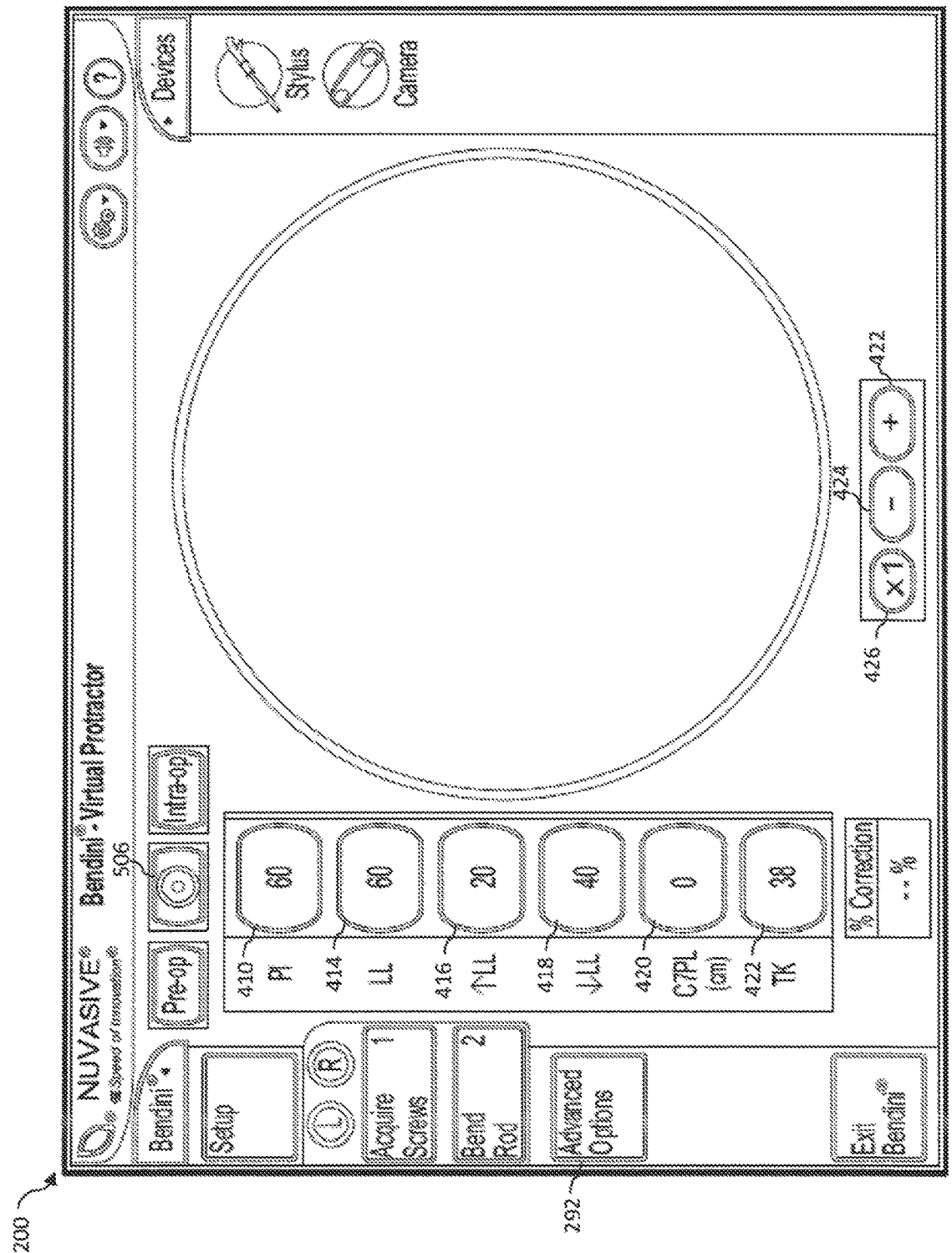
FIG. 53 is a screen shot illustrating a first example screen of the Global Spinal Balance feature in target mode.

As depicted in FIG. 53, the global spinal balance feature allows the user to adjust the patient's anatomical measurement values to the user's preferred target spinal parameters for a balanced and/or aligned spine. According to one implementation, selecting the target measurement button 406 populates measurements into input fields 410, 412, 414, 416, 418, 420 that represent an ideal or properly balanced spine. Alternatively, if the user seeks to achieve a different alignment, he or she may use buttons 422, 424, 426 to adjust these target spinal parameters. In accordance with the Global Spinal Balance feature, spinal parameter inputs may be assessed intraoperatively. For example, the user may wish to intraoperatively measure the amount of lumbar lordosis that has been achieved (for example, after placement of an intervertebral implant). As depicted in FIGS. 55-56, the system 10 may include be configured to obtain or import one or more lateral images, generate one or more lines between two or more landmarks on the patient's anatomy, determine a relationship between those landmarks, and adjust one or more spinal parameters to be used in generating the rod solution. As shown by way of example in FIG. 55, the user first selects the intraoperative measurement button 408. Next, lateral radiographic image 358 may be inputted into the system 10. The user may touch the screen 200 and move lines 360 over at least two points of interest (e.g. the superior endplate of V1 and the superior endplate of V2) and the system 10 then measures the angle between the two lines 360. As shown in FIG. 56, the system 10 measures this angle as 15 degrees as indicated in the angle measurement field 350. Optionally, the system may compare the intraoperative measurement to the preoperative and/or target spinal parameter value and provide an indication to the user of how much correction has been achieved relative to the pre-operative and theoretical target spinal parameters. Using the angle measurement buttons 328, 330, the user may increase the desired angle of correction of the spine in the sagittal plane (i.e., add or subtract lordosis or kyphosis). As the angle is adjusted, the amount of adjustment may dynamically displayed within angle measurement field 350.

According to one or more implementations, the user is provided with a visual indication as to how the surgical procedure is proceeding relative to the targeted plan. By way of example, as once the intraoperative lumbar lordosis measurement is within 10 degrees of the planned pelvic incidence value, then both buttons will be represented on the screen 200 as green. Once the intraoperative lumbar lordosis measurement is greater than 10 but less than 21 degrees of the planned pelvic incidence value, then both buttons will be represented on the screen 200 as yellow. Once the intraoperative lumbar lordosis measurement is equal or greater than 21 degrees, then both buttons will be represented on the screen 200 as red.

In some circumstances, the user may want to assess the amount/severity of coronal plane deformity and/or intraoperatively ascertain the amount of correction achieved with a given rod bend configuration. The system may include a Coronal Offset Assessment feature configured to obtain or import one or more Anterior-Posterior images, acquire digital position information regarding landmarks on the patient's anatomy, generate one or more lines between those landmarks, and determine a relationship between those landmarks.

Figure 58:
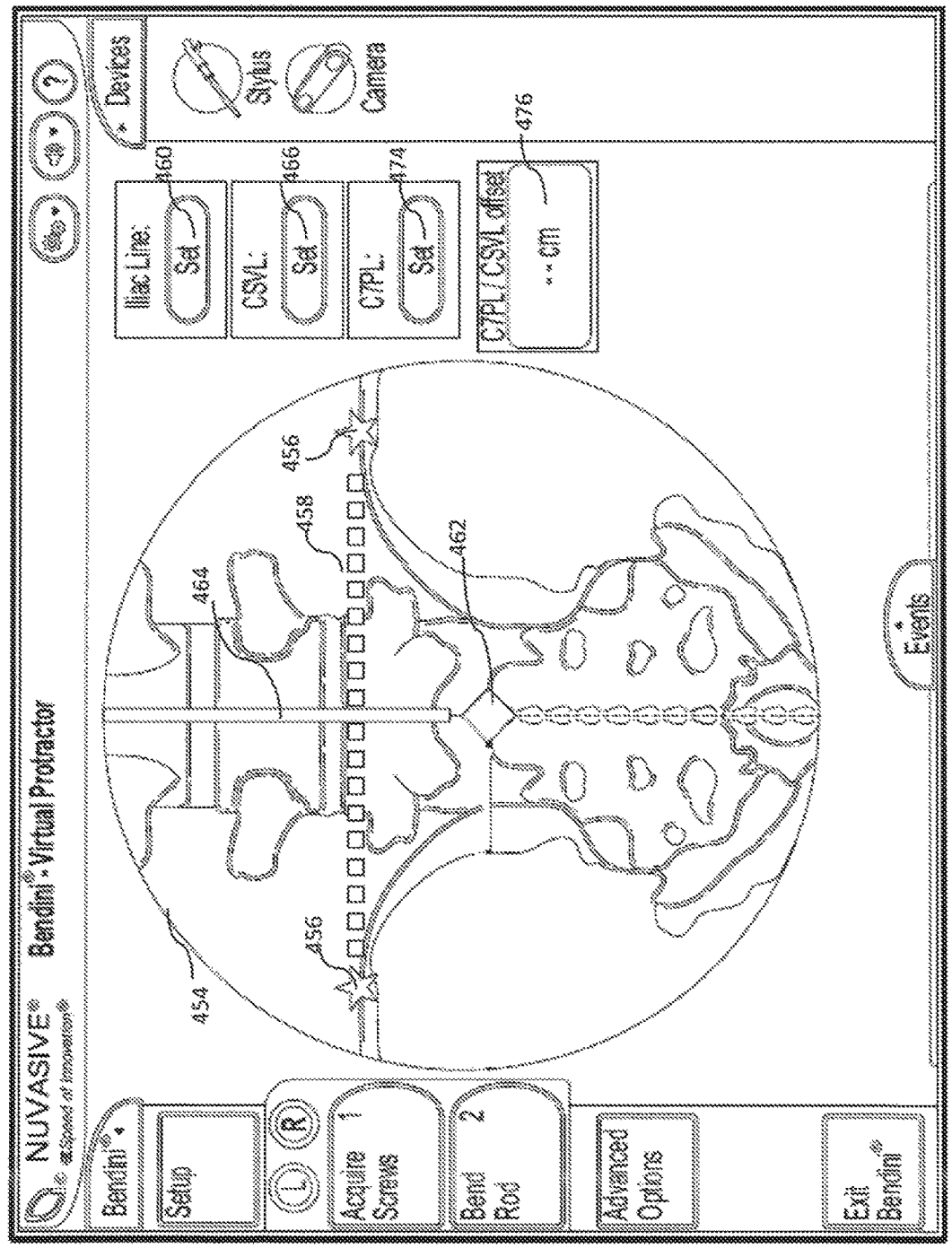
FIG. 58 is a screen shot illustrating a fourth example screen of the Global Spinal Balance feature in intraoperative mode.
Figure 59:
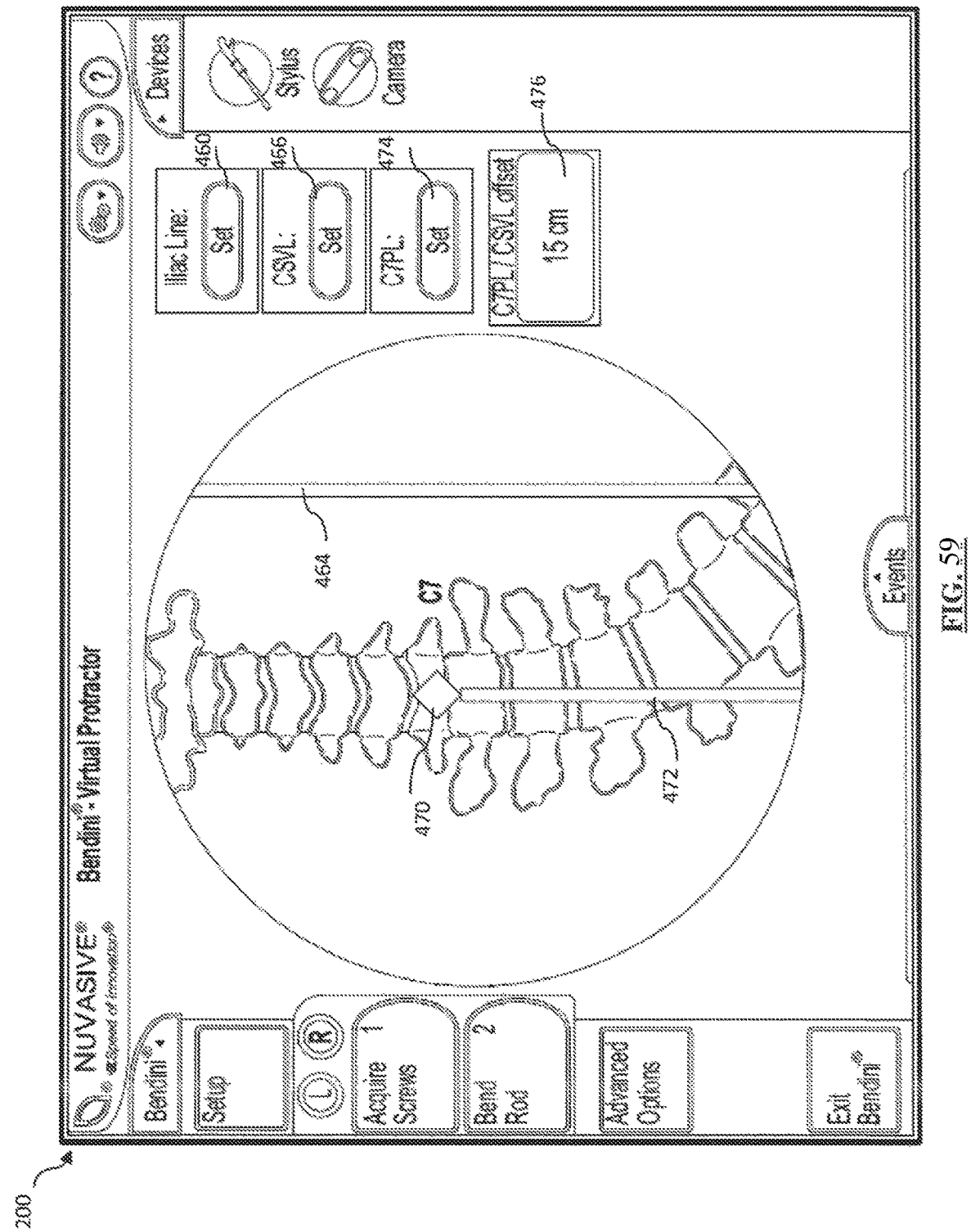
FIG. 59 is a screen shot illustrating a fifth example screen of the Global Spinal Balance feature in intraoperative mode.

According to some implementations, the system 10 first obtains a fluoroscopic image 454 of the iliac sacral region (FIG. 58). The user digitizes two points 456 and selects the Iliac Line: Set button 460 to establish a horizontal iliac line 458. Next, the user digitizes the midpoint 462 of the sacrum and selects the CSVL Line: Set button 466 and the system 10 automatically generates an orthogonal line (CSVL line 464) from the sacral midpoint 462 to the iliac line 458. The system 10 then obtains a fluoroscopic image 468 of the C7 vertebra as depicted in FIG. 59. The user digitizes the midpoint 470 of the C7 vertebra and selects the "C7PL: Set" button 474 and the system 10 automatically generates an orthogonal line (C7PL line 476) from the midpoint 470 of C7 to the iliac line 458. Finally, the system 10 calculates the coronal offset distance (in box 476) using the offset distance between the CSVL line 464 and the C7PL line 476 line. As such, the user is given an intraoperative assessment of the amount of coronal offset corrected or left to be corrected which affords the opportunity to decide if a surgical planning goal has been achieved or if one or more spinal parameter inputs need to be updated with respect to coronal alignment.

As set forth above, the system 10 provides the user with the functionality to select two points on the spine and generate a best-fit reference line between those two points to which to generate a rod solution and correct the spine to. In some instances, it may be desirable to intraoperatively represent the spine's true deformity in the coronal plane and to correct the spine relative to a pelvic anatomical reference. As such, there is provided a virtual orthogonal reference line through which the user may intraoperatively assess a deformed spine against and/or correct coronal a spinal deformity to.

Figure 60:
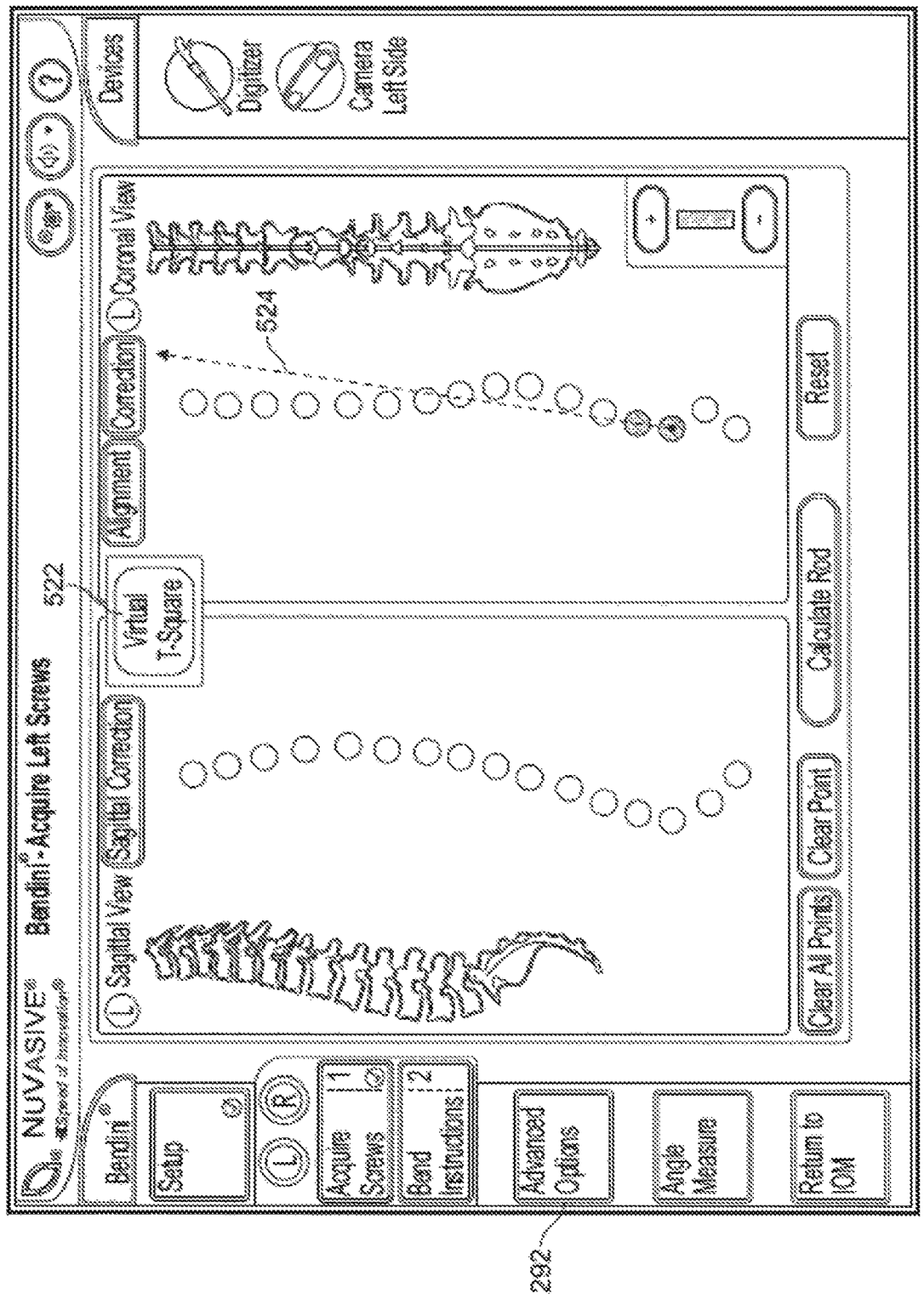
FIG. 60 is a screen shot illustrating a first example screen of a Coronal Assessment and Correction feature according to a first embodiment.
Figure 61:
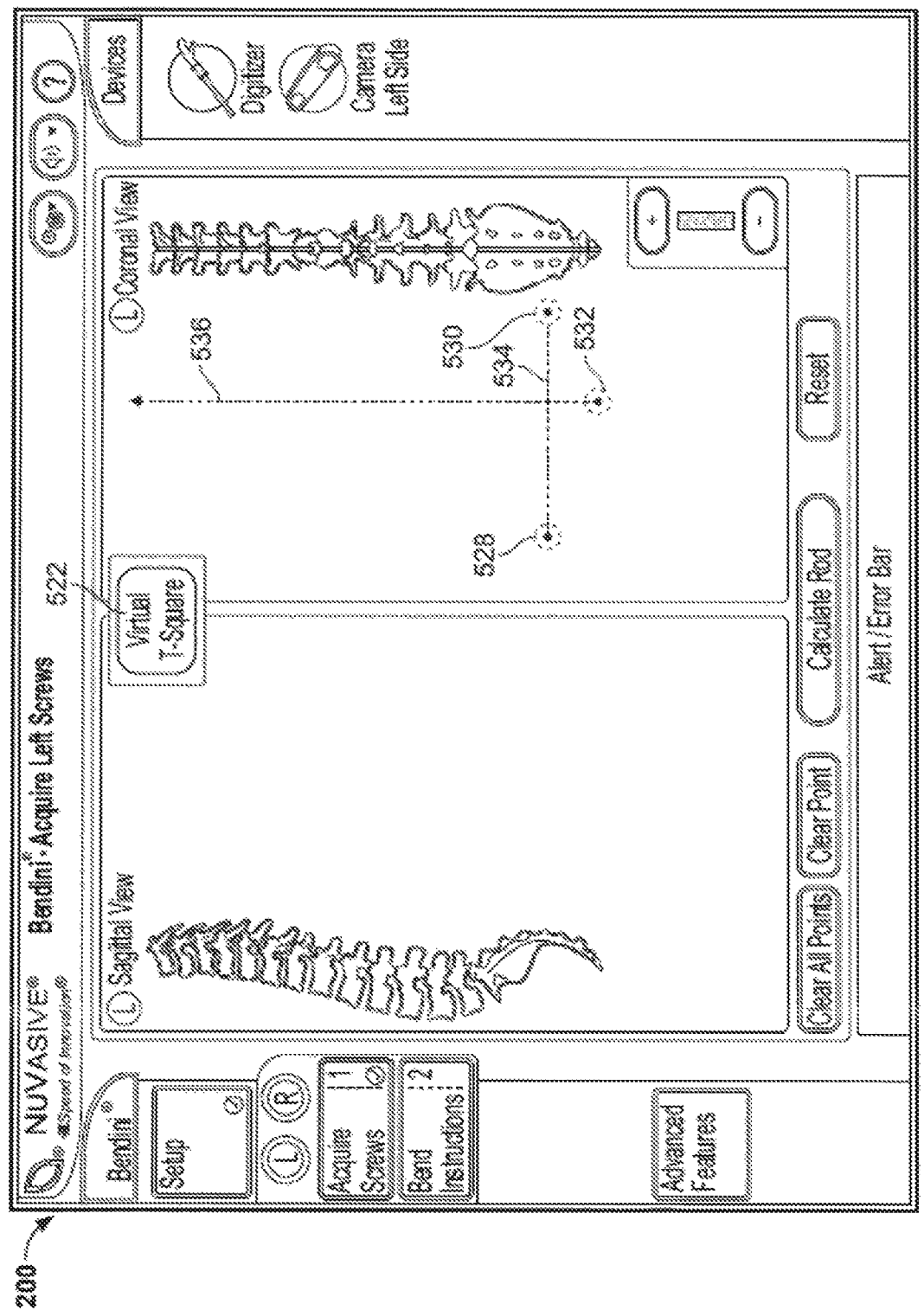
FIG. 61 is a screen shot illustrating a second example screen of a Coronal Assessment and Correction feature according to the embodiment of FIG. 60.
Figure 62:
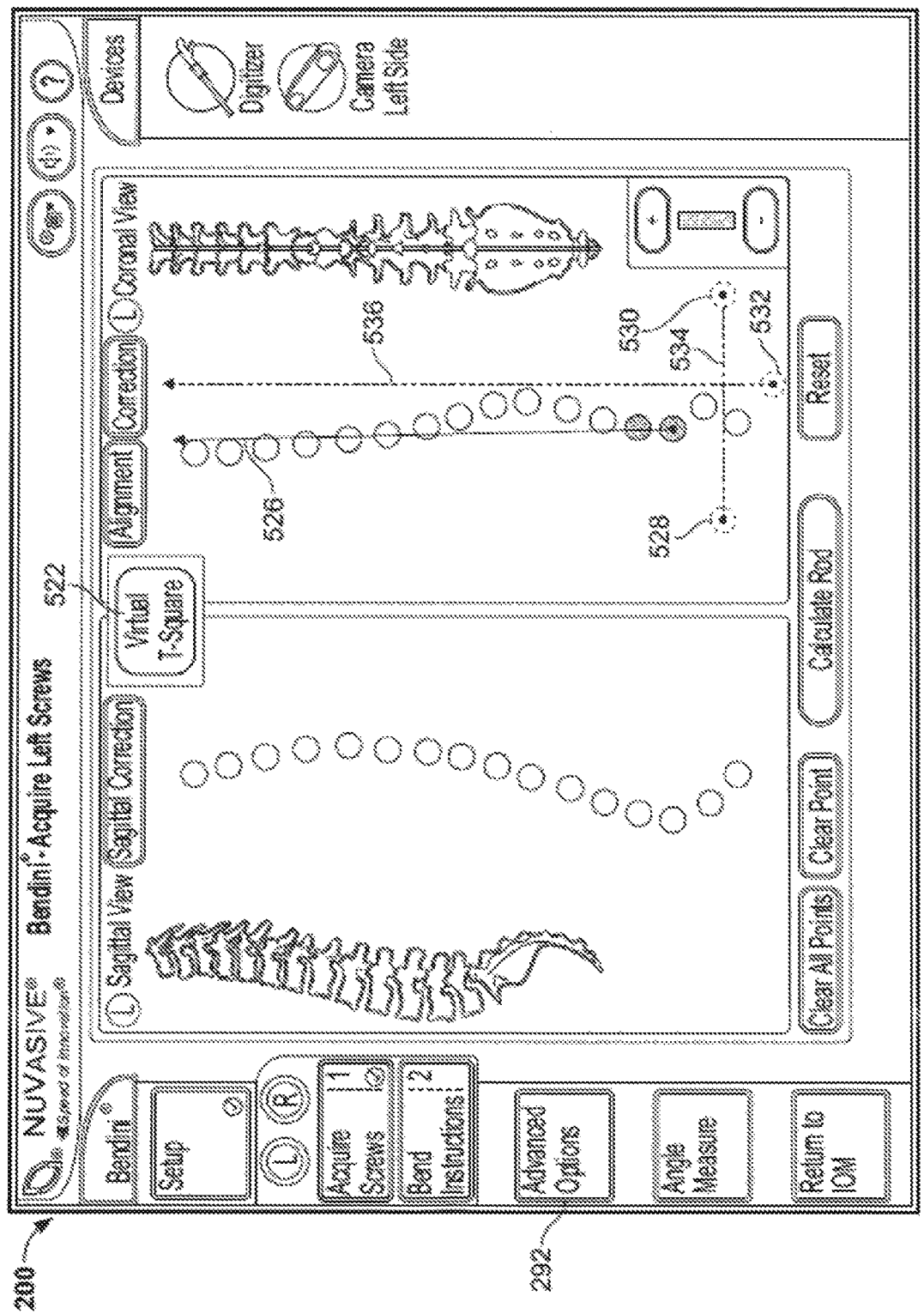
FIG. 62 is a screen shot illustrating a third example screen of a Coronal Assessment and Correction feature according the embodiment of FIG. 60.

For purposes of illustration, assume that a user has digitized the screw points 264 as shown in FIG. 60 and contemplates performing segmental coronal correction (as set forth above) with straightening line 524 as the best-fit reference line. The user may select the "Virtual T-Square" button 522 to activate the Virtual T-Square feature. FIGS. 61-62 describe the Virtual T-Square feature in greater detail. First, the user localizes three points of reference on the patient's anatomy via c-arm fluoroscopy and marks the location of those anatomical references (e.g., implants Caspar pins, marks the patient's skin with a marker, etc.). By way of example, the anatomical points of reference may be the left iliac crest, right iliac crest, and sacral midpoint. The user may be prompted (via text box, audible alert, and the like) to digitize each of the previously-identified anatomical reference points in a manner previously described herein. As the system 10 registers the digitized location of the marks designating the left and right points on the iliac crest, points 528, 530 appear on the screen 200, respectively and a horizontal line 534 representing the iliac line is drawn between the left and right iliac crest points 528, 530. This is shown, by way of example only as a dashed line 534 in FIG. 61. Next, the system 10 registers the digitized location of the sacral midpoint, point 532 appears on screen 200, and dashed line 536 representing the CSVL is drawn superiorly and orthogonal to the iliac line 534. According to one or more preferred embodiments, the system 10 may use one or more algorithms to detect that, when the Virtual T-Square feature is activated, the next three acquired digitized points will correspond to the three anatomical reference points of interests. With the CSVL line 536 established the digitized screw locations 264 may be reoriented in system 10 relative to the CSVL line 536, the user may select two points (i.e., the screw segment) he/she would like to correct or straighten relative to the CSVL as set forth above. The user may also generate a rod solution, receive bend instructions, and output a rod to pull the screws to, knowing that it is straight relative to the CSVL line as explained in detail above. Selecting "Reset" button 316 clears the lines 534, 536 and all adjustments in the Coronal View and returns the adjusted spheres to their original digitized locations. If the user toggles off the Virtual T-square button 522, the reference lines 526 are cleared and the orientation of the points converts back the best fit 524 within the Coronal View window.

Figure 63:
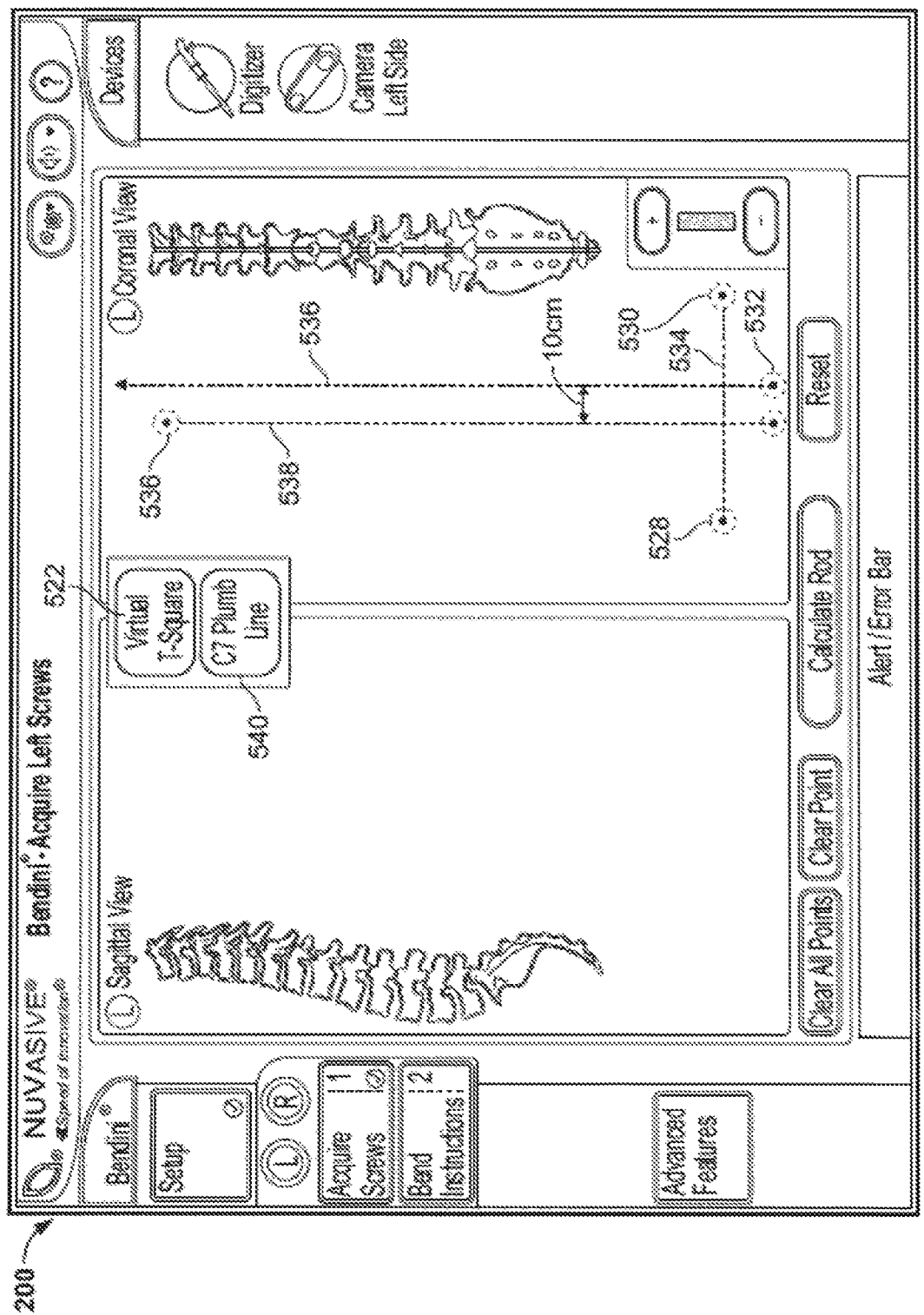
FIG. 63 is a screen shot illustrating a fourth example screen of a Coronal Assessment and Correction feature according to the embodiment of FIG. 60.

In some instances, in addition to intraoperatively assessing and/or correcting the spine's true coronal deformity, it may be further desirable to intraoperatively assess coronal spinal balance. Coronal spinal balance is determined by measuring the offset between the CSVL and a C7. According to some embodiments, the Virtual T-square feature may be included with a C7 Plumb Line Measurement feature. After the user has acquired the CSVL line via the Virtual T-square feature 522, the "C7 Plumb Line" button 540 is enabled. FIG. 63 describes the C7 Plumb Line feature in greater detail. First, the user localizes the center of the C7 vertebra via c-arm fluoroscopy and superficially marks the location of this anatomical reference on the patient's skin (e.g., with an "X"). The user may be prompted (via text box, audible alert, and the like) to digitize each of the C7 vertebra points in a manner previously described herein. As the system 10 registers the digitized location of the marks designating the C7 vertebra, point 558 appears on the screen 200 and a vertical line 538 representing the C7 Plumb Line is drawn parallel to the CSVL and orthogonal to the iliac line 534. This is shown, by way of example only as a dashed line 538 in FIG. 63. According to one or more preferred embodiments, the system 10 may use one or more algorithms to detect that, when the C7 Plumb Line feature is activated, the next acquired digitized points will correspond to the C7 anatomical landmark. Finally, the system 10 calculates the coronal offset distance using the offset distance between the CSVL line 536 and the C7PL line 538. By way of example, a double arrow line is drawn between the two vertical lines to represent the degree of coronal offset, and hence the spinal balance or imbalance in the coronal plane (shown in FIG. 63 as 10 cm). According to one or more embodiments (not shown), a color-coded coronal offset distance indicator may provide the user with an indication of the degree of coronal offset. By way of example, an offset of 0-2 cm could be indicated with a green double arrow line; an offset of 3-4 cm could be indicated with a yellow double arrow line; and an offset of greater than 4 cm could be indicated with a red double arrow line. As such, the user is given an intraoperative assessment of the amount of coronal offset corrected or left to be corrected which affords the opportunity to decide if a surgical planning goal has been achieved or if one or more spinal parameter inputs need to be updated with respect to coronal alignment.

Figure 64:
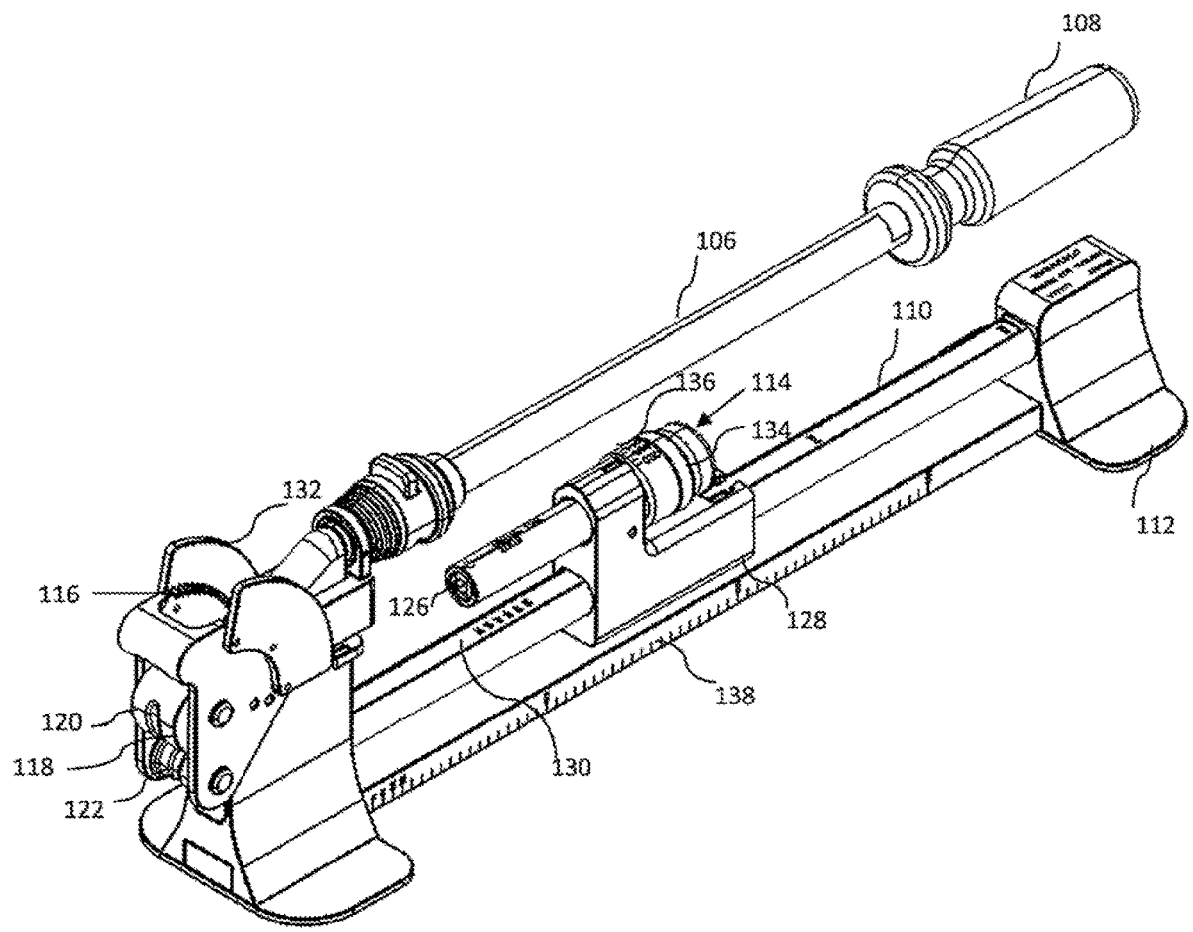
FIG. 64 is a perspective view of one embodiment of a mechanical rod bender comprising part of the system of FIG. 1.

From one or many of the features discussed above, once the user has selected the desired rod solution, the user then executes the bends using a mechanical rod bender 18. It is contemplated that the mechanical rod bender 18 may be any bender that takes into account six degrees of freedom information as it effects bends onto a spinal rod. By way of example, according to one implementation, the mechanical rod bender 18 may be the bender described in commonly-owned U.S. Pat. No. 7,957,831 entitled "System and Device for Designing and Forming a Surgical Implant" patented Jun. 7, 2011, the disclosure of which is hereby incorporated by reference as if set forth in its entirety herein. According to a second implementation, the mechanical rod bender 18 may be the bender shown in FIG. 64. First and second levers 106, 110 are shown as is lever handle 108 designed for grabbing the lever 106 manually and a base 112 for holding lever 110 in a static position. Second lever 110 has a rod pass through 114 so that an infinitely long rod can be used as well as steady the rod during the bending process with the rod bending device 18. The user grabs handle 108 and opens it to bend a particular rod by picking an angle on the angle gauge 132 and closing the handle 108 such that levers 106, 110 are brought closer together. The mechanical rod bender 18 in other embodiments could be produced to bend the rod during the handle opening movement as well. The rod moves through mandrel 118 and in between moving die 120 and fixed die 122. The rod is bent between the two dies 120, 122. Gauges on the bender 18 allow the user to manipulate the rod in order to determine bend position, bend angle, and bend rotation. The rod is held in place by collet 126. By sliding slide block 128 along base 112, the rod can be moved proximally and distally within the mechanical rod bender 18. Position may be measured by click stops 130 at regular intervals along base 112. Each click stop 130 is a measured distance along the base 112 and thus moving a specific number of click stops 130 gives one a precise location for the location of a rod bend.

The bend angle is measured by using angle gauge 132. Angle gauge 132 has ratchet teeth 116 spaced at regular intervals. Each ratchet stop represents five degrees of bend angle with the particular bend angle gauge 132 as the handle 106 is opened and closed. It is to be appreciated that each ratchet step may represent any suitable degree increment (e.g., between 0.25 degrees to 10 degrees). The bend rotation is controlled by collet knob 134. By rotating collet knob 134 either clockwise or counterclockwise, the user can set a particular rotation angle. The collet knob 134 is marked with regular interval notches 136 but this particular embodiment is continuously turnable and thus has infinite settings. Once a user turns knob 134, the user can set the knob 134 at a particular marking or in between or the like to determine a particular angle rotation to a high degree of accuracy. Additionally, base 112 may have a ruler 138 along its length to aid the user in measuring a rod intraoperatively.

According to another implementation, the rod bender 18 may be a pneumatic or motor-driven device which automatically adjusts the location, rotation and bend angle of the rod. By way of example, three motors may be utilized for each movement. A linear translator motor would move the rod in and out of the mandrel 118 and moving die 120. One rotational motor would rotate the rod and moving die 120. The bend calculations could be converted into an interface program that would run to power and control the motors. The automated bender would lessen the possibility of user error in following the manual bend instructions. It would also increase the resolution or number of bends that can be imparted in the rod making for a smoother looking rod.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware, or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used either by executing the code directly from the storage device, by copying the code from the storage device into another storage device such as a hard disk, RAM, etc. or by transmitting the code for remote execution.

While the invention is susceptible to various modifications and alternative forms, specific embodiments thereof have been shown, by way of example only, in the drawings and are herein described in detail. As can be envisioned by one of skill in the art, many different combinations of the above may be used and accordingly the present invention is not limited by the specified scope. It should be understood that the description herein of specific embodiments is not intended to limit the invention to the particular forms disclosed. On the contrary, the invention is to cover all modifications, equivalents, and alternatives falling within the spirit and scope of the invention as defined herein,

We claim:

1. A system for intraoperative planning and assessment of spinal deformity correction during a surgical spinal procedure, the system comprising:
   a spatial tracking system comprising an IR sensor and an IR tracking array, said IR tracking array being arranged along a proximal end of a surgical pointer tool capable of digitizing a location of an implanted surgical device and relaying to the spatial tracking system via the IR sensor;
   a control unit in communication with the spatial tracking system, said control unit being configured to:
   (a) receive digitized location data of a plurality of implanted screws;
   (b) receive digitized location data of at least one anatomical reference point;
   (c) generate at least one virtual anatomic reference line in a coronal plane based on the digitized location data of said at least one anatomical reference point;
   (d) accept one or more spine correction inputs that straighten one or more digitized screw locations in the coronal plane relative to the at least one virtual anatomic reference line; and
   (e) based on the one or more spine correction inputs, generating at least one rod solution output shaped to engage one or more of the plurality of implanted screws at locations distinct from the digitized location data.

2. The system of claim 1, wherein the virtual anatomic reference line is a central sacral vertical line.

3. The system of claim 2, wherein the at least one anatomical reference point comprises at least two points that correlate to the central sacral vertical line.

4. The system of claim 3, wherein the at least two points are selected from a position at a left iliac crest, a position at a right iliac crest, and a midpoint of a sacrum.

5. The system of claim 2, wherein the at least one anatomical reference point comprises two points that lie along the central sacral vertical line.

6. The system of claim 5, wherein the at least one anatomical reference point comprises a superior point and an inferior point on a sacrum.

7. The system of claim 2, wherein the one or more spine correction inputs comprises aligning all of the digitized screw locations relative to the central sacral vertical line in the coronal plane.

8. The system of claim 2, wherein the rod solution output is a vertically straight rod along at least a portion of a length.

9. The system of claim 1, wherein the control unit is further configured to generate at least one measurement value based on at least one anatomically-based reference point.

10. The system of claim 1, wherein the control unit is configured to generate at least one measurement value based on at least two anatomically-based reference lines.

11. The system of claim 10, wherein the measurement is an offset distance between said two reference lines.

12. The system of claim 11, wherein said two reference lines are a central sacral vertical line and a C7 plumb line.

13. The system of claim 12, wherein the control unit is further configured to assess intraoperative spinal balance based on a relationship between said central sacral vertical line and said C7 plumb line and communicate that assessment to a user.

14. The system of claim 13, wherein said relationship is based on a coronal offset distance between the central sacral vertical line and the C7 plumb line.

15. The system of claim 14, wherein the assessment to the user includes a visual communication, wherein said visual communication is a color in which a first color designates an offset distance indicating a balanced spine within a coronal plane and a second color designates an offset distance indicating an unbalanced spine within the coronal plane.

16. The system of claim 9, wherein the measurement value comprises an intraoperative lumbar lordosis angle and a planned pelvic incidence angle.

17. The system of claim 16, wherein the control unit is further configured to assess intraoperative spinal balance based on a relationship between an intraoperative lumbar lordosis angle measurement and a planned pelvic incidence angle.

18. The system of claim 17, wherein the lumbar lordosis angle and pelvic incidence angle are measured at least once during the surgical spinal procedure.

19. The system of claim 18, wherein the relationship is based on a variance between the intraoperative lumbar lordosis angle and the planned pelvic incidence angle.

20. The system of claim 19, wherein the assessment of the intraoperative spinal balance includes a communication, wherein said communication is a color in which a first color designates a variance indicating a balanced spine within a sagittal plane and a second color designates a variance distance indicating an unbalanced spine within the sagittal plane.

* * * * *